(12) United States Patent
Jimenez et al.

(10) Patent No.: US 10,518,012 B2
(45) Date of Patent: Dec. 31, 2019

(54) DEVICES, SYSTEMS, AND METHODS FOR IMPLANTING AND USING A CONNECTOR IN A TISSUE WALL

(71) Applicant: APK Advanced Medical Technologies, Inc., Atlanta, GA (US)

(72) Inventors: Jorge Hernan Jimenez, Atlanta, GA (US); Dustin Seth West, Calhoun, GA (US); James L. Greene, Galway (IE)

(73) Assignee: APK Advanced Medical Technologies, Inc., Atlanta, GA (US)

(*) Notice: Subject to any disclaimer, the term of this patent is extended or adjusted under 35 U.S.C. 154(b) by 1138 days.

(21) Appl. No.: 14/854,340

(22) Filed: Sep. 15, 2015

(65) Prior Publication Data

US 2016/0067395 A1 Mar. 10, 2016

Related U.S. Application Data

(63) Continuation of application No. PCT/US2014/028346, filed on Mar. 14, 2014.

(Continued)

(51) Int. Cl.
*A61M 1/12* (2006.01)
*A61M 1/10* (2006.01)
(Continued)

(52) U.S. Cl.
CPC .............. *A61M 1/125* (2014.02); *A61M 1/10* (2013.01); *A61M 39/0247* (2013.01);
(Continued)

(58) Field of Classification Search
CPC ...... A61M 1/125; A61M 1/10; A61M 1/1008; A61M 1/1087; A61M 1/1096;
(Continued)

(56) References Cited

U.S. PATENT DOCUMENTS 3,512,519 A 5/1970 Hall
3,540,451 A 11/1970 Zeman
(Continued)

FOREIGN PATENT DOCUMENTS

CA 2526920 2/2009
CN 1842354 10/2006
(Continued)

OTHER PUBLICATIONS

PCT International Search Report and Written Opinion for PCT Application No. PCT/US014/028346 dated Aug. 7, 2014 (10 pages).

*Primary Examiner* — Katherine M Rodjom
(74) *Attorney, Agent, or Firm* — Eversheds Sutherland (US) LLP

(57) ABSTRACT

Embodiments of the present invention provide devices, systems, and methods for implanting and using a connector in a tissue wall to establish, maintain, control, and close a fluid communication between opposing surfaces of the tissue wall. The connector may include an anchoring device, a port, and a coupler device. The anchoring device may be configured for advancing at least partially through the tissue wall. The port may be positioned about a proximal end of the anchoring device, and the port may define an aperture therethrough. The coupler device may be positioned about a proximal end of the port, and the coupler device may be configured for coupling to a medical device.

19 Claims, 36 Drawing Sheets

Related U.S. Application Data

(60) Provisional application No. 61/793,643, filed on Mar. 15, 2013, provisional application No. 61/842,810, filed on Jul. 3, 2013, provisional application No. 61/859,608, filed on Jul. 29, 2013, provisional application No. 61/865,908, filed on Aug. 14, 2013.

(51) Int. Cl.
   *A61M 39/02* (2006.01)
   *A61M 39/10* (2006.01)
   *A61M 25/04* (2006.01)

(52) U.S. Cl.
   CPC ......... *A61M 39/1011* (2013.01); *A61M 1/101* (2013.01); *A61M 1/1008* (2014.02); *A61M 1/1087* (2014.02); *A61M 1/1096* (2014.02); *A61M 1/122* (2014.02); *A61M 25/04* (2013.01); *A61M 2039/0261* (2013.01); *A61M 2039/1027* (2013.01); *A61M 2039/1033* (2013.01)

(58) Field of Classification Search
   CPC .. A61M 1/122; A61M 1/101; A61M 39/0247; A61M 39/1011; A61M 25/04; A61M 2039/0261; A61M 2039/1027; A61M 2039/1033
   See application file for complete search history.

(56) References Cited

U.S. PATENT DOCUMENTS

| | | | |
|---|---|---|---|
| 3,856,021 A | 12/1974 | McIntosh | |
| 4,204,541 A | 5/1980 | Kapitanov | |
| 4,366,819 A | 1/1983 | Kaster | |
| 4,769,031 A | 9/1988 | McGough et al. | |
| 4,904,264 A | 2/1990 | Scheunemann | |
| 4,955,856 A | 9/1990 | Phillips | |
| 5,098,369 A | 3/1992 | Heilman et al. | |
| 5,129,913 A | 7/1992 | Ruppert | |
| 5,139,517 A | 8/1992 | Corral | |
| 5,158,563 A | 10/1992 | Cosman | |
| 5,222,980 A | 6/1993 | Gealow | |
| 5,256,160 A | 10/1993 | Clement | |
| 5,291,179 A | 3/1994 | Ooe et al. | |
| 5,387,193 A | 2/1995 | Miraki | |
| 5,447,533 A | 9/1995 | Vachon et al. | |
| 5,456,714 A | 10/1995 | Owen | |
| 5,562,729 A | 10/1996 | Purdy et al. | |
| 5,577,993 A | 11/1996 | Zhu et al. | |
| 5,582,616 A | 12/1996 | Bolduc et al. | |
| 5,695,504 A | 12/1997 | Gifford et al. | |
| 5,728,116 A | 3/1998 | Rosenman | |
| 5,738,680 A | 4/1998 | Mueller et al. | |
| 5,755,697 A | 5/1998 | Jones et al. | |
| 5,782,844 A | 7/1998 | Yoon et al. | |
| 5,797,933 A | 8/1998 | Snow et al. | |
| 5,810,836 A | 9/1998 | Hussein et al. | |
| 5,810,851 A | 9/1998 | Yoon | |
| 5,814,005 A | 9/1998 | Barra et al. | |
| 5,824,070 A | 10/1998 | Jarvik | |
| 5,824,071 A | 10/1998 | Nelson et al. | |
| 5,827,316 A | 10/1998 | Young et al. | |
| 5,833,698 A | 11/1998 | Hinchliffe et al. | |
| 5,843,088 A | 12/1998 | Barra et al. | |
| 5,865,791 A | 2/1999 | Whyane et al. | |
| 5,893,369 A | 4/1999 | LeMole | |
| 5,910,153 A | 6/1999 | Mayenberger | |
| 5,924,424 A | 7/1999 | Stevens et al. | |
| 5,944,730 A | 8/1999 | Nobles et al. | |
| 5,976,174 A | 11/1999 | Ruiz | |
| 5,984,956 A | 11/1999 | Tweden et al. | |
| 5,989,278 A | 11/1999 | Mueller | |
| 6,001,056 A | 12/1999 | Jassawalla et al. | |
| 6,007,576 A | 12/1999 | McClellan | |
| 6,022,324 A | 2/2000 | Skinner | |
| 6,022,367 A | 2/2000 | Sherts | |
| 6,024,755 A | 2/2000 | Addis | |
| 6,039,748 A | 3/2000 | Savage et al. | |
| 6,066,085 A | 5/2000 | Heilman et al. | |
| 6,079,414 A | 6/2000 | Roth | |
| 6,080,173 A | 6/2000 | Williamson, IV et al. | |
| 6,080,176 A | 6/2000 | Young | |
| 6,113,611 A | 9/2000 | Allen et al. | |
| 6,146,325 A | 11/2000 | Lewis et al. | |
| 6,210,397 B1 * | 4/2001 | Aboul-Hosn | A61B 17/3423 604/164.11 |
| 6,241,743 B1 | 6/2001 | Levin et al. | |
| 6,254,564 B1 | 7/2001 | Wilk et al. | |
| 6,267,732 B1 | 7/2001 | Heneveld et al. | |
| 6,273,862 B1 | 8/2001 | Privitera et al. | |
| 6,290,639 B1 | 9/2001 | Mussivand et al. | |
| 6,290,728 B1 | 9/2001 | Phelps et al. | |
| 6,346,071 B1 | 2/2002 | Mussivand | |
| 6,390,976 B1 | 5/2002 | Spence et al. | |
| 6,401,720 B1 | 6/2002 | Stevens et al. | |
| 6,409,739 B1 | 6/2002 | Nobles et al. | |
| 6,443,957 B1 | 9/2002 | Addis | |
| 6,458,140 B2 | 10/2002 | Akin et al. | |
| 6,506,197 B1 | 1/2003 | Rollero et al. | |
| 6,537,300 B2 | 3/2003 | Girton | |
| 6,551,319 B2 | 4/2003 | Lieberman | |
| 6,551,322 B1 | 4/2003 | Lieberman | |
| 6,551,332 B1 | 4/2003 | Nguyen et al. | |
| 6,589,277 B1 | 7/2003 | Fabiani et al. | |
| 6,607,541 B1 | 8/2003 | Gardiner et al. | |
| 6,638,237 B1 | 10/2003 | Guiles et al. | |
| 6,651,670 B2 | 11/2003 | Rapacki et al. | |
| 6,663,633 B1 | 12/2003 | Pierson, III | |
| 6,669,708 B1 | 12/2003 | Nissenbaum et al. | |
| 6,673,043 B1 | 1/2004 | Landesberg | |
| 6,676,678 B2 | 1/2004 | Gifford, III et al. | |
| 6,689,147 B1 | 2/2004 | Koster, Jr. | |
| 6,695,859 B1 | 2/2004 | Golden et al. | |
| 6,699,256 B1 | 3/2004 | Logan et al. | |
| 6,705,988 B2 | 3/2004 | Spence et al. | |
| 6,726,648 B2 | 4/2004 | Kaplon et al. | |
| 6,732,501 B2 | 5/2004 | Yu et al. | |
| 6,740,101 B2 | 5/2004 | Houser et al. | |
| 6,776,787 B2 | 8/2004 | Phung et al. | |
| 6,802,806 B2 | 10/2004 | McCarthy et al. | |
| 6,808,498 B2 | 10/2004 | Laroya et al. | |
| 6,824,071 B1 | 11/2004 | McMichael | |
| 6,827,683 B2 | 12/2004 | Otawara | |
| 6,863,677 B2 | 3/2005 | Breznock | |
| 6,869,437 B1 | 3/2005 | Hausen et al. | |
| 6,942,672 B2 | 9/2005 | Heilman et al. | |
| 6,978,176 B2 | 12/2005 | Lattouf | |
| 6,984,241 B2 | 1/2006 | Lubbers et al. | |
| 6,994,666 B2 | 2/2006 | Shannon et al. | |
| 7,018,384 B2 | 3/2006 | Skakoon | |
| 7,033,372 B1 | 4/2006 | Cahalan | |
| 7,048,681 B2 | 5/2006 | Tsubouchi et al. | |
| 7,056,286 B2 | 6/2006 | Ravenscroft et al. | |
| 7,077,801 B2 | 7/2006 | Haverich | |
| 7,083,631 B2 | 8/2006 | Houser et al. | |
| 7,163,525 B2 | 1/2007 | Franer | |
| 7,182,771 B1 | 2/2007 | Houser et al. | |
| 7,214,234 B2 | 5/2007 | Rapacki et al. | |
| 7,232,421 B1 | 6/2007 | Gambale et al. | |
| 7,258,694 B1 | 8/2007 | Choi et al. | |
| 7,309,343 B2 | 12/2007 | Vargas et al. | |
| 7,331,956 B2 | 2/2008 | Hovda et al. | |
| 7,404,792 B2 | 7/2008 | Spence et al. | |
| 7,510,561 B2 | 3/2009 | Beane et al. | |
| 7,637,919 B2 | 12/2009 | Ishikawa et al. | |
| 7,717,844 B2 | 5/2010 | Cohn | |
| 7,744,527 B2 | 6/2010 | Cohn | |
| 7,766,811 B2 | 8/2010 | Haverich | |
| 7,799,041 B2 | 9/2010 | Beane et al. | |
| 7,842,068 B2 | 11/2010 | Ginn | |
| 7,846,123 B2 | 12/2010 | Vassiliades et al. | |
| 7,846,179 B2 | 12/2010 | Belef et al. | |
| 7,931,581 B2 | 4/2011 | Cohn | |

(56) References Cited

U.S. PATENT DOCUMENTS

| | | |
|---|---|---|
| 7,942,805 B2 | 5/2011 | Shambaugh, Jr. |
| 7,993,392 B2 | 8/2011 | Righini et al. |
| 8,226,670 B2 | 7/2012 | Beane et al. |
| 8,430,836 B2 | 4/2013 | Vassiliades et al. |
| 8,556,930 B2 | 10/2013 | Ellingwood |
| 8,579,790 B2 | 11/2013 | Jeffery et al. |
| 8,764,795 B2 | 7/2014 | Whitman et al. |
| 8,840,538 B2 | 9/2014 | Jeffery et al. |
| 8,858,489 B2 | 10/2014 | Vassiliades et al. |
| 2001/0051809 A1 | 12/2001 | Houser et al. |
| 2002/0019623 A1 | 2/2002 | Altman et al. |
| 2002/0019643 A1 | 2/2002 | Gifford et al. |
| 2002/0032462 A1 | 3/2002 | Houser et al. |
| 2002/0038127 A1 | 3/2002 | Blatter et al. |
| 2002/0045846 A1 | 4/2002 | Kaplon et al. |
| 2002/0055737 A1 | 5/2002 | Lieberman |
| 2002/0055738 A1 | 5/2002 | Lieberman |
| 2002/0055739 A1 | 5/2002 | Lieberman |
| 2002/0055740 A1 | 5/2002 | Lieberman |
| 2002/0055742 A1 | 5/2002 | Lieberman |
| 2002/0058958 A1 | 5/2002 | Walen |
| 2002/0095210 A1 | 7/2002 | Finnegan et al. |
| 2002/0099394 A1 | 7/2002 | Houser et al. |
| 2002/0116018 A1 | 8/2002 | Stevens et al. |
| 2002/0177865 A1 | 11/2002 | McIntosh |
| 2002/0183786 A1 | 12/2002 | Girton |
| 2002/0193806 A1 | 12/2002 | Moenning et al. |
| 2003/0014064 A1 | 1/2003 | Blatter |
| 2003/0023255 A1 | 1/2003 | Miles et al. |
| 2003/0032979 A1 | 2/2003 | Mortier et al. |
| 2003/0040765 A1 | 2/2003 | Breznock |
| 2003/0045834 A1 | 3/2003 | Wing et al. |
| 2003/0078592 A1 | 4/2003 | Heilman et al. |
| 2003/0130668 A1 | 7/2003 | Nieman et al. |
| 2003/0181843 A1 | 9/2003 | Bibber et al. |
| 2003/0181913 A1 | 9/2003 | Lieberman |
| 2004/0002624 A1 | 1/2004 | Yu et al. |
| 2004/0050393 A1 | 3/2004 | Golden et al. |
| 2004/0068299 A1 | 4/2004 | Laske et al. |
| 2004/0073216 A1 | 4/2004 | Lieberman |
| 2004/0077989 A1 | 4/2004 | Goode et al. |
| 2004/0092858 A1 | 5/2004 | Wilson et al. |
| 2004/0097973 A1 | 5/2004 | Loshakove et al. |
| 2004/0097993 A1 | 5/2004 | Whayne |
| 2004/0098011 A1 | 5/2004 | Vargas et al. |
| 2004/0133155 A1 | 7/2004 | Varner et al. |
| 2004/0138702 A1 | 7/2004 | Peartree et al. |
| 2004/0153112 A1 | 8/2004 | Nissenbaum et al. |
| 2004/0158308 A1 | 8/2004 | Hogendijk et al. |
| 2004/0162608 A1 | 8/2004 | Haverich |
| 2004/0167547 A1 | 8/2004 | Beane et al. |
| 2004/0167551 A1 | 8/2004 | Gifford, III et al. |
| 2004/0171905 A1 | 9/2004 | Yu et al. |
| 2004/0186490 A1 | 9/2004 | Houser et al. |
| 2004/0225306 A1 | 11/2004 | Blatter et al. |
| 2004/0236170 A1 | 11/2004 | Kim |
| 2005/0033107 A1 | 2/2005 | Tsubouchi |
| 2005/0043781 A1 | 2/2005 | Foley |
| 2005/0075656 A1 | 4/2005 | Beaupre |
| 2005/0101982 A1 | 5/2005 | Ravenscroft et al. |
| 2005/0101983 A1 | 5/2005 | Loshakove et al. |
| 2005/0131451 A1 | 6/2005 | Kleshinski et al. |
| 2005/0137609 A1 | 6/2005 | Guiraudon |
| 2005/0149093 A1 | 7/2005 | Pokorney |
| 2005/0154411 A1 | 7/2005 | Breznock et al. |
| 2005/0171479 A1 | 8/2005 | Hruska et al. |
| 2005/0187568 A1 | 8/2005 | Klenk et al. |
| 2005/0192604 A1 | 9/2005 | Carson et al. |
| 2005/0209502 A1 | 9/2005 | Schmid et al. |
| 2005/0222582 A1 | 10/2005 | Wenchell |
| 2005/0251187 A1 | 11/2005 | Beane et al. |
| 2005/0256368 A1 | 11/2005 | Klenk et al. |
| 2005/0267495 A1 | 12/2005 | Ginn et al. |
| 2006/0020326 A9 | 1/2006 | Bolduc et al. |
| 2006/0036313 A1 | 2/2006 | Vassiliades et al. |
| 2006/0074484 A1 | 4/2006 | Huber |
| 2006/0089707 A1 | 4/2006 | Vassiliades et al. |
| 2006/0099716 A1 | 5/2006 | Tipler et al. |
| 2006/0142634 A1 | 6/2006 | Anstadt et al. |
| 2006/0161193 A1 | 7/2006 | Beane et al. |
| 2006/0167333 A1 | 7/2006 | Moore et al. |
| 2006/0178675 A1 | 8/2006 | Hamman |
| 2006/0241659 A1 | 10/2006 | Tulleken et al. |
| 2006/0259050 A1 | 11/2006 | DeWinter |
| 2007/0055357 A1 | 3/2007 | Pokorney et al. |
| 2007/0060952 A1 | 3/2007 | Roby et al. |
| 2007/0066943 A1 | 3/2007 | Prasad et al. |
| 2007/0088375 A1 | 4/2007 | Beane et al. |
| 2007/0100363 A1 | 5/2007 | Dollar et al. |
| 2007/0106315 A1 | 5/2007 | Gregoric et al. |
| 2007/0106328 A1 | 5/2007 | Wardle et al. |
| 2007/0112361 A1 | 5/2007 | Schonholz et al. |
| 2007/0167968 A1 | 7/2007 | Pandey |
| 2007/0167969 A1 | 7/2007 | Pandey |
| 2007/0173879 A1 | 7/2007 | Pandey |
| 2007/0197856 A1 | 8/2007 | Gellman et al. |
| 2007/0208214 A1 | 9/2007 | Hjelle et al. |
| 2007/0265643 A1 | 11/2007 | Beane et al. |
| 2008/0004640 A1 | 1/2008 | Ellingwood |
| 2008/0009668 A1 | 1/2008 | Cohn |
| 2008/0009887 A1 | 1/2008 | Cohn |
| 2008/0009891 A1 | 1/2008 | Cohn |
| 2008/0039883 A1 | 2/2008 | Nohilly |
| 2008/0058846 A1 | 3/2008 | Vosough |
| 2008/0076959 A1 | 3/2008 | Farnan et al. |
| 2008/0161826 A1 | 7/2008 | Guiraudon |
| 2008/0177301 A1 | 7/2008 | Svensson |
| 2008/0255597 A1 | 10/2008 | Pravong et al. |
| 2009/0012552 A1 | 1/2009 | Pandey et al. |
| 2009/0082778 A1 | 3/2009 | Beane et al. |
| 2009/0112062 A1 | 4/2009 | Bakos |
| 2009/0203957 A1 | 8/2009 | LaRose et al. |
| 2009/0204206 A1 | 8/2009 | Parquet et al. |
| 2009/0240264 A1 | 9/2009 | Tuval et al. |
| 2010/0004739 A1 | 1/2010 | Vesely |
| 2010/0010500 A1 | 1/2010 | Beane et al. |
| 2010/0010616 A1 | 1/2010 | Drews et al. |
| 2010/0049225 A1 | 2/2010 | To et al. |
| 2010/0087907 A1 | 4/2010 | Lattouf |
| 2010/0160847 A1 | 6/2010 | Braido et al. |
| 2010/0161040 A1 | 6/2010 | Braido et al. |
| 2010/0168778 A1 | 7/2010 | Braido |
| 2011/0028985 A1* | 2/2011 | Vassiliades ...... A61B 17/32053 606/108 |
| 2011/0092761 A1 | 4/2011 | Almog et al. |
| 2011/0106116 A1 | 5/2011 | Ducharme et al. |
| 2011/0118766 A1 | 5/2011 | Reichenbach et al. |
| 2011/0118770 A1 | 5/2011 | Pokorney et al. |
| 2011/0118833 A1 | 5/2011 | Reichenbach et al. |
| 2011/0144680 A1 | 6/2011 | Nguyen et al. |
| 2011/0160850 A1 | 6/2011 | Bourque |
| 2011/0190811 A1 | 8/2011 | Shanley |
| 2011/0196190 A1 | 8/2011 | Farnan et al. |
| 2011/0224785 A1 | 9/2011 | Hacohen |
| 2011/0251450 A1 | 10/2011 | Pagani et al. |
| 2012/0059212 A1 | 3/2012 | LaRose et al. |
| 2012/0059457 A1 | 3/2012 | Leinsing et al. |
| 2012/0089181 A1 | 4/2012 | Shanley et al. |
| 2012/0123452 A1 | 5/2012 | Asfora et al. |
| 2012/0123461 A1 | 5/2012 | Gillies et al. |
| 2012/0226096 A1 | 9/2012 | Callaway et al. |
| 2012/0253386 A1 | 10/2012 | Rowe et al. |
| 2012/0296151 A1 | 11/2012 | Curtis et al. |
| 2012/0296358 A1 | 11/2012 | Nguyen et al. |
| 2013/0012761 A1 | 1/2013 | Gregoric et al. |
| 2013/0110228 A1 | 5/2013 | Braido |
| 2013/0116728 A1 | 5/2013 | Litvack et al. |
| 2013/0150654 A1 | 6/2013 | Stanfield et al. |
| 2013/0218169 A1 | 8/2013 | Vassiliades et al. |
| 2013/0253641 A1 | 9/2013 | Lattouf |
| 2014/0039375 A1 | 2/2014 | Jimenez et al. |
| 2014/0067057 A1 | 3/2014 | Callaway et al. |
| 2014/0100430 A1 | 4/2014 | Beane et al. |
| 2014/0148786 A1 | 5/2014 | Milo |

(56) References Cited

U.S. PATENT DOCUMENTS

| | | |
|---|---|---|
| 2014/0194833 A1 | 7/2014 | Andrus |
| 2014/0214159 A1 | 7/2014 | Vidlund et al. |
| 2014/0378772 A1 | 12/2014 | Sundt, III et al. |
| 2014/0379074 A1 | 12/2014 | Spence et al. |
| 2015/0032153 A1 | 1/2015 | Quadri et al. |
| 2015/0038770 A1 | 2/2015 | Colella |
| 2015/0112120 A1 | 4/2015 | Andrus |
| 2015/0196321 A1 | 7/2015 | Gregory et al. |
| 2015/0359952 A1 | 12/2015 | Andrus et al. |
| 2016/0095705 A1 | 4/2016 | Keranen et al. |

FOREIGN PATENT DOCUMENTS

| | | |
|---|---|---|
| EP | 1 669 042 | 6/2006 |
| EP | 1 706 168 | 10/2006 |
| EP | 1 691 884 | 3/2011 |
| EP | 1 628 702 | 5/2013 |
| JP | 09-47457 | 2/1997 |
| JP | 11-500642 | 1/1999 |
| JP | 2002-518082 | 6/2002 |
| JP | 2006-518624 | 8/2006 |
| JP | 2007-510522 | 4/2007 |
| WO | 93/25148 | 12/1993 |
| WO | 96/25886 | 8/1996 |
| WO | 97/13463 | 4/1997 |
| WO | 99/65409 | 12/1999 |
| WO | 00/00193 | 1/2000 |
| WO | 00/15147 | 3/2000 |
| WO | 00/15149 | 3/2000 |
| WO | 00/41759 | 7/2000 |
| WO | 2000/074747 | 12/2000 |
| WO | 2003/001980 | 1/2003 |
| WO | 2004/026147 | 4/2004 |
| WO | 2004/096059 | 11/2004 |
| WO | 2005/046783 | 5/2005 |
| WO | 2006/019755 | 2/2006 |
| WO | 2006/020651 | 2/2006 |
| WO | 2006/093970 | 9/2006 |
| WO | 2007/038109 | 4/2007 |
| WO | 2007/047212 | 4/2007 |
| WO | 2007/047933 | 4/2007 |
| WO | 2007/117612 | 10/2007 |
| WO | 2008/131453 | 10/2008 |
| WO | 2008/153872 | 12/2008 |
| WO | 2009/100198 | 8/2009 |
| WO | 2009/117435 | 9/2009 |
| WO | 2012/025927 | 3/2012 |
| WO | 2012/040233 | 3/2012 |
| WO | 2012/103546 | 8/2012 |
| WO | 2012/106422 | 8/2012 |
| WO | 2013/064529 | 5/2013 |
| WO | 2013189620 | 12/2013 |
| WO | 2015109328 | 7/2015 |

* cited by examiner

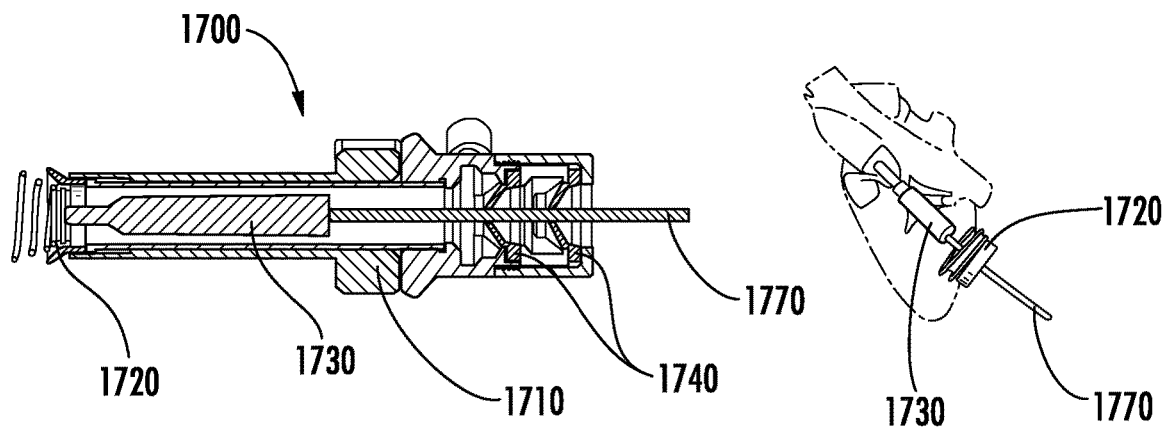
FIG. 15A
FIG. 15B
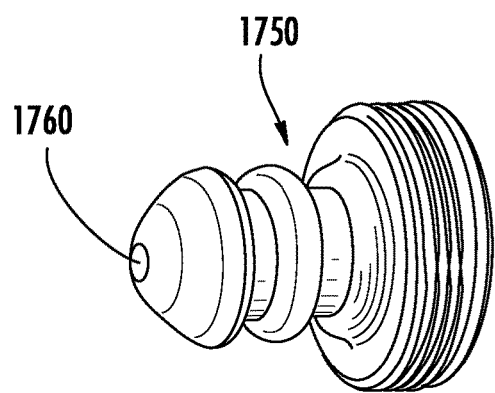
FIG. 15C
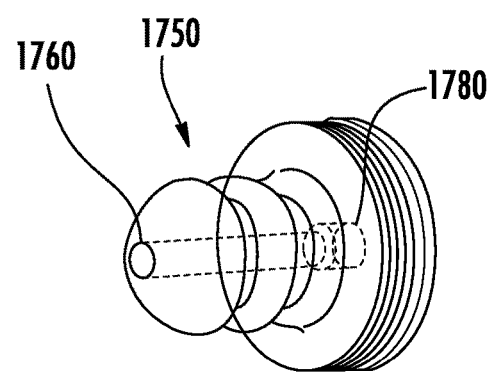
FIG. 15D

DEVICES, SYSTEMS, AND METHODS FOR IMPLANTING AND USING A CONNECTOR IN A TISSUE WALL

CROSS REFERENCES TO RELATED APPLICATIONS

This application is a continuation of PCT Application No. PCT/US2014/028346 filed Mar. 14, 2014 which claims priority to U.S. Provisional Application Ser. No. 61/793,643 filed Mar. 15, 2013, 61/842,810 filed Jul. 3, 2013, 61/859,608 filed Jul. 29, 2013, and 61/865,908 filed Aug. 14, 2013, the entire contents of which are incorporated by reference herewith.

FIELD OF THE INVENTION

The present invention relates to devices, systems, and methods for implanting and using a connector in a tissue wall to establish, maintain, control, and close a fluid communication between opposing surfaces of the tissue wall.

BACKGROUND OF THE INVENTION

In the human body, various organs contain fluids both in liquid and gaseous forms within tissue layers or cavities formed by tissue. These liquids may or may not be contained under pressure. The tissue walls around these cavities are normally designed to confine these liquids to specific areas of the body. Blood as in the heart and vasculature in order to preserve its volume and transport oxygen to tissue, gastric and intestinal fluids as in the stomach and intestines in order to transport remains of digestion out of the body after nutrients are absorbed, urine in the bladder in order to expel liquid waste from the body, fluid within the eye to maintain its shape and passage of light, are examples of such tissue fluid-confining systems. During medical procedures within these cavities it is of extreme importance to control the fluid within. The most common example is cardiopulmonary bypass during open heart surgery, although, in all procedures associated with the systems above emphasis is placed on control of the fluid within these cavities or organs. For this control, extra space often is required to conduct these interventions; therefore, highly invasive procedures may be required for surgery within these cavities, especially while maintaining organ function. The most complex example of these interventions is beating heart surgery, involving procedures that are conducted "off pump." For less invasive procedures, especially those within the vascular system, access ports or conduits which allow for fluid communication, control, and tissue closure within the organ being repaired are therefore required.

Because of the importance of heart function and the complexities associated with this pressurized system, some of the most complex procedures associated with bodily fluids are performed on this organ. Several of these procedures would benefit from an access port or conduit that can be connected to the heart while maintaining a fluid tight seal with tissue surfaces.

One procedure that would benefit from an improved fluid tight access port or conduit into the heart would be the implantation of a ventricular assist device (VAD), such as a left ventricular assist device (LVAD) between the left ventricle and the aorta, or a right ventricular assist device (RVAD) between the right ventricle and the pulmonary artery. The LVAD includes a mechanical pump that assists a failing heart by circulating blood through an alternative conduit from the left ventricle to the aorta. According to current techniques for LVAD implantation, which typically are performed on-pump, a hole is formed in the apex of the left ventricle and a conduit is secured within the hole via sutures. The RVAD similarly includes a mechanical pump that assists a failing heart by circulating blood through an alternative conduit from the right ventricle to the pulmonary artery. RVAD implantation techniques, which also tend to be performed on-pump, involve forming a hole in the lateral wall of the right ventricle and securing a conduit within the hole via sutures. After establishing a fluid tight connection between the conduit and the ventricular wall, an inlet tube of the VAD is attached to the conduit, which allows blood to flow from the ventricle to the pump. Due to the substantial risks of cardiopulmonary bypass, particularly for patients with advanced heart failure, it would be highly desirable to implant the VAD during an off-pump procedure. However, due to challenges in forming a hole in the ventricle of an active heart and then securely suturing a traditional conduit in place, on-pump techniques remain the standard for VAD implantation.

Another procedure that would benefit from an improved fluid tight access port or conduit into the heart would be heart valve replacement, which is the most common open heart cardiovascular surgery procedure. Currently, most heart valve repair or replacement surgeries are conducted on a heart at rest under cardiopulmonary bypass through a large median sternotomy. This surgery is highly invasive, and therefore, the population that may survive such a procedure is limited to those who are strong surgical candidates. In recent years, valves for minimally invasive deployment through the femoral artery or apex of the heart have been developed. These valves may be used in patients that would under other conditions be deemed non-candidates. The use of these valves may also in the future reduce complications associated with cardiopulmonary bypass and large incisions in surgical candidates. For those procedures through the apex of the heart, it has been shown that bleeding complications are directly associated with 50% increased mortality, and thus an access port or conduit that would reduce bleeding complications, decrease incision size, and simplify closure would be of great benefit.

Yet another procedure that would benefit from an improved fluid tight access port or conduit into the heart would be the construction of an alternative conduit between the left ventricle and the aorta (an apicoaortic conduit, or AAC). This procedure creates a double-outlet left ventricle (LV) to treat a variety of complex congenital LV outflow obstruction (fibrous tunnel obstruction, aortic annular hypoplasia, tubular hypoplasia of the ascending aorta, and patients with diffuse septal thickening, severe LV hypertrophy, and a small LV cavity) as well as adult-onset aortic stenosis in patients with complicating preoperative conditions (previous failed annular augmentation procedures, previous infection, previous CABG with patent anterior internal mammary artery grafts, and a porcelain ascending aorta). However, the AAC insertion procedure has been poorly accepted, with or without cardiopulmonary bypass, and has not been as technically straightforward as direct aortic valve replacement. Nonetheless, several studies have demonstrated that AAC insertion successfully lessens the LV-aortic pressure gradient, preserves or improves ventricular function, and maintains normally distributed blood flow through the systemic and coronary circulation.

While there have been several techniques described, the most commonly employed method is the lateral thoracotomy approach with placement of the AAC to the descending aorta or a median sternotomy. The current techniques and technology available to perform AAC insertion were originally designed to be performed on-pump, either with an arrested or fibrillating heart, and are therefore, highly invasive. Although off-pump cases have been described, they can be technically difficult due to the shortcomings of presently available conduits and systems for installing such conduits. For example, because existing conduits require the use of sutures to reliably secure the conduits in place, it is often difficult for surgeons or other clinicians to insert such sutures reliably in active cardiac and/or vascular tissue.

The various devices and systems described herein may be utilized as an accompaniment with any number of surgical procedures to gain access through a variety of possible tissues. For example, the devices and systems may be utilized to provide fluid access across a tissue wall for various procedures, such as, but not limited to, implantation of a VAD, establishing an AAC, establishing a port for inter-ventricular repairs (e.g., valve repair, valve replacement, or ablation procedures, etc.), establishing valved and/or open conduits (including bypass conduits) to augment native blood vessels in order to treat a variety of vascular conditions (e.g., aortic valvular disease, congestive heart failure, left ventricle outflow tract obstructions (LVOTO), peripheral arterial obstructions, small vessel obstructions, etc.), providing a conduit across a urinary bladder wall, providing a conduit across a gall bladder wall, providing a conduit into a thoracic cavity, providing a conduit into an abdominal cavity, providing a conduit into a cecal cavity, providing access into the cornea or eye walls, or providing access across or into any other tissue wall structures. Accordingly, the devices and systems described herein may be utilized with any of the aforementioned procedures and/or to gain access through any of the aforementioned tissue walls.

Certain related devices, systems, and methods have been previously described, such as those described in U.S. Pat. No. 7,846,123, PCT Patent Publication WO 2012/103546, and PCT Patent Publication WO 2012/106422, which are hereby incorporated by reference herein in their entirety. However, improved devices, systems, and methods for implanting and using a connector in a tissue wall are desirable, which may be used to establish, maintain, control, and close a fluid communication between opposing surfaces of the tissue wall.

SUMMARY OF THE INVENTION

Various embodiments of the present invention provide improved devices, systems, and methods for implanting and using a connector in a tissue wall to establish, maintain, control, and close a fluid communication between opposing surfaces of the tissue wall. Accordingly, such devices, systems, and methods may allow for implanting and using the connector in various tissue walls, including those of the heart, the stomach, or the bladder, to access various cavities defined therein. In certain applications, embodiments of the devices, systems, and methods may significantly simplify the in vivo beating heart treatment of cardiac patients. For example, embodiments of the devices, systems, and methods described herein may allow for implanting and using the connector in the beating cardiac apex, in areas near the apex including the fat-free brown patch on the anterolateral side of the apex, in the lateral wall of the right ventricle, or in other tissue walls (such as other areas of the heart including the anterior, lateral, posterior walls of the left or right ventricle, the left or right atrium, the aortic wall, ascending, transverse, or descending, or other blood vessel walls), such that it may effectively reduce and/or negate the detrimental effects of both cardio-pulmonary by-pass (CPB) and global cardiac ischemia. In this manner, the connector may be used as a fluid-tight access port for implantation of a VAD. Alternatively, the connector may be used as a fluid-tight access port for construction of an AAC. Further, the connector may be used as a fluid-tight access port for intravascular and intracardiac procedures such as heart valve repair or replacement.

In one embodiment of the present invention, a connector is provided for implanting in a tissue wall to establish, maintain, control, and close a fluid communication between opposing surfaces of the tissue wall. Specifically, the connector may be utilized as a heart connector configured for use in various cardiac procedures, including, but not limited to implantation of a VAD. The connector may include an anchoring device, a port, and a coupler device. The anchoring device may be configured for advancing at least partially through the tissue wall. The port may be positioned about a proximal end of the anchoring device, and the port may define an aperture therethrough. The coupler device may be positioned about the port, and the coupler device may be configured for coupling to a medical device.

The anchoring device may be a suture-less device configured for advancing at least partially through the tissue wall. In some aspects, the anchoring device may include a helical coil or spring. The helical coil or spring may include a radially-expanding helical coil or spring such that a helical diameter of the coil or spring increases from a proximal end of the anchoring device toward a distal end of the anchoring device. Alternatively, the helical coil or spring may include a straight helical coil or spring such that a helical diameter of the coil or spring is substantially constant from a proximal end of the anchoring device to a distal end of the anchoring device. In other aspects, the anchoring device may include a plurality of pins, prongs, barbs, or hooks. In some aspects, the anchoring device may be configured for compressing at least a portion of the tissue wall inward toward an axis of the anchoring device when advanced at least partially therethrough.

In certain aspects, the port may be formed as a substantially ring-shaped member. The port may include a flange formed about a distal end of the port, and the flange may be configured for contacting the tissue wall upon advancing the anchoring device at least partially therethrough. The port also may include tool attachment features configured for attaching various tools to the connector.

In some aspects, the coupler device may be a suture-less device configured for coupling to the medical device. The coupler device may be configured for receiving and axially retaining the medical device. The coupler device also may be configured for preventing axial rotation of the medical device. The coupler device may be configured for locking onto a smooth outer surface of the medical device. The medical device may be an inlet tube of a ventricular assist device, and the coupler device may be configured for receiving and retaining the inlet tube. The coupler device may be configured for locking onto a smooth outer surface of the inlet tube. In certain aspects, the coupler device may include a deflection arm mechanism configured for receiving and axially retaining the medical device. The deflection arm mechanism also may be configured for preventing axial rotation of the medical device. The deflection arm mechanism may include a deflection arm configured for deflecting inward into an aperture of the coupler device and retaining the medical device. In other aspects, the coupler device may include a taper lock mechanism configured for receiving and retaining the medical device. In some aspects, the coupler device may include an axial clip mechanism configured for receiving and retaining the medical device. In other aspects, the coupler device may include a worm gear collet mechanism configured for receiving and retaining the medical device. In still other aspects, the coupler device may include a hinged ring lock mechanism configured for receiving and retaining the medical device. In other aspects, the coupler device may include an axial clip and clamp mechanism configured for receiving and retaining the medical device. In certain aspects, the coupler device may include a universal coupler device configured for receiving and axially retaining an inlet tube having an outer diameter within a selected range. In some such aspects, the outer diameter may be between 15 mm and 30 mm. In other such aspects, the outer diameter may be between 19 mm and 22 mm.

In certain aspects, the connector may further include a secondary sealing element configured for contacting and sealing against the tissue wall upon advancing the anchoring device at least partially therethrough. The secondary sealing element may be formed as a substantially ring-shaped member positioned about the distal end of the port. In some aspects, the secondary sealing member may have a generally frusto-conical shape. In other aspects, the secondary sealing member may have a generally flat annular shape. The secondary sealing member may be formed of a rigid or substantially rigid material configured for biasing the tissue wall to conform to the geometry of the secondary sealing element. Alternatively, the secondary sealing member may be formed of a flexible or elastic material configured for conforming to the shape of the tissue wall.

In some aspects, the connector may further include a hemostasis valve configured for closing a fluid communication through the connector. The hemostasis valve may be positioned at least partially within the aperture of the port, and the hemostasis valve may be configured for closing the fluid communication through the aperture. The hemostasis valve may be formed as a one-way valve. Specifically, the hemostasis valve may be formed as a one-way multi-leaflet valve. Alternatively, the hemostasis valve may be formed as a tubular membrane. In some aspects, the hemostasis valve may be configured for allowing at least a portion of the medical device to pass therethrough. In some such aspects, the hemostasis valve may be configured for forming a fluid-tight seal about an outer surface of the medical device.

In some aspects, the connector may further include a cannula configured for positioning at least partially through the aperture of the port and at least partially through the tissue wall. The cannula may include threads configured for engaging mating threads of the port. The connector may include a hemostasis valve positioned at least partially within the cannula and configured for closing a fluid communication through the connector.

In certain aspects, the connector may include one or more de-airing orifices configured for de-airing a cavity defined by the tissue wall, such as a ventricle defined by a heart tissue wall. The de-airing orifices may be defined in the hemostasis valve of the connector. Specifically, the de-airing orifices may be defined in the base of one or more valve leaflets at a proximal end of the valve. Alternatively, the de-airing orifices may be defined between the valve leaflets. In some aspects, the de-airing orifices may be defined in the port or in the cannula of the connector. The de-airing orifices also may be configured for allowing the passage of a small amount of fluid contained within the cavity. In certain aspects including the de-airing orifices defined in the hemostasis valve, the hemostasis valve may include flaps positioned adjacent the de-airing orifices and configured for re-directing the flow of fluid onto proximal surfaces of the hemostasis valve.

In some aspects, the connector may include a rotation element configured for allowing the medical device, such as a VAD inlet tube, to rotate relative to the anchoring device and/or the port of the connector in a manner that changes an angle of incidence of the medical device with respect to the tissue wall. The rotation element may be a rotation knee-type joint. In some aspects, the rotation element may be positioned between the port and the cannula. Alternatively, the rotation element may be positioned between the cannula and the medical device. In certain aspects, the connector may also include a locking mechanism for retaining the angular position of the medical device relative to the anchoring device and/or the port.

In one embodiment of the present invention, a cutting tool is provided for forming a hole in a tissue wall. The cutting tool may include a piercing device and a coring device. The piercing device may include a piercing element configured for piercing the tissue wall and advancing therethrough. The piercing device may also include an expandable element positioned adjacent the piercing element and configured for expanding from a laterally contracted state to a laterally expanded state. The coring device may include a coring tube configured for removably receiving the piercing element and the expanding element therein. The expandable element and the coring tube may be configured to form the hole in the tissue wall by removing a tissue core therefrom. In some aspects, the expandable element may include a plurality of plates configured for moving from an axial position to a lateral position. In certain aspects, the piercing device and the coring device may be configured for translating axially with respect to one another.

In one embodiment of the present invention, an intra-cardiac circulatory support system is provided. The system may include a valved port, an anchoring device, and an intra-ventricular VAD. The valved port and the anchoring device may be configured for delivering the intra-ventricular VAD into a ventricle of a heart, and the anchoring device may be configured for maintaining the intra-ventricular VAD therein for treatment of a patient. The valved port may be removably attached to a proximal end of the anchoring device and configured for receiving the intra-ventricular VAD therein. In some aspects, the system may also include a closure element configured for occluding or closing fluid communication through the heart tissue wall. The closure element may include a pass-through orifice configured for allowing passage of a catheter, cables, or other elements that may need to be externalized through the heart tissue wall. The closure element also may include a hemostasis element configured for sealing around the catheter, cables or other externalized elements.

These and other features and improvements of embodiments of the present invention will become apparent to one of ordinary skill in the art upon review of the following detailed description when taken in conjunction with the several drawings and the appended claims.

BRIEF DESCRIPTION OF THE DRAWINGS

Figure 1A:
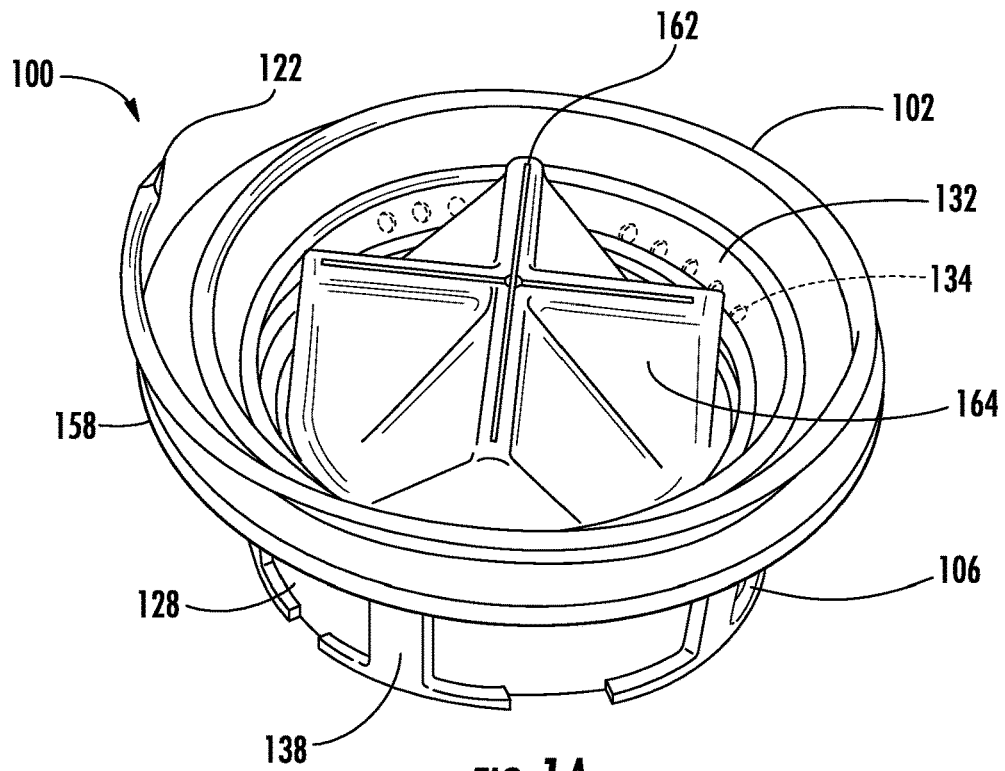

Having thus described various embodiments of the present invention in general terms, reference will now be made to the accompanying drawings, which are not necessarily drawn to scale, and wherein:

FIG. 1A shows a non-limiting perspective view of an exemplary connector for implanting and using in a tissue wall, in accordance with one embodiment of the present invention as may be described herein.

Figure 1B:
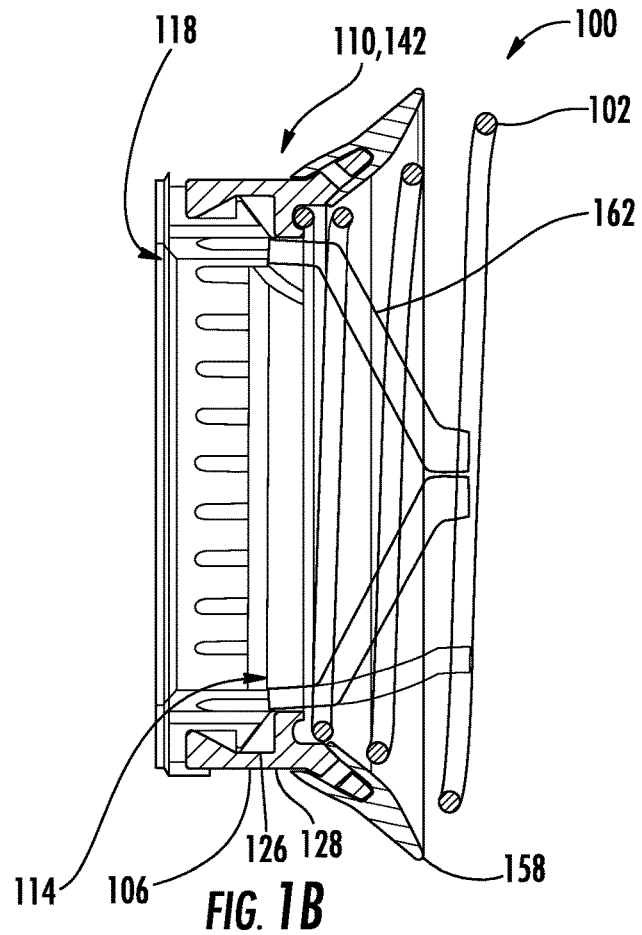

FIG. 1B shows a non-limiting side cross-sectional view of the connector of FIG. 1A.

Figure 1C:
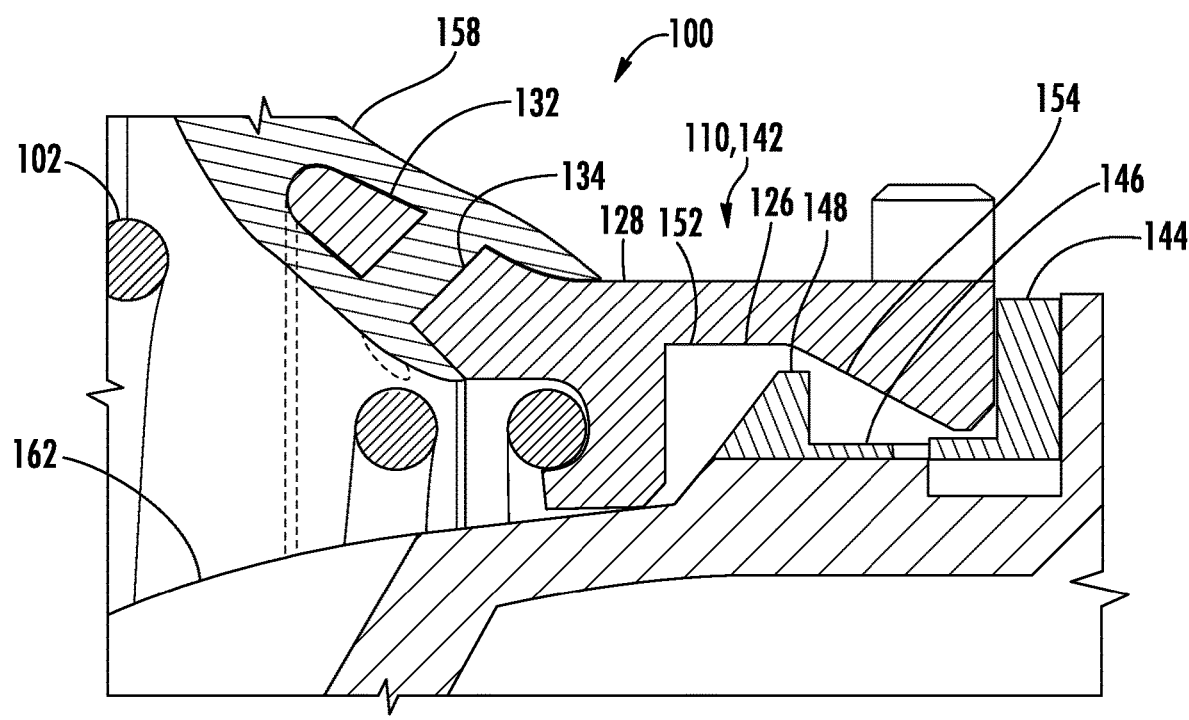

FIG. 1C shows a non-limiting side cross-sectional view of a taper lock mechanism of the connector of FIG. 1A.

Figure 1D:
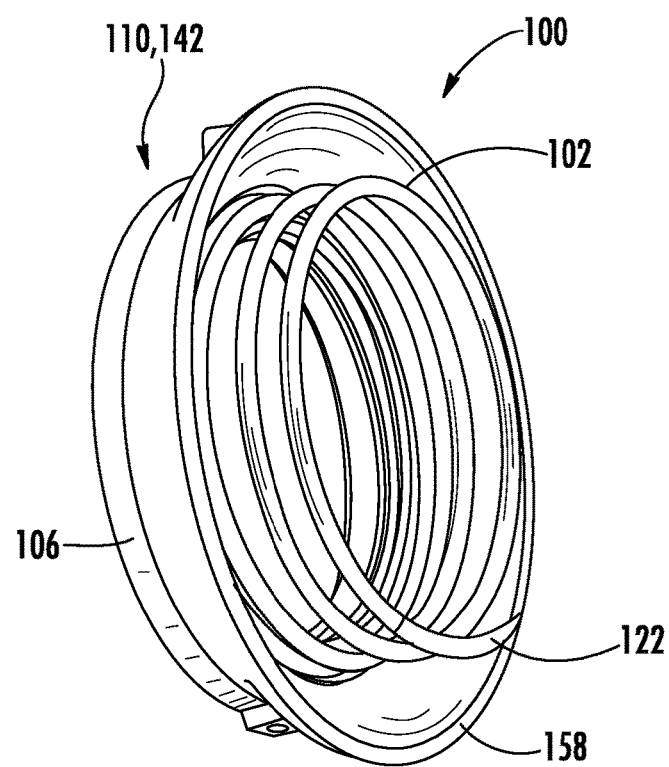

FIG. 1D shows a non-limiting perspective view of an exemplary connector for implanting and using in a tissue wall, in accordance with one embodiment of the present invention as may be described herein.

Figure 1E:
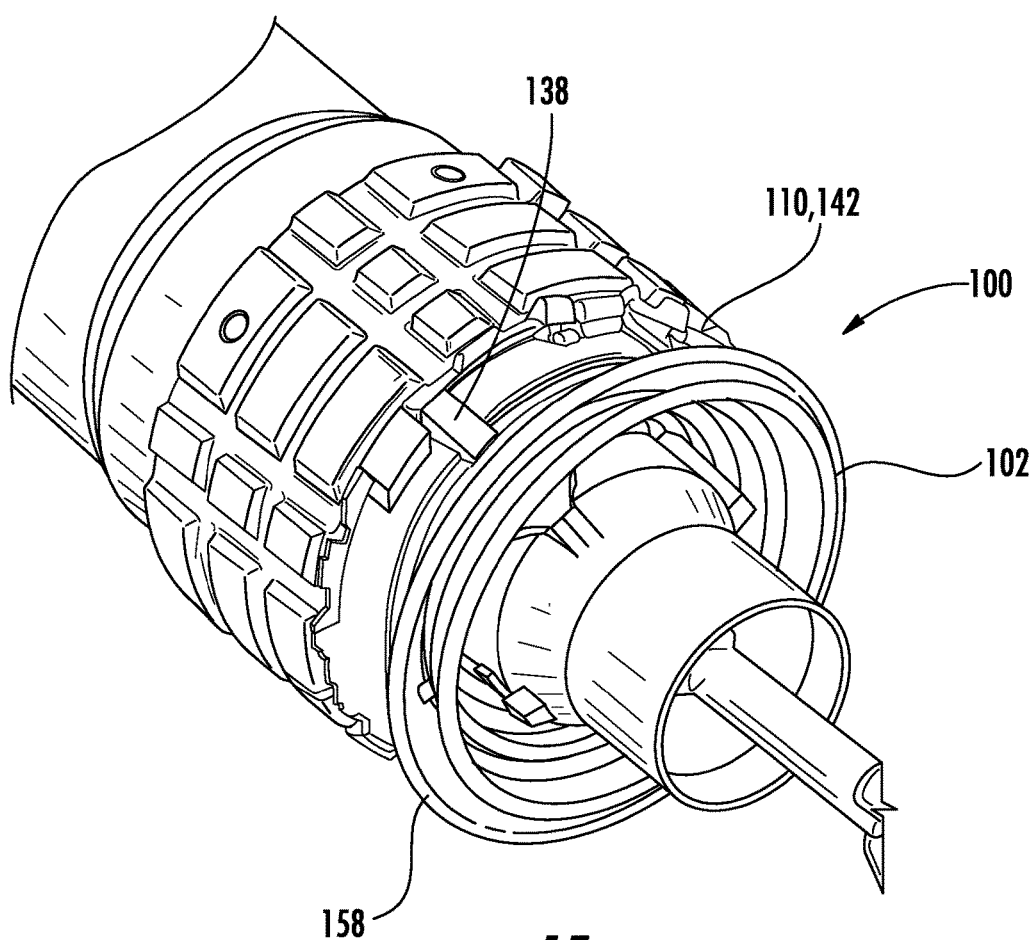

FIG. 1E shows a non-limiting perspective view of the connector of FIG. 1A attached to a tool.

Figure 1F:
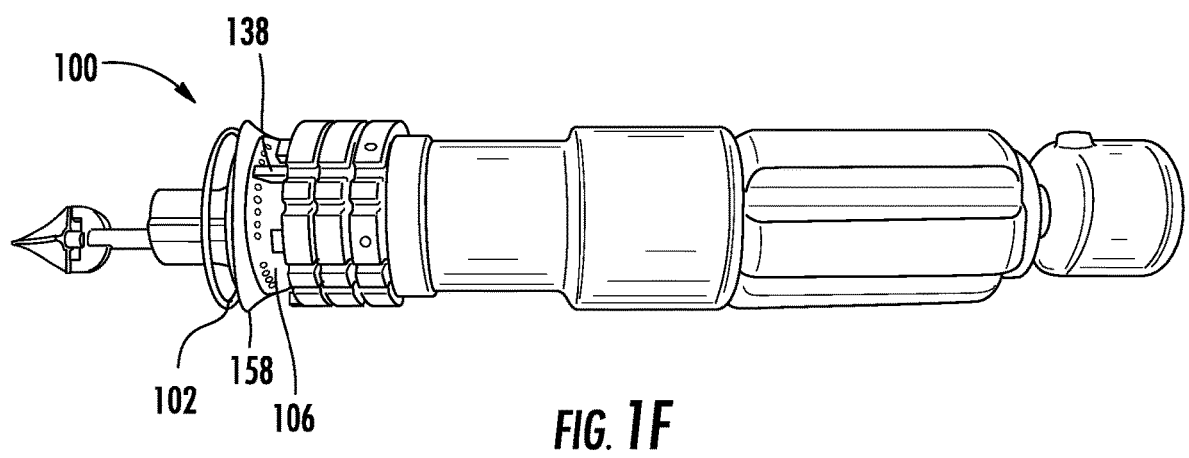

FIG. 1F shows a non-limiting perspective view of the connector of FIG. 1A attached to a tool.

Figure 2A:
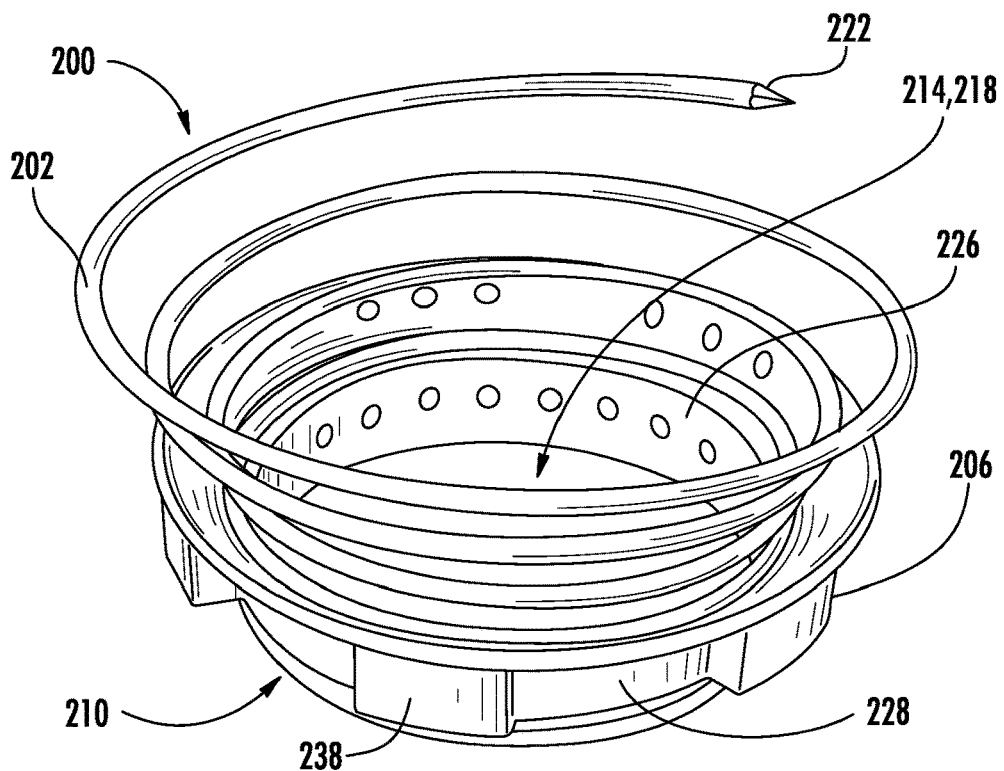

FIG. 2A shows a non-limiting perspective view of an exemplary connector for implanting and using in a tissue wall, in accordance with one embodiment of the present invention as may be described herein.

Figure 2B:
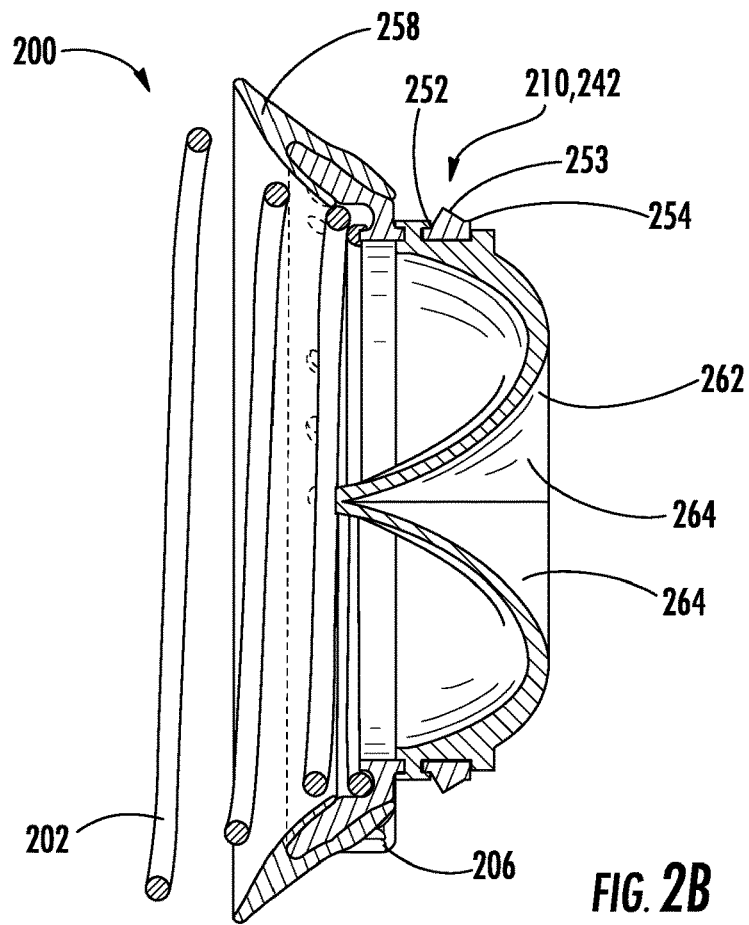

FIG. 2B shows a non-limiting side cross-sectional view of the connector of FIG. 2A.

Figure 2C:
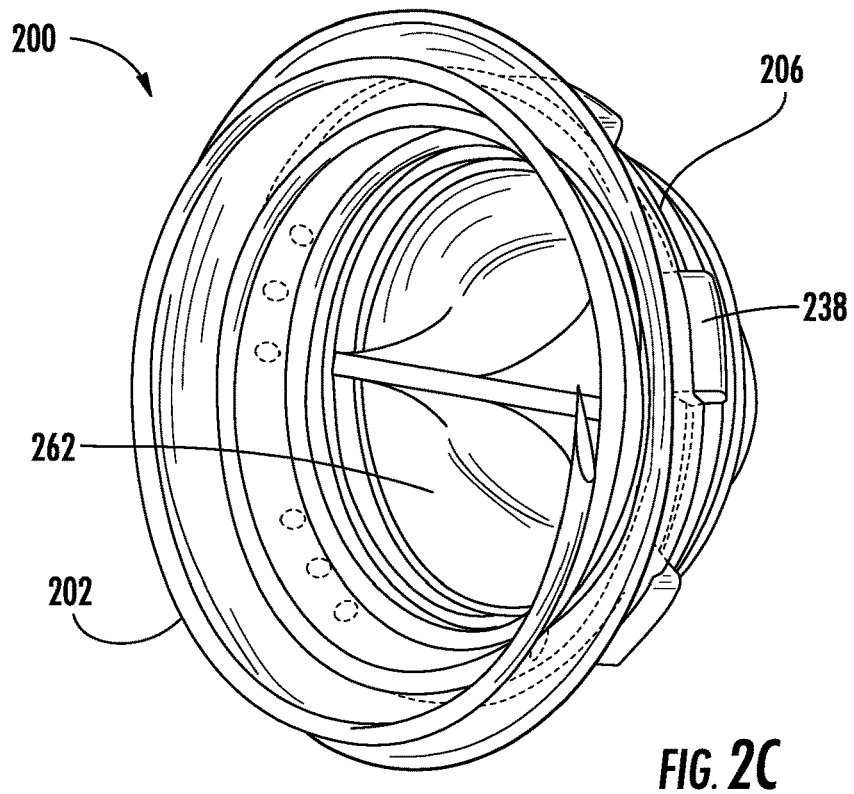

FIG. 2C shows a non-limiting side perspective view of the connector of FIG. 2A.

Figure 2D:
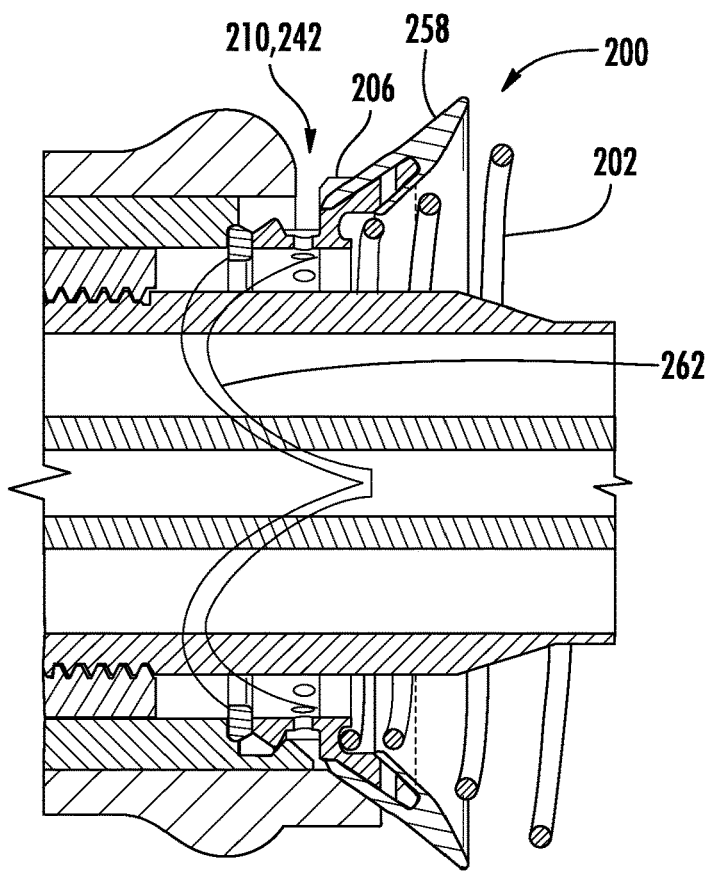

FIG. 2D shows a non-limiting perspective view of the connector of FIG. 2A attached to a tool.

Figure 2E:
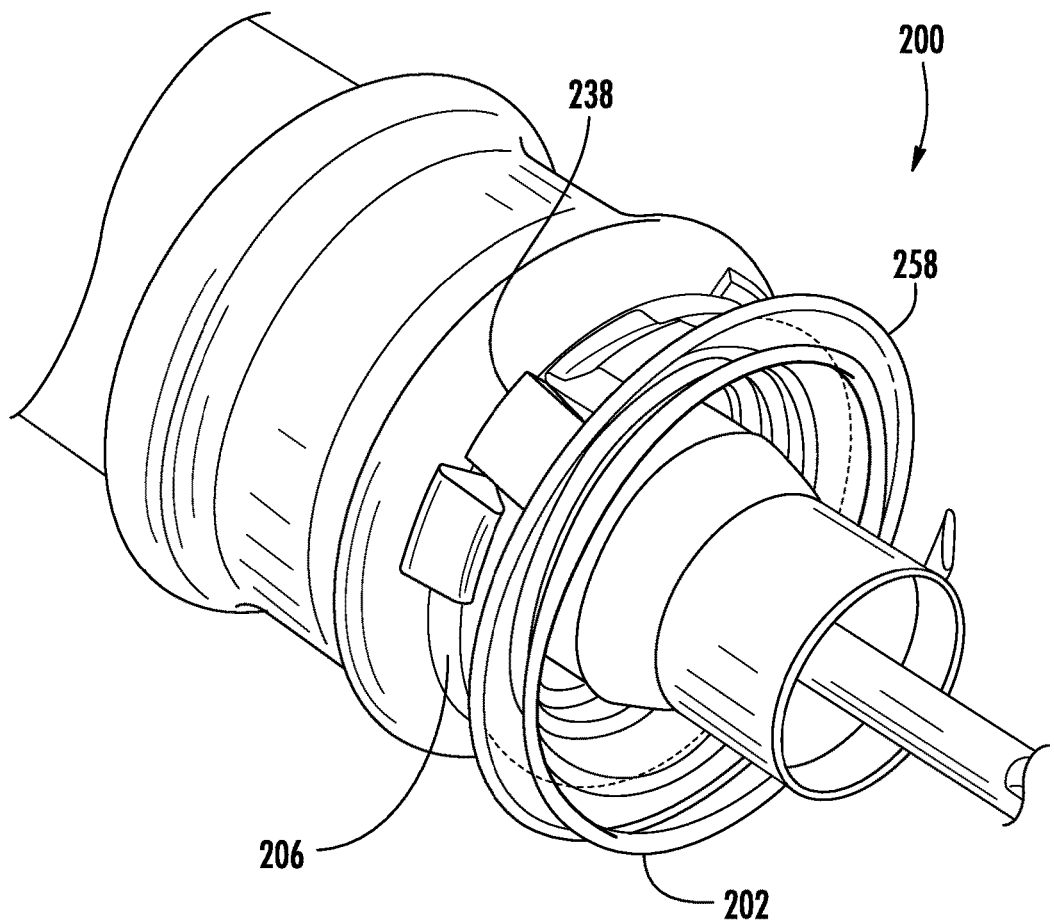
Figure 2F:
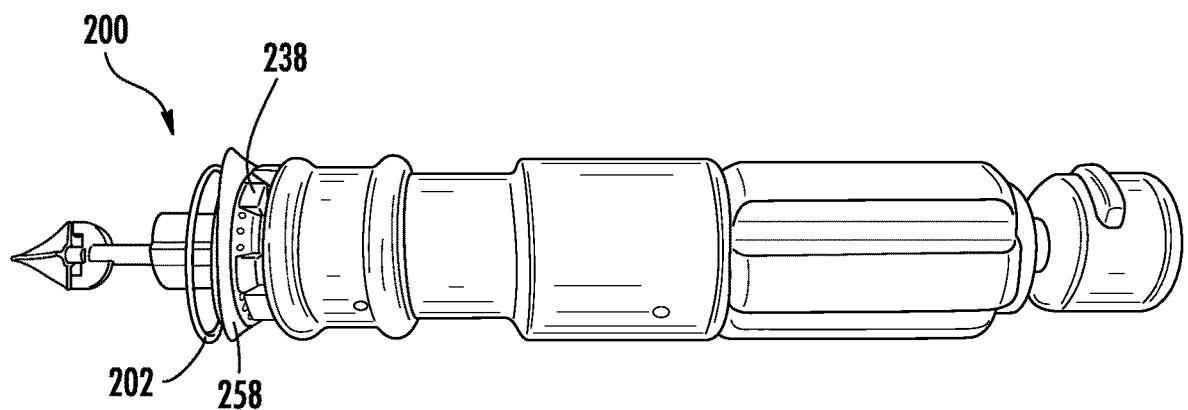

FIG. 2E shows a non-limiting perspective view of the connector of FIG. 2A attached to a tool. FIG. 2F shows a non-limiting perspective view of the connector of FIG. 2A attached to a tool.

Figure 2G:
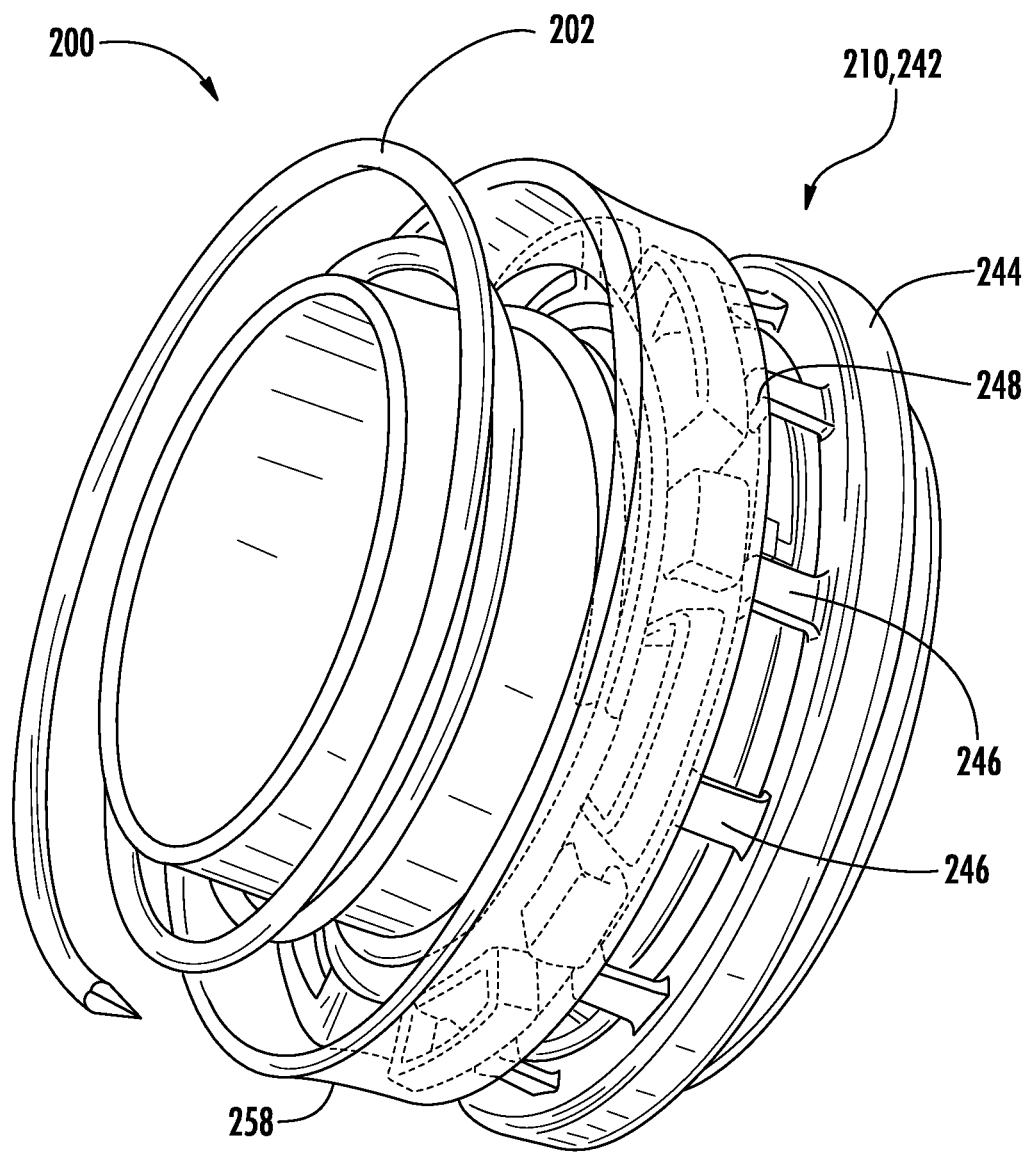

FIG. 2G shows a non-limiting perspective view of an exemplary connector for implanting and using in a tissue wall, in accordance with one embodiment of the present invention as may be described herein.

Figure 3A:
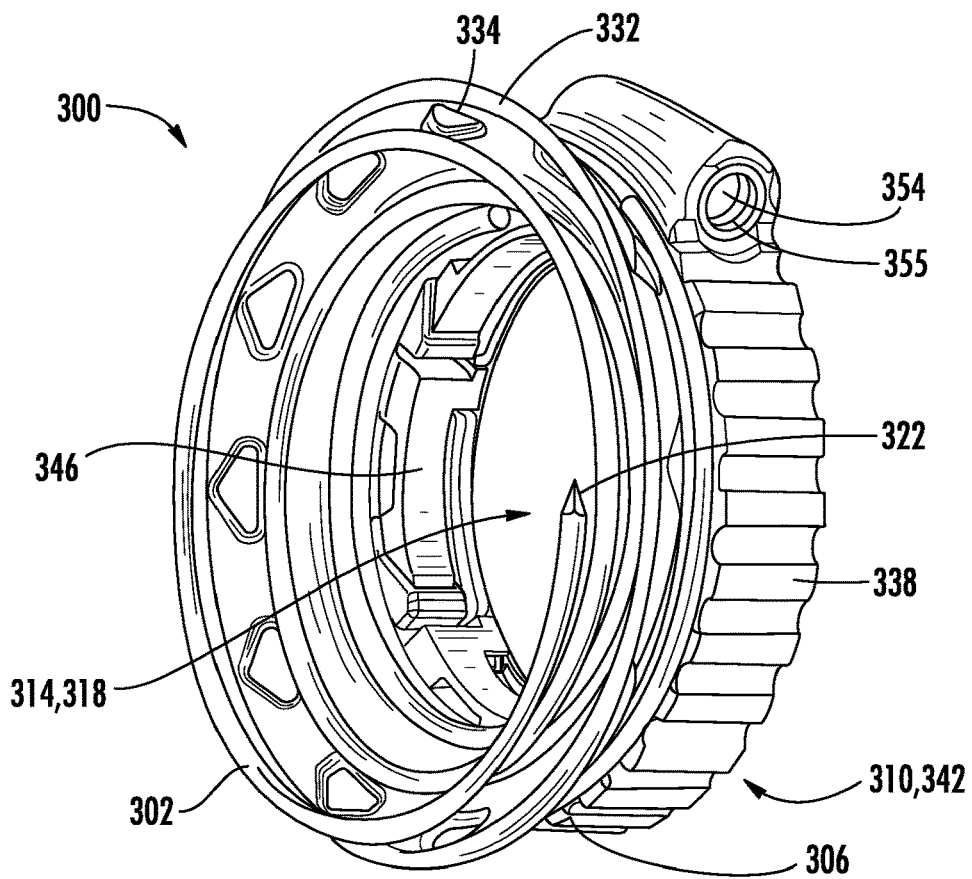

FIG. 3A shows a non-limiting perspective view of an exemplary connector for implanting and using in a tissue wall, in accordance with one embodiment of the present invention as may be described herein.

Figure 3B:
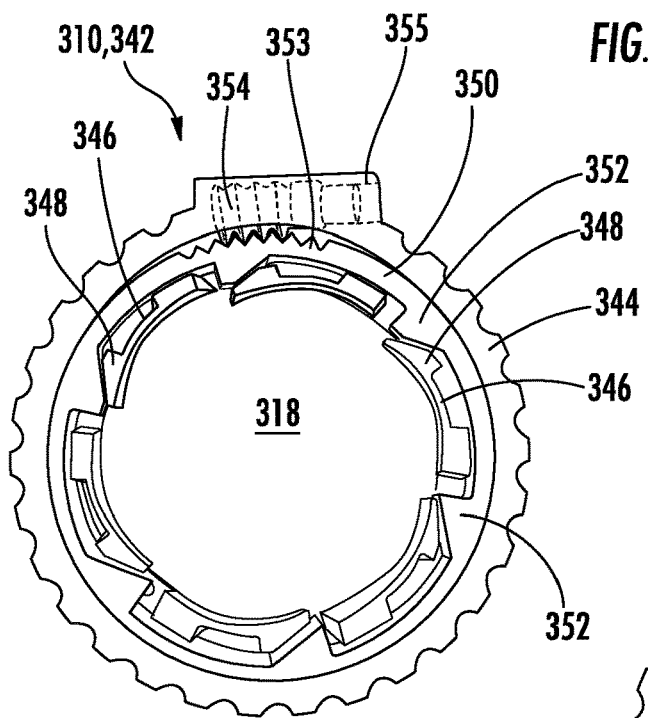

FIG. 3B shows a non-limiting top view of a worm gear collet mechanism of the connector of FIG. 3A.

Figure 3C:
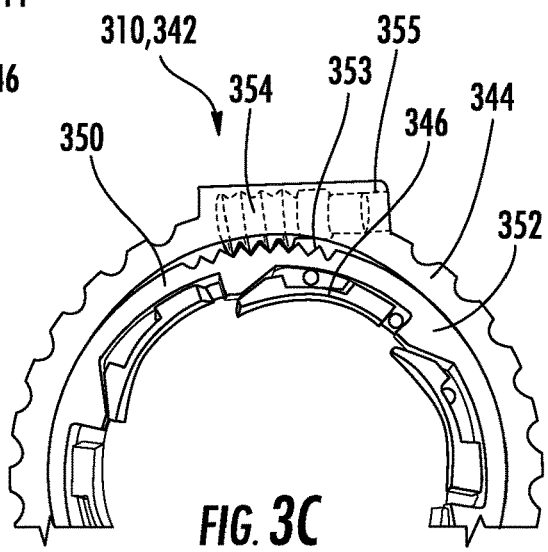

FIG. 3C shows a non-limiting top view of a worm gear collet mechanism of the connector of FIG. 3A.

Figure 4A:
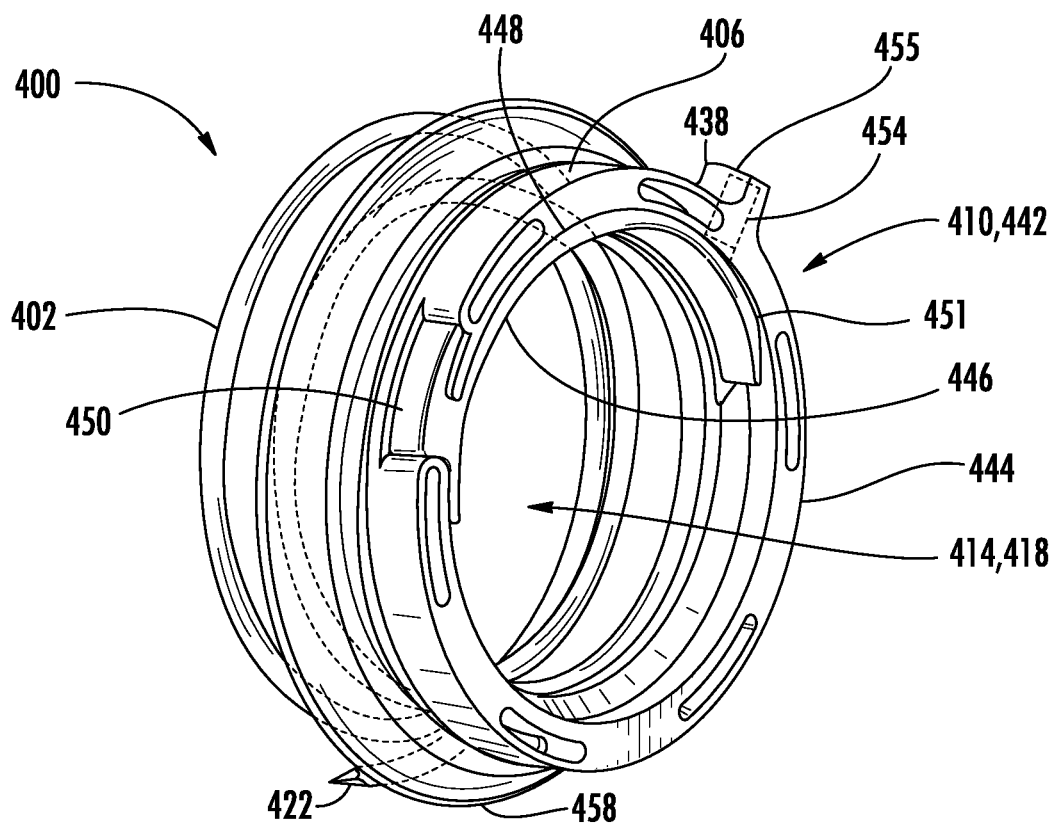

FIG. 4A shows a non-limiting perspective view of an exemplary connector for implanting and using in a tissue wall, in accordance with one embodiment of the present invention as may be described herein.

Figure 4B:
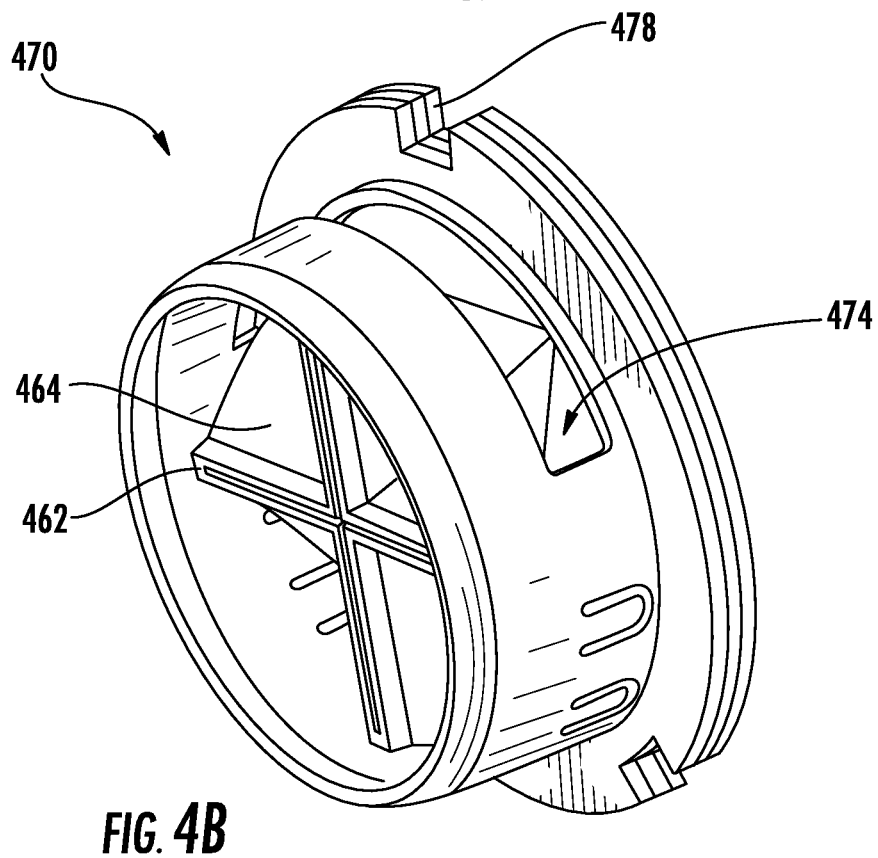

FIG. 4B shows a non-limiting perspective view of a cannula of the connector of FIG. 4A.

Figure 4C:
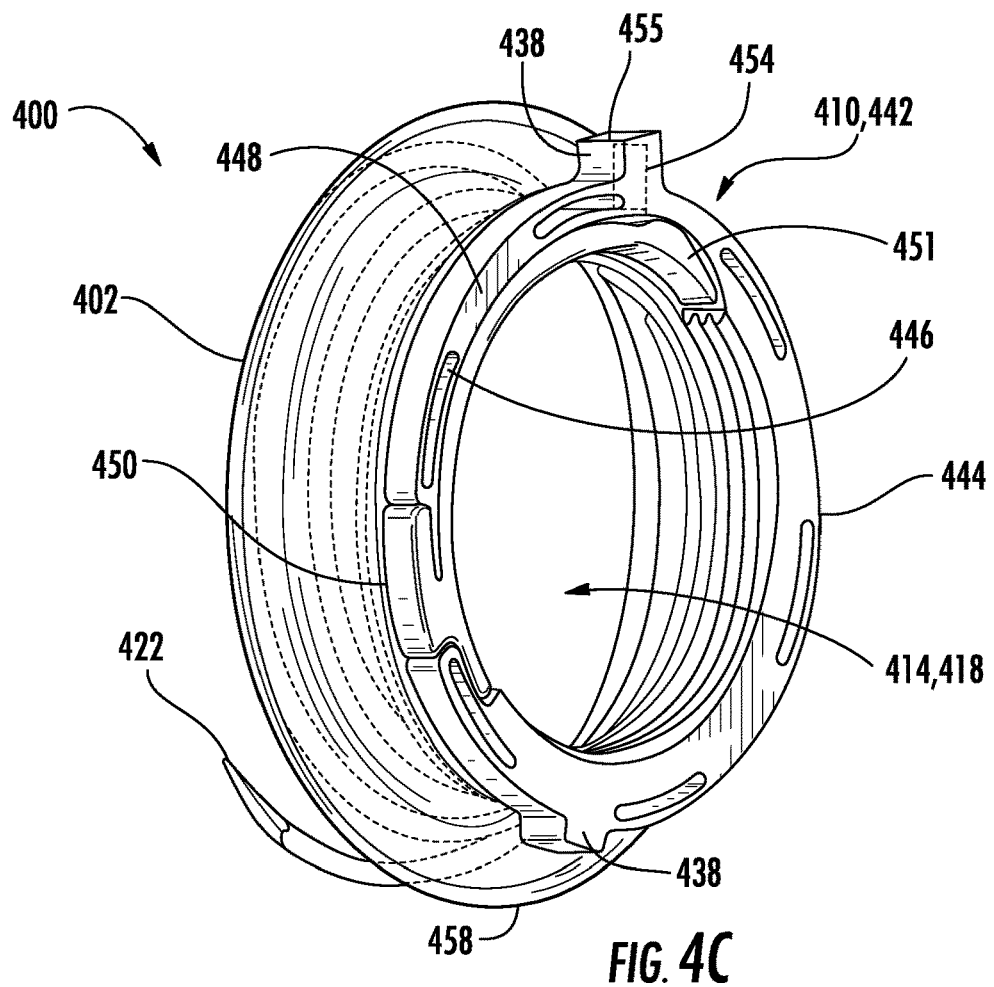

FIG. 4C shows a non-limiting perspective view of an exemplary connector for implanting and using in a tissue wall, in accordance with one embodiment of the present invention as may be described herein.

Figure 4D:
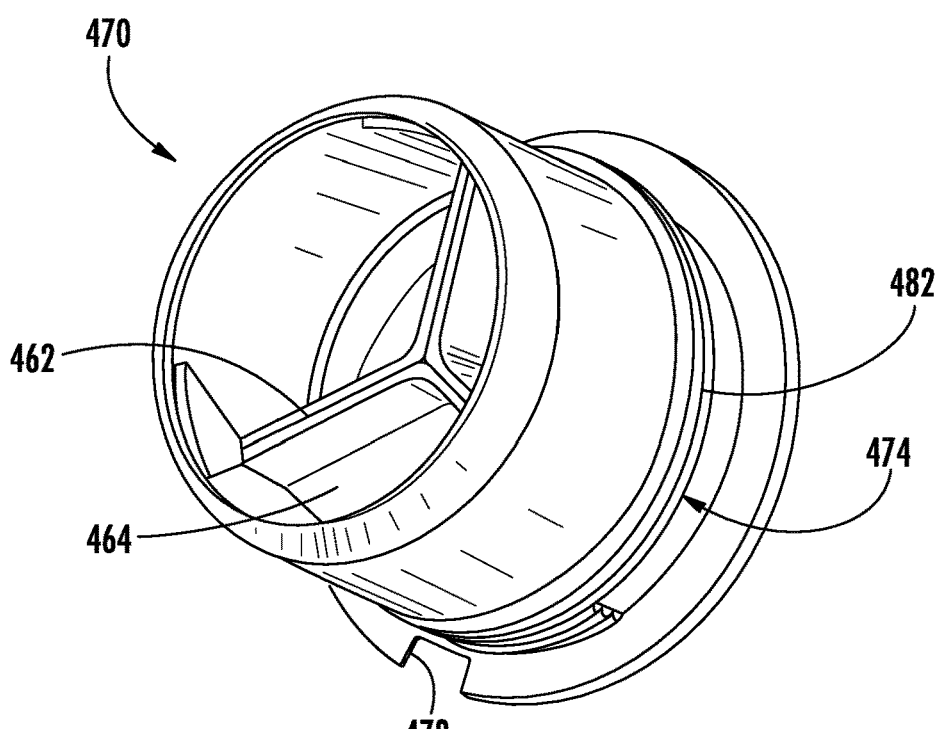

FIG. 4D shows a non-limiting perspective view of a cannula of the connector of FIG. 4C.

Figure 4E:
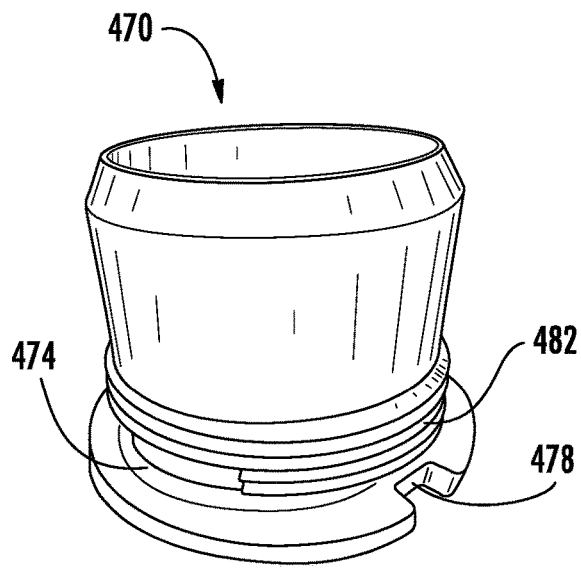

FIG. 4E shows a non-limiting perspective view of the cannula of FIG. 4D.

Figure 4F:
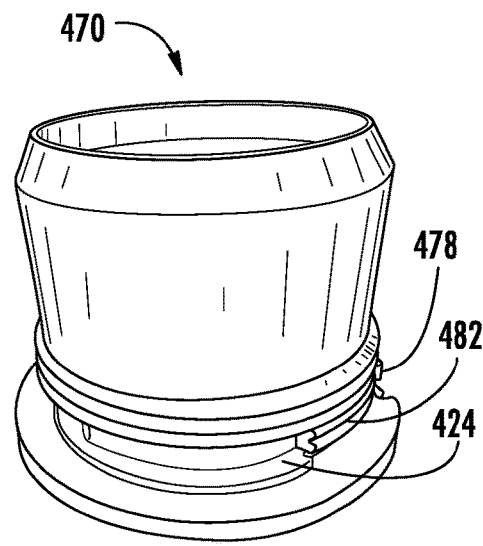

FIG. 4F shows a non-limiting perspective view of the cannula of FIG. 4D.

Figure 4G:
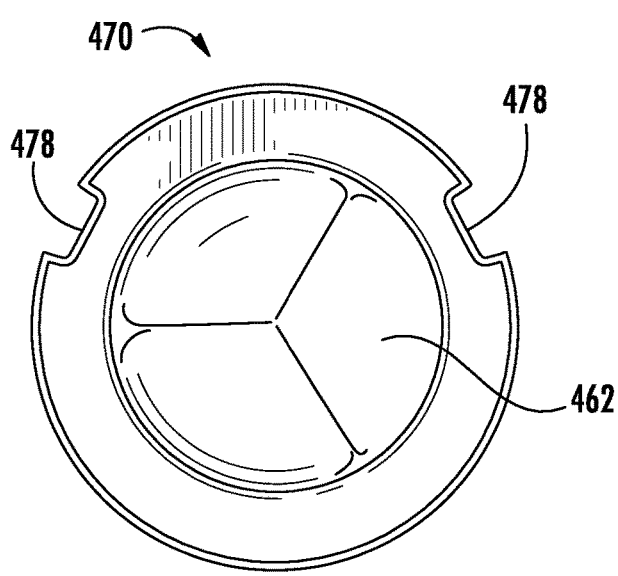

FIG. 4G shows a non-limiting top view of the cannula of FIG. 4D.

Figure 4H:
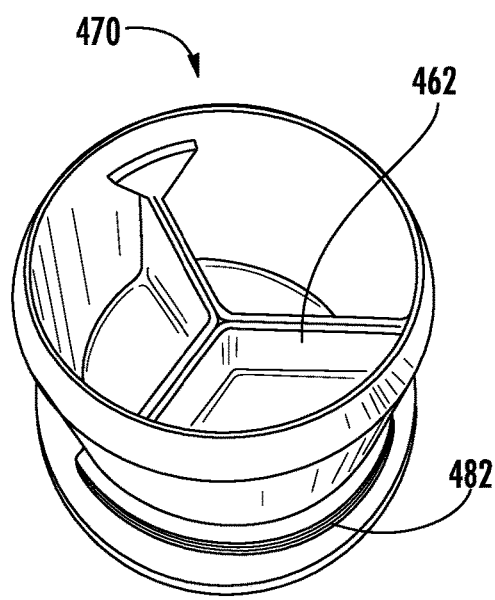
Figure 41:
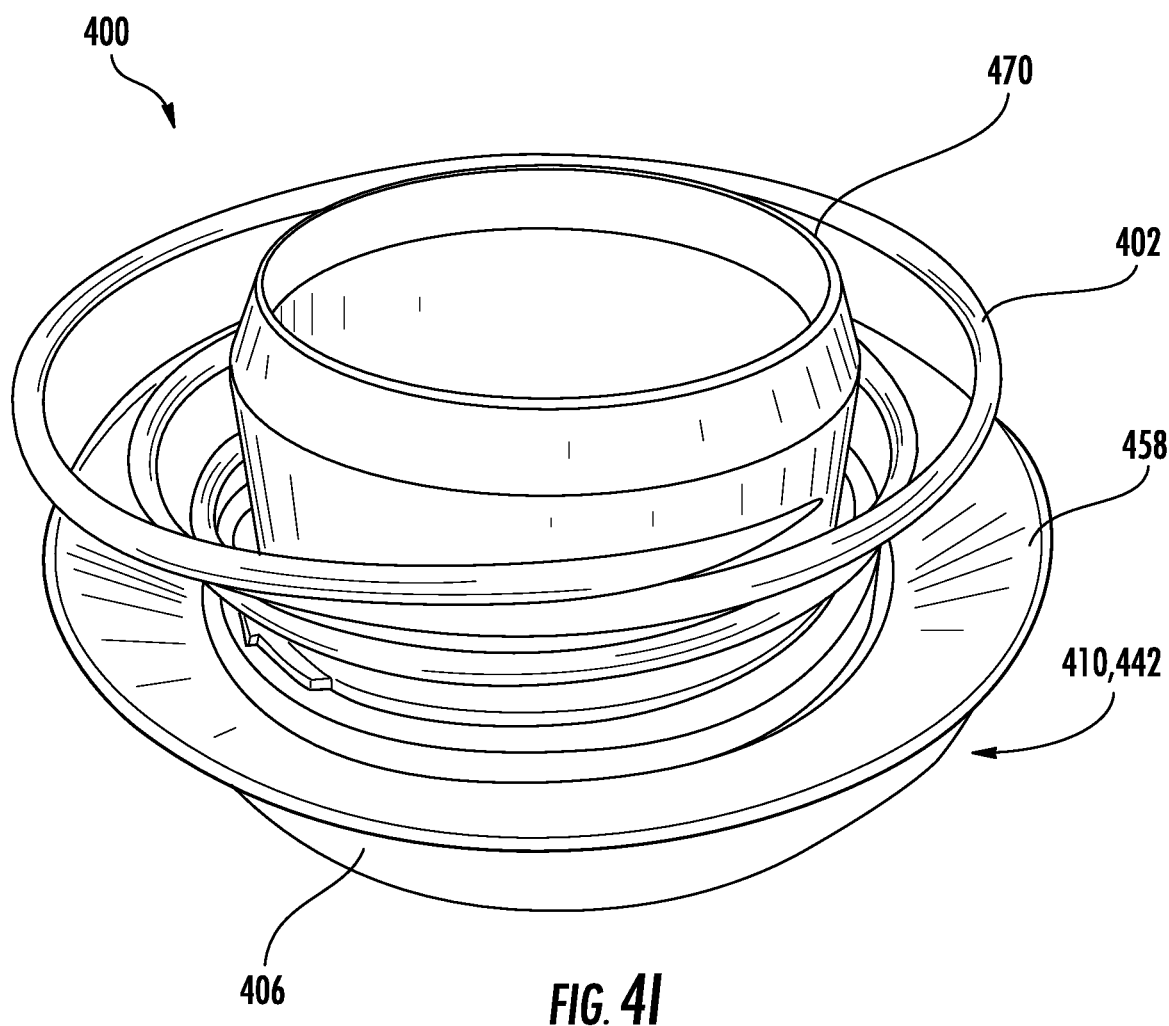

FIG. 4H shows a non-limiting perspective view of the cannula of FIG. 4D.

FIG. 4I shows a non-limiting perspective view of an exemplary connector for implanting and using in a tissue wall, in accordance with one embodiment of the present invention as may be described herein.

Figure 5A:
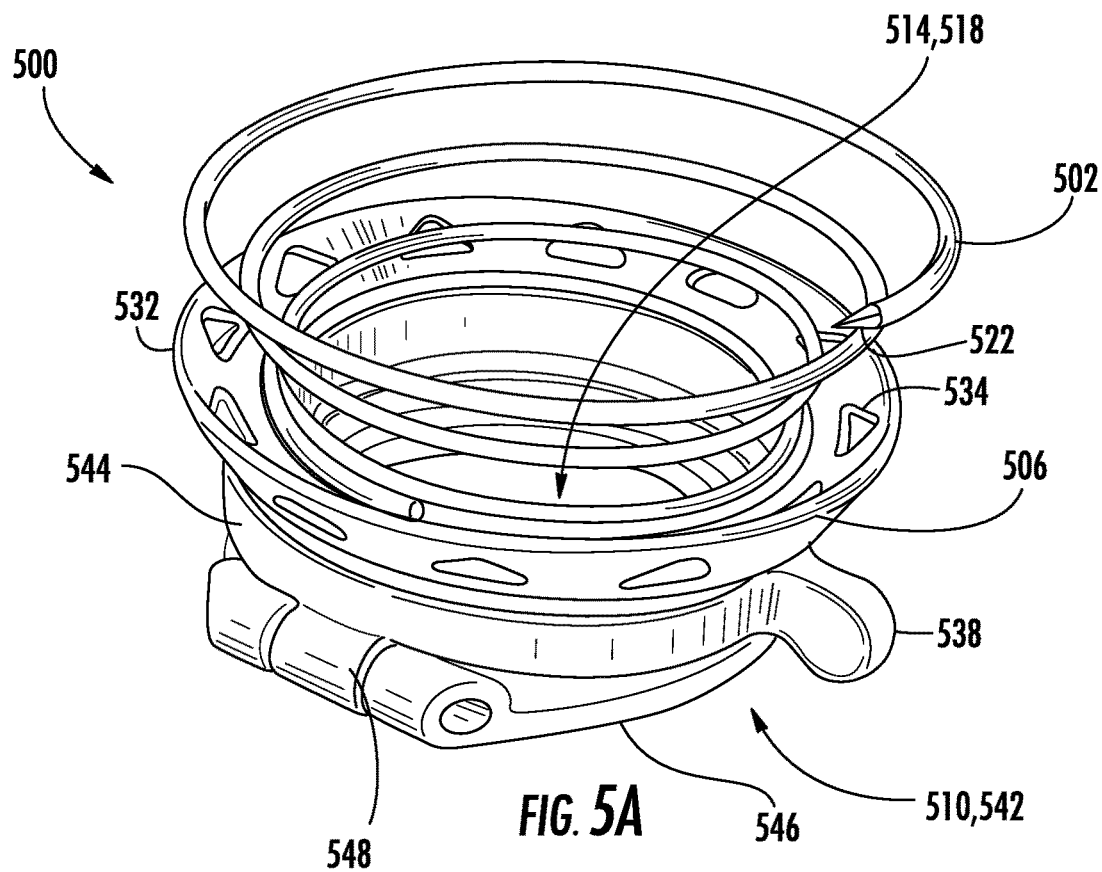

FIG. 5A shows a non-limiting perspective view of an exemplary connector for implanting and using in a tissue wall, in accordance with one embodiment of the present invention as may be described herein.

Figure 5B:
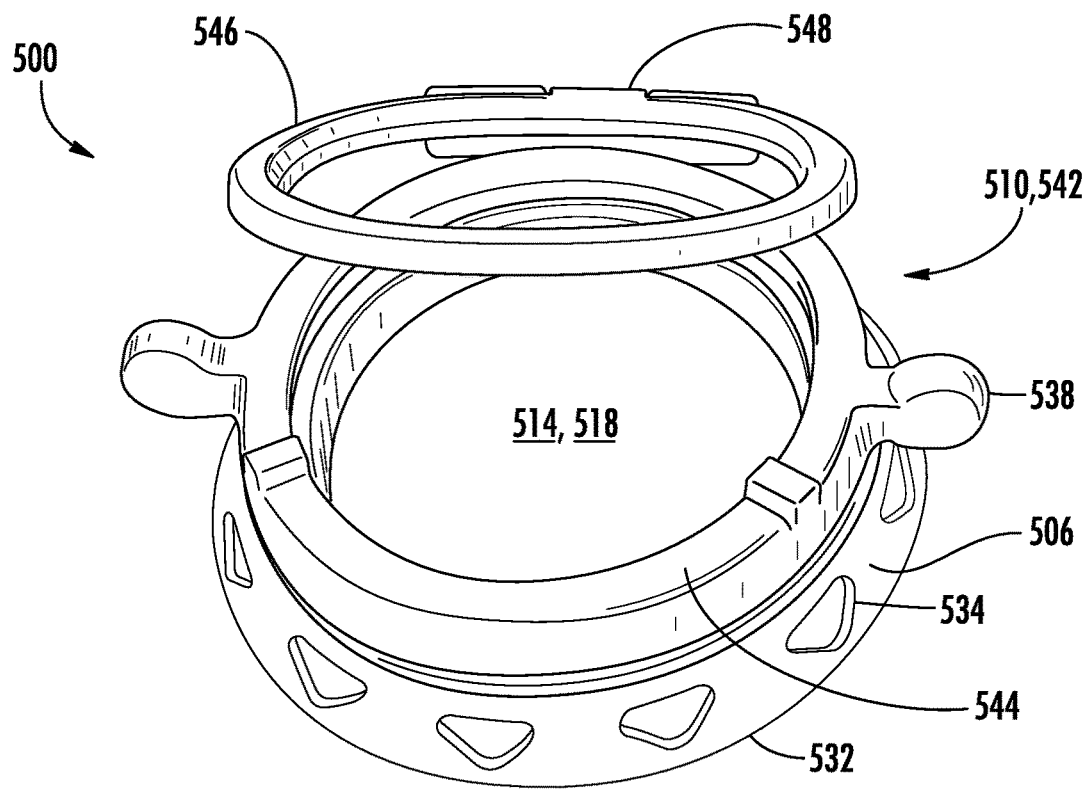

FIG. 5B shows a non-limiting perspective view of the connector of FIG. 5A.

Figure 5C:
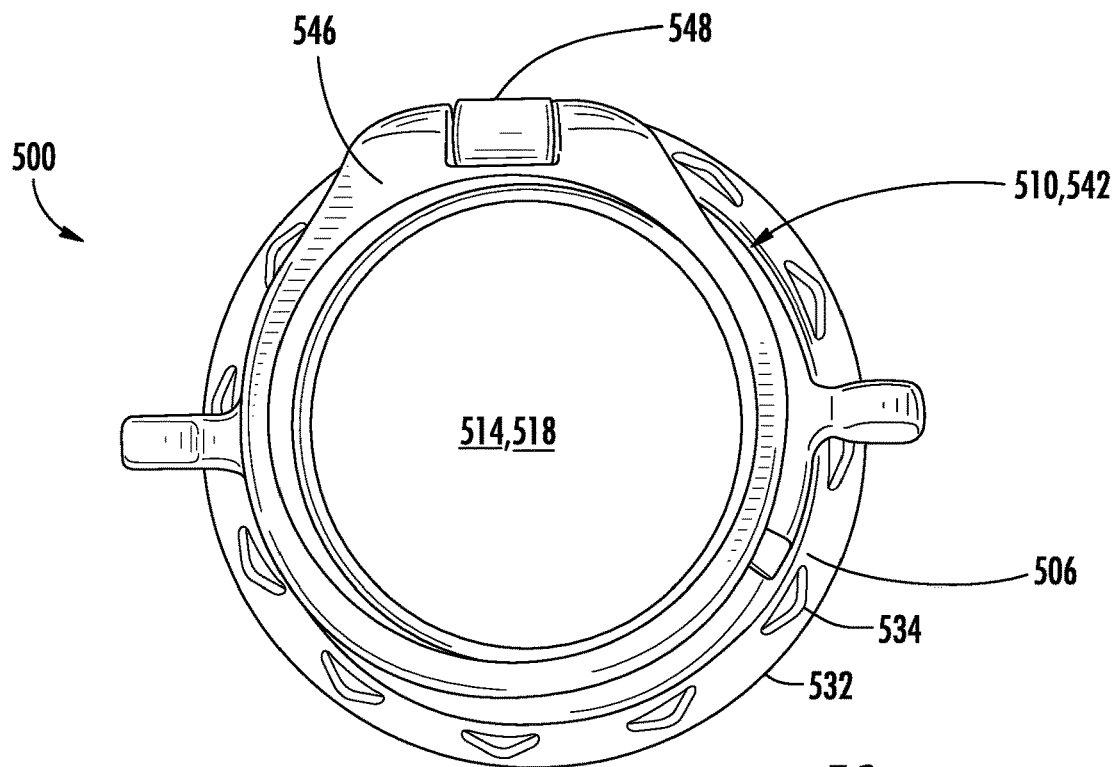

FIG. 5C shows a non-limiting top view of the connector of FIG. 5A.

Figure 5D:
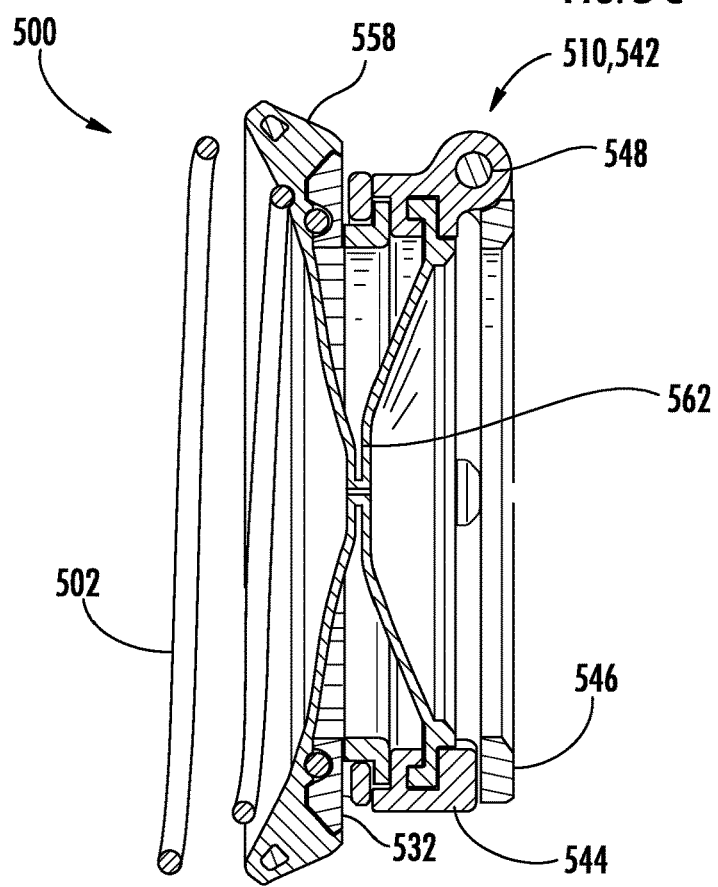

FIG. 5D shows a non-limiting side cross-sectional view of the connector of FIG. 5A.

Figure 5E:
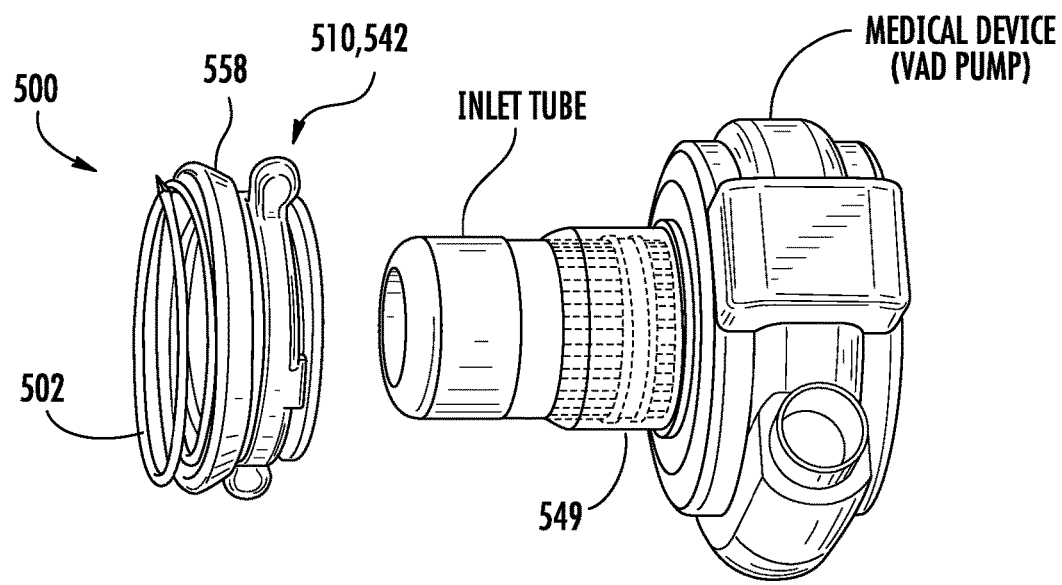

FIG. 5E shows a non-limiting perspective view of the connector of FIG. 5A and a mating medical device.

Figure 5F:
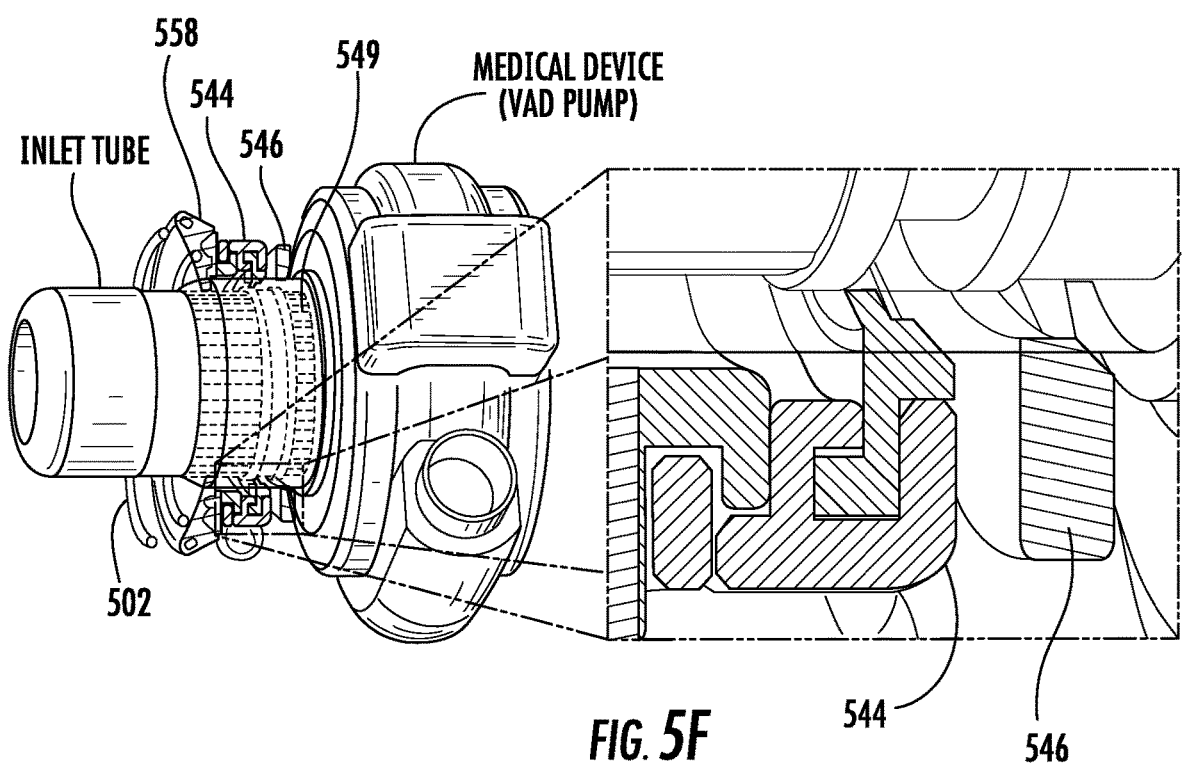

FIG. 5F shows a non-limiting perspective view of the connector of FIG. 5A and a mating medical device.

Figure 6A:
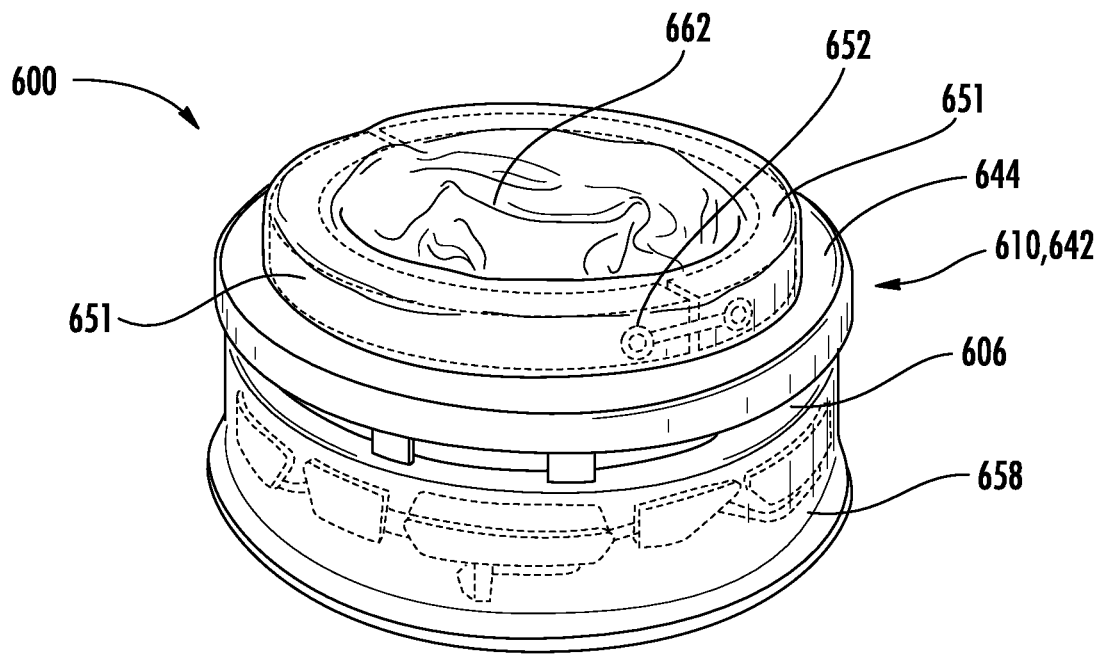

FIG. 6A shows a non-limiting perspective view of an exemplary connector for implanting and using in a tissue wall, in accordance with one embodiment of the present invention as may be described herein.

Figure 6B:
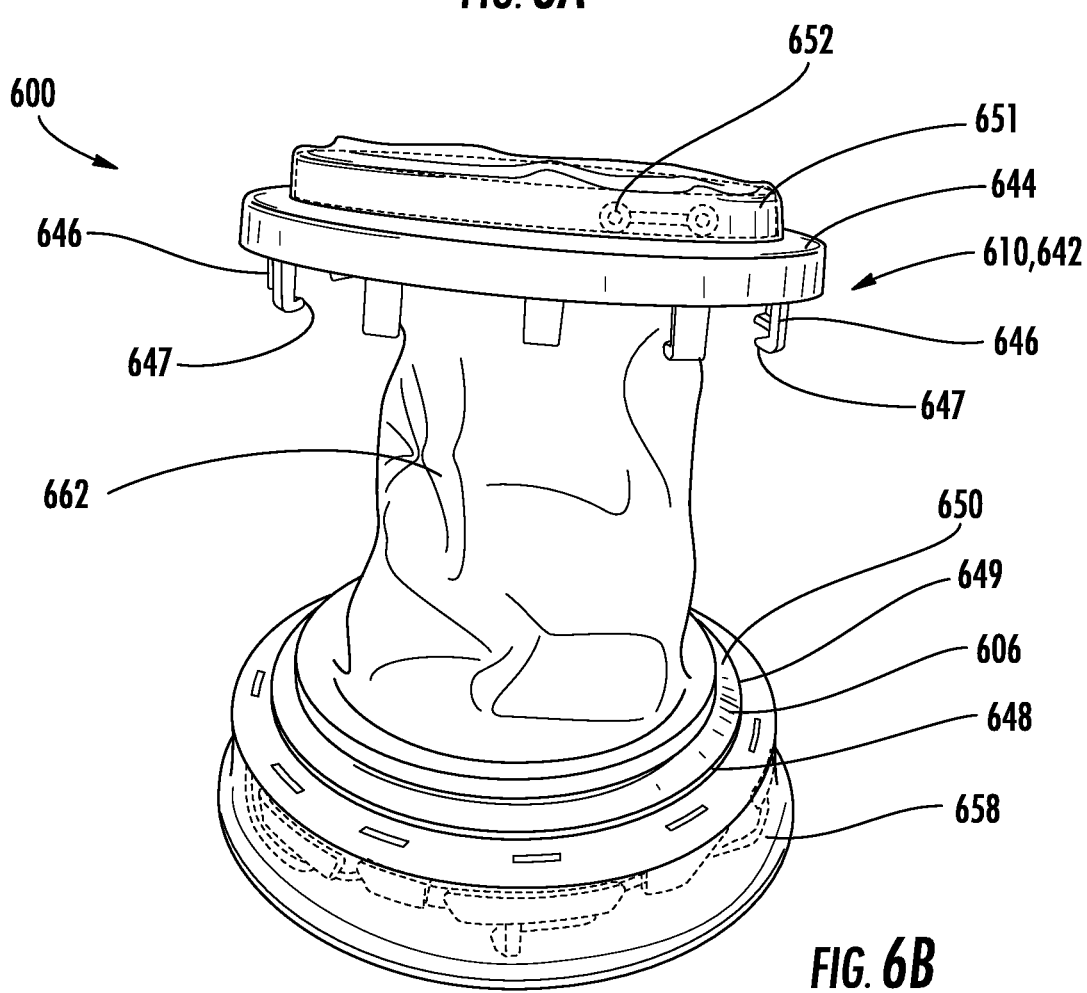

FIG. 6B shows a non-limiting side perspective view of the connector of FIG. 6A.

Figure 6C:
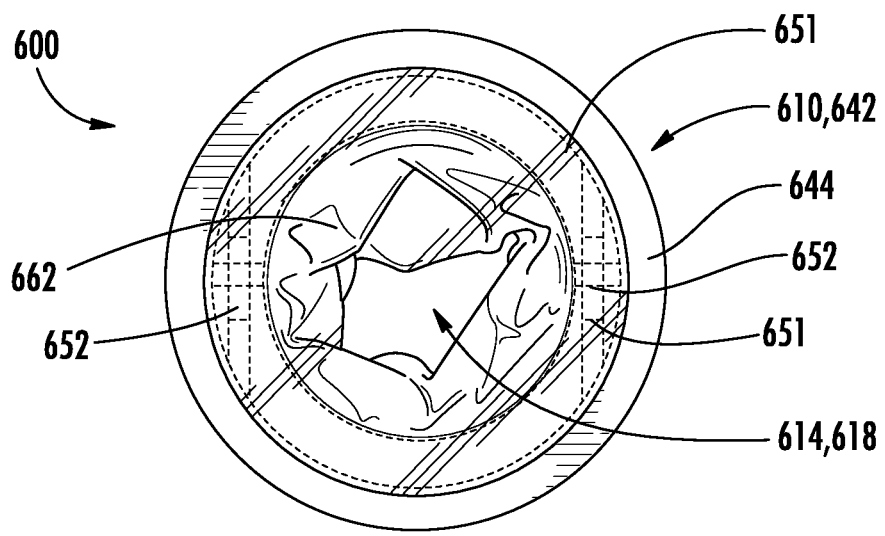

FIG. 6C shows a non-limiting top view of the connector of FIG. 6A.

Figure 6D:
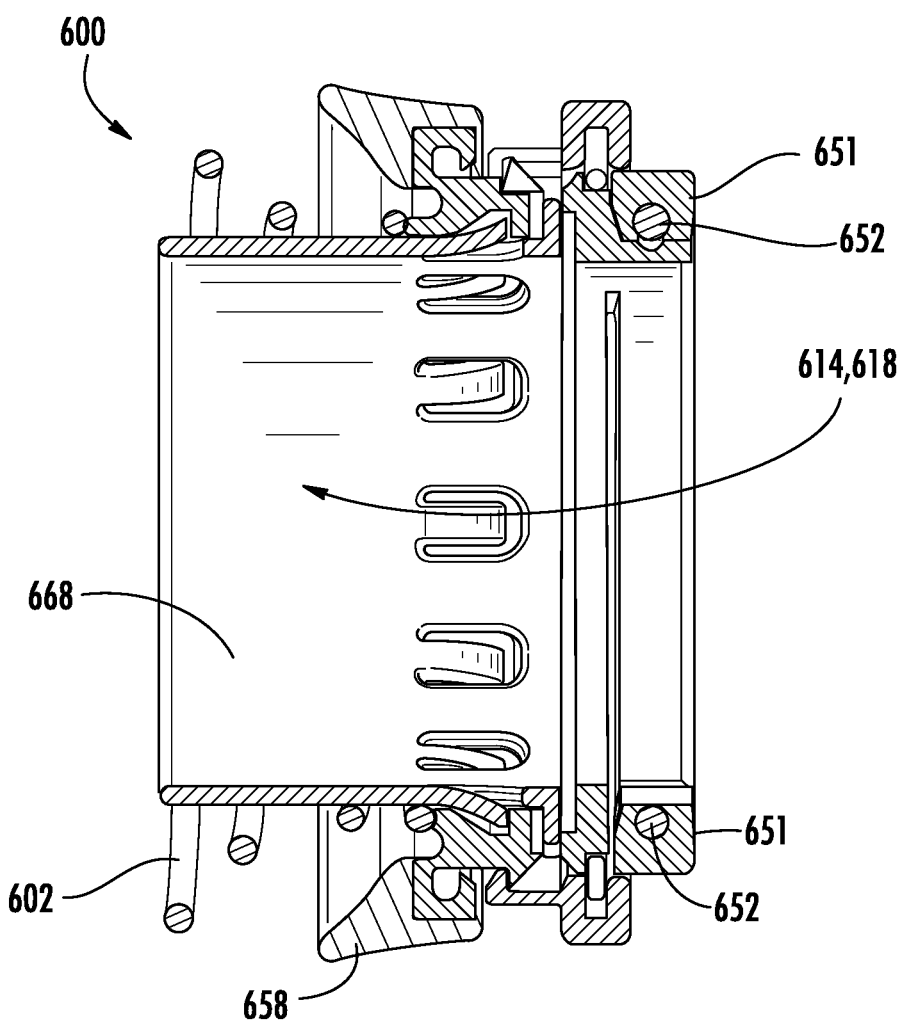

FIG. 6D shows a non-limiting side cross-sectional view of the connector of FIG. 6A.

Figure 6E:
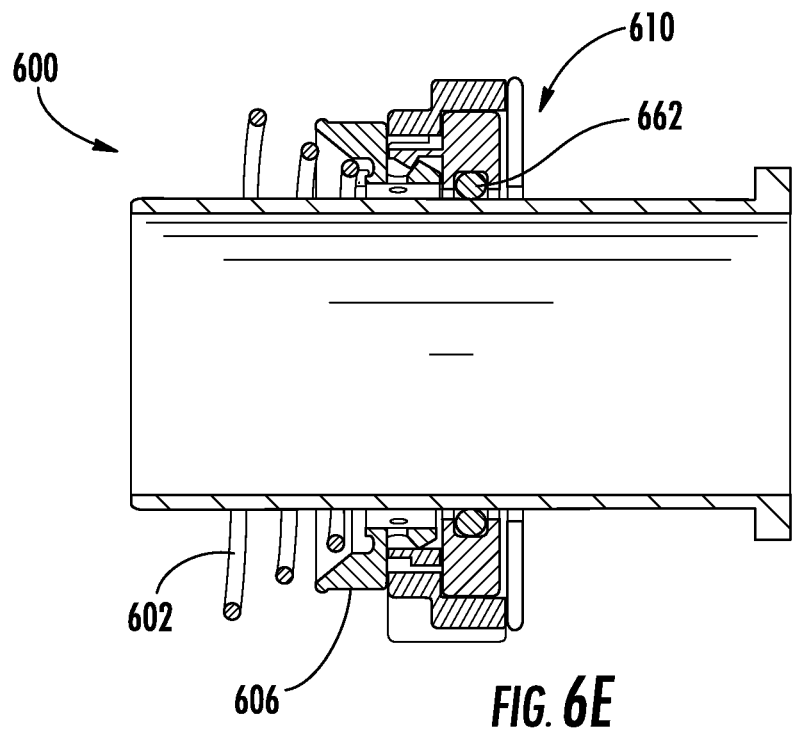

FIG. 6E shows a non-limiting perspective view of an exemplary connector for implanting and using in a tissue wall, in accordance with one embodiment of the present invention as may be described herein.

Figure 6F:
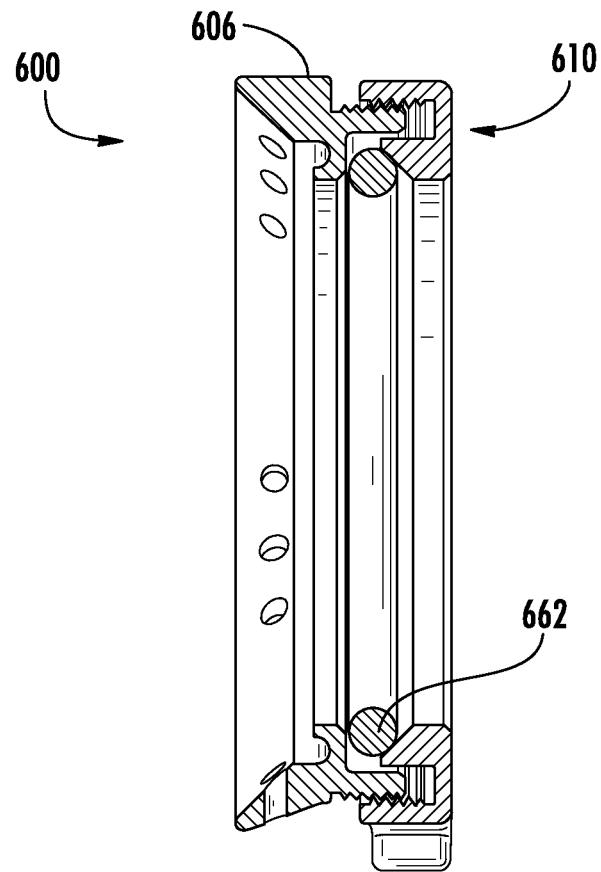

FIG. 6F shows a non-limiting perspective view of an exemplary connector for implanting and using in a tissue wall, in accordance with one embodiment of the present invention as may be described herein.

Figure 6G:
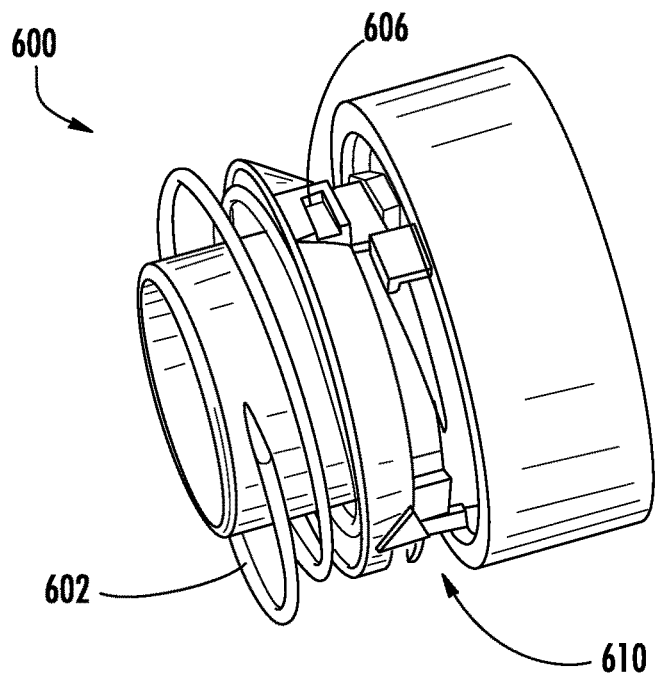

FIG. 6G shows a non-limiting perspective view of an exemplary connector for implanting and using in a tissue wall, in accordance with one embodiment of the present invention as may be described herein.

Figure 6H:
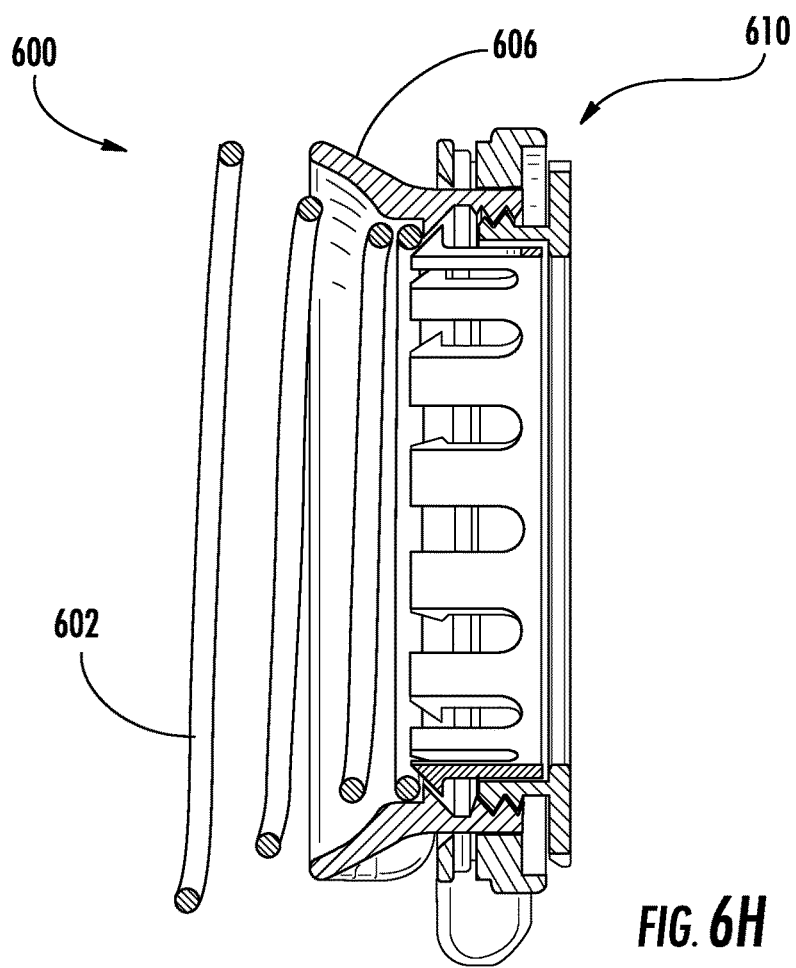

FIG. 6H shows a non-limiting perspective view of an exemplary connector for implanting and using in a tissue wall, in accordance with one embodiment of the present invention as may be described herein.

Figure 7A:
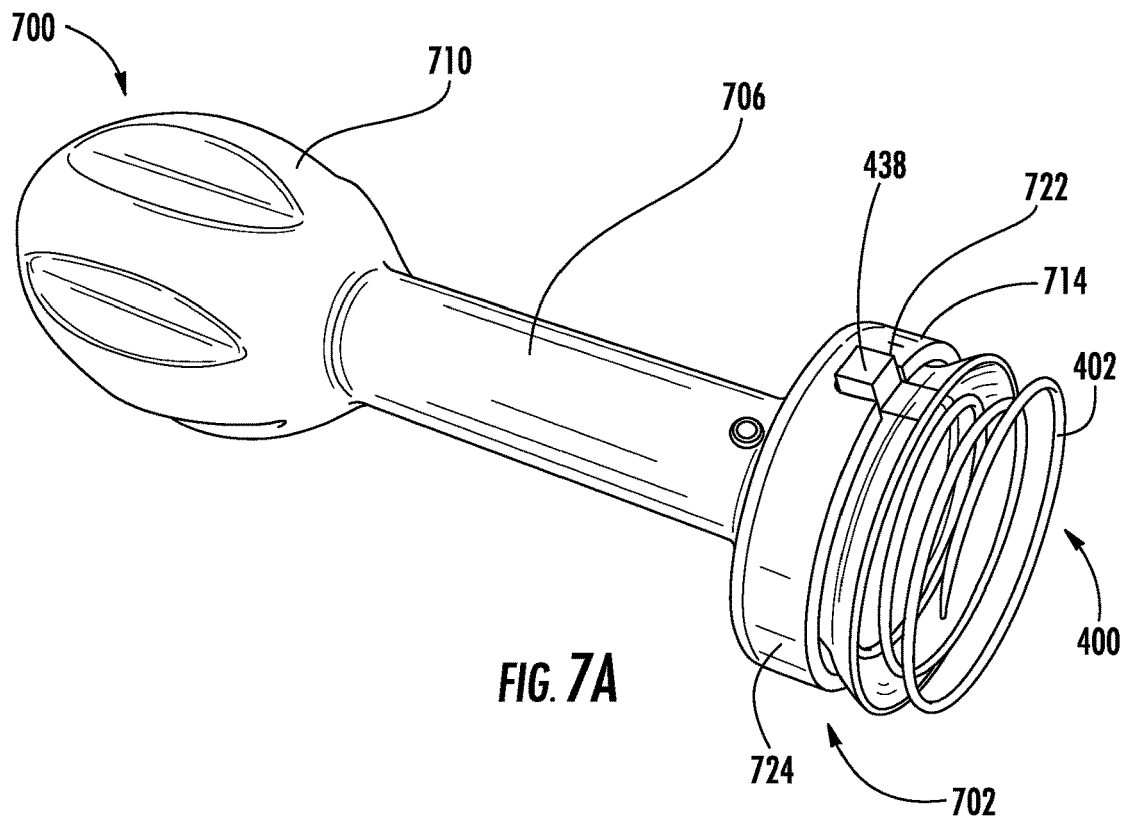

FIG. 7A shows a non-limiting perspective view of an exemplary delivery tool for implanting a connector in a tissue wall, in accordance with one embodiment of the present invention as may be described herein.

Figure 7B:
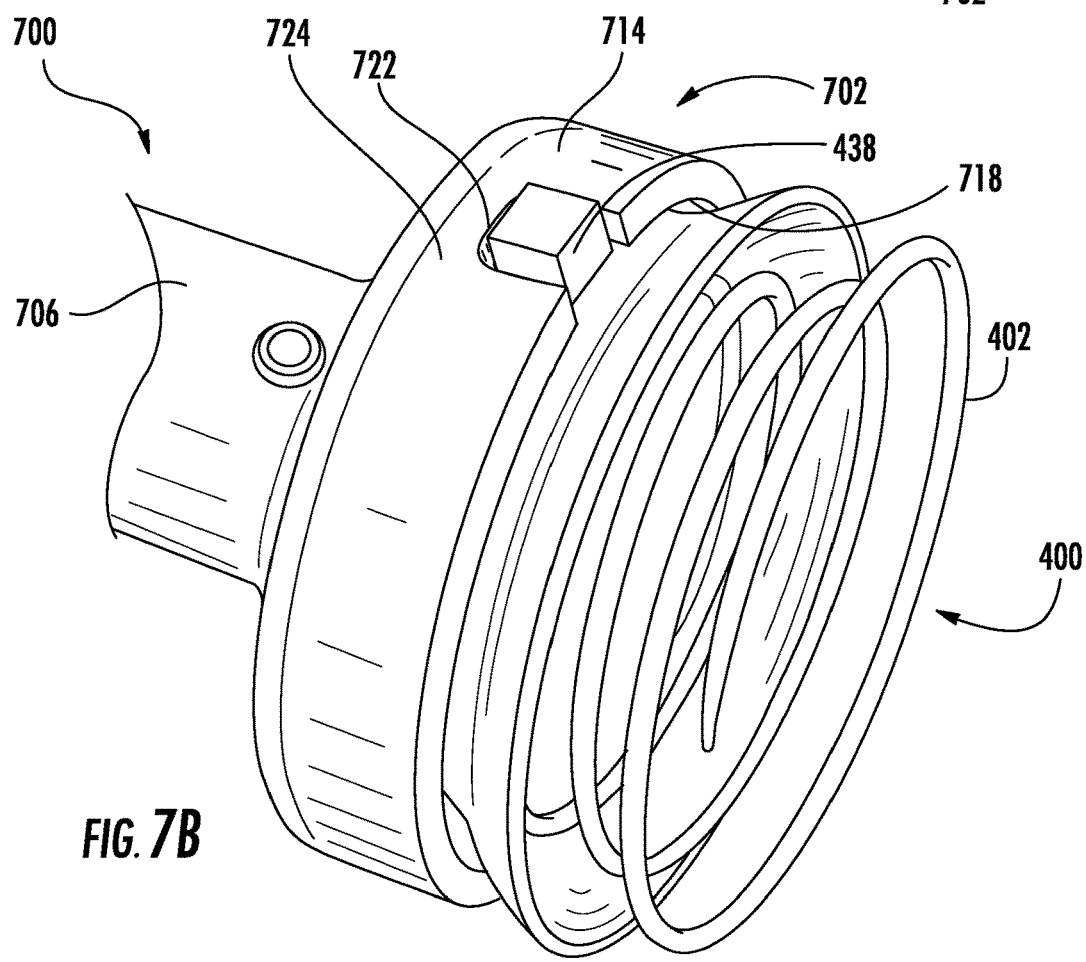

FIG. 7B shows a non-limiting detailed perspective view of the delivery tool of FIG. 7A.

Figure 8A:
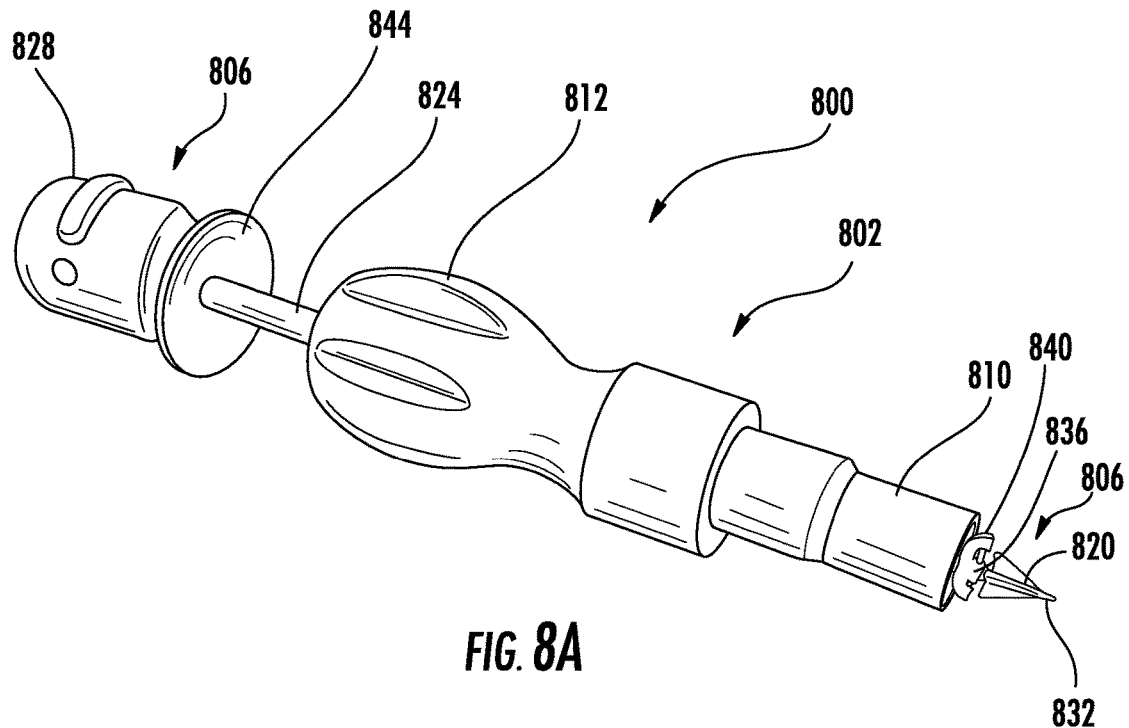

FIG. 8A shows a non-limiting perspective view of an exemplary cutting tool for forming a hole in a tissue wall, in accordance with one embodiment of the present invention as may be described herein.

Figure 8B:
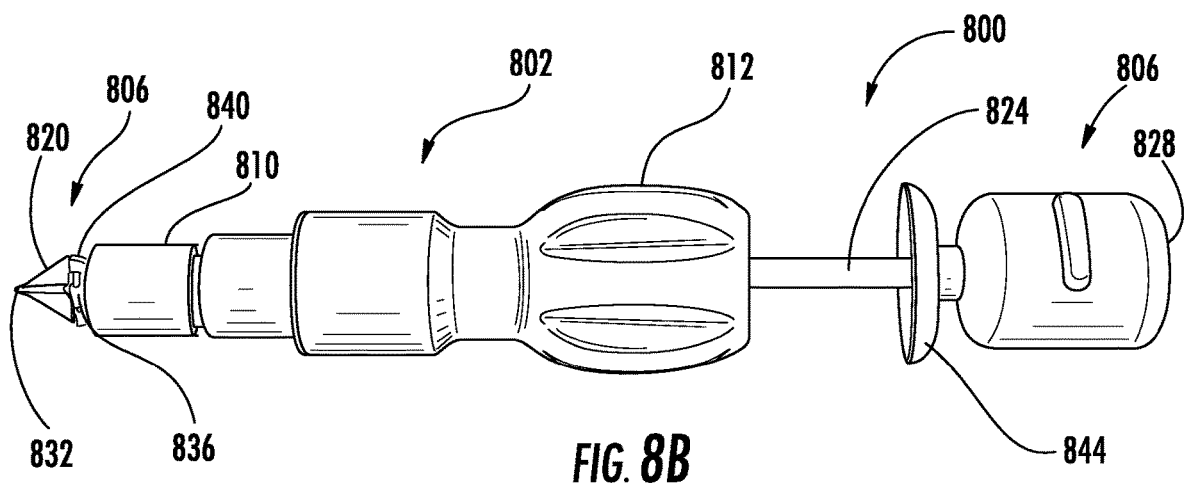

FIG. 8B shows a non-limiting side view of the cutting tool of FIG. 8A.

Figure 9A:
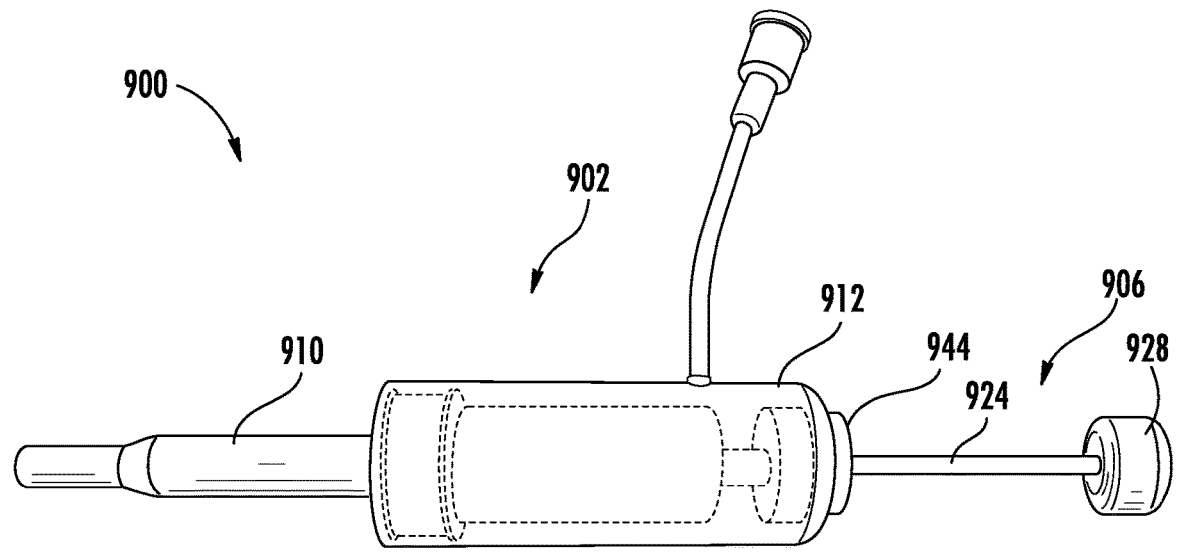

FIG. 9A shows a non-limiting perspective view of an exemplary cutting tool for forming a hole in a tissue wall, in accordance with one embodiment of the present invention as may be described herein.

Figure 9B:
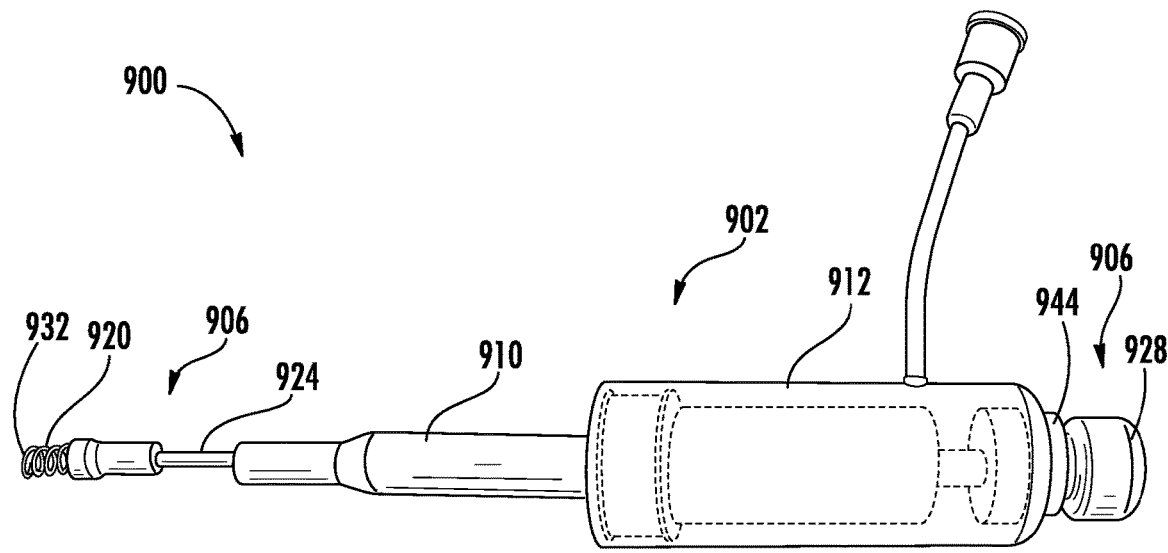

FIG. 9B shows a non-limiting side cross-sectional view of the cutting tool of FIG. 9A.

Figure 9C:
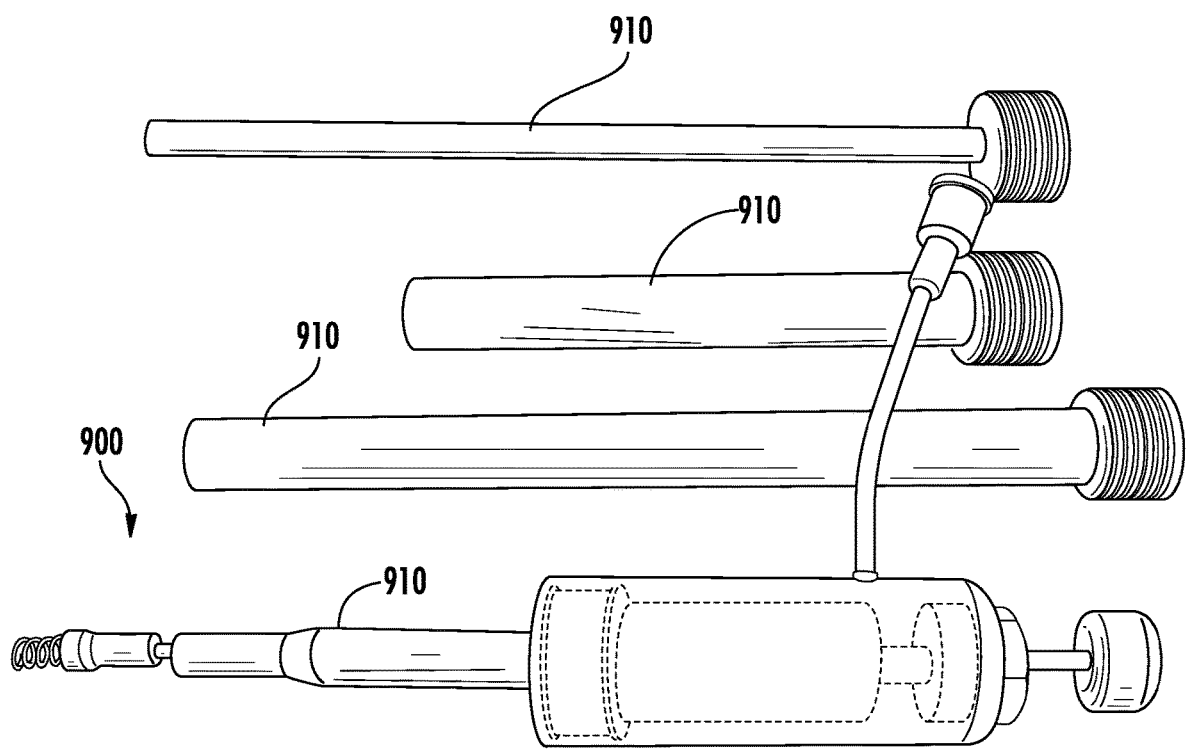

FIG. 9C shows a non-limiting side view of the cutting tool of FIG. 9A, along with various cutting tubes that may be used by the cutting tool.

Figure 10A:
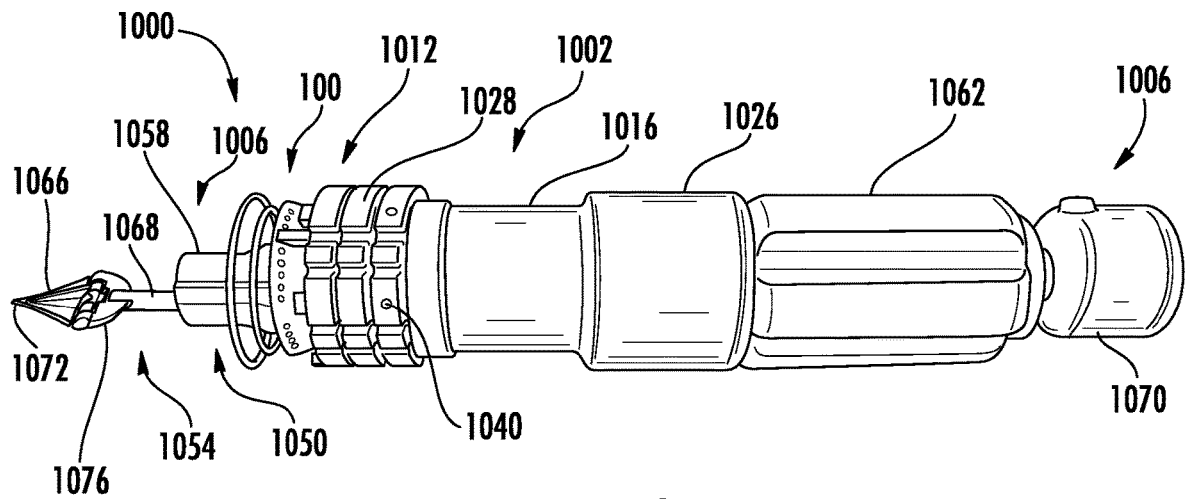

FIG. 10A shows a non-limiting side view of an exemplary combination tool for implanting a connector and forming a hole in a tissue wall, in accordance with one embodiment of the present invention as may be described herein.

Figure 10B:
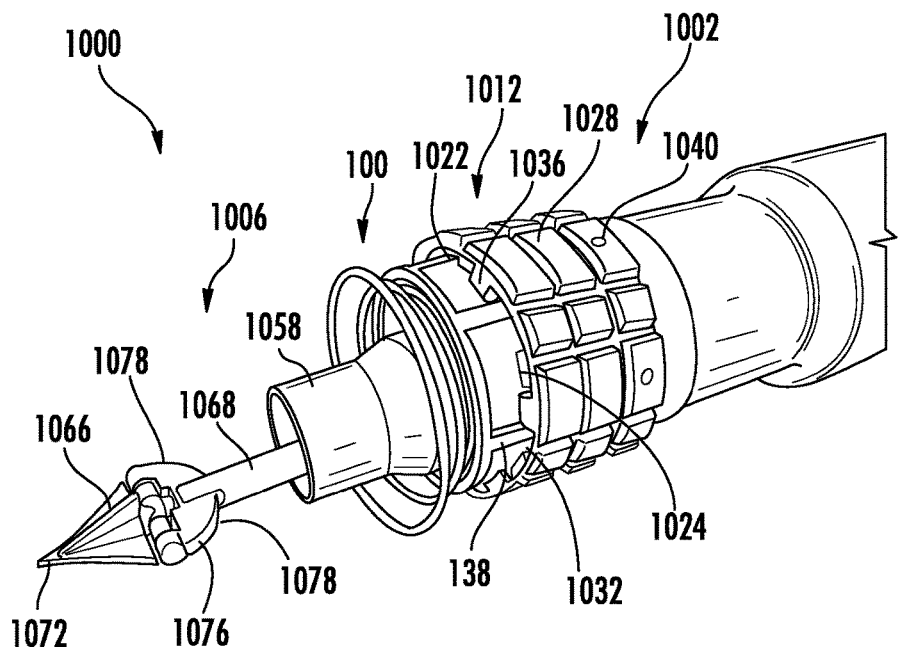

FIG. 10B shows a non-limiting detailed perspective view of the combination tool of FIG. 10A.

Figure 10C:
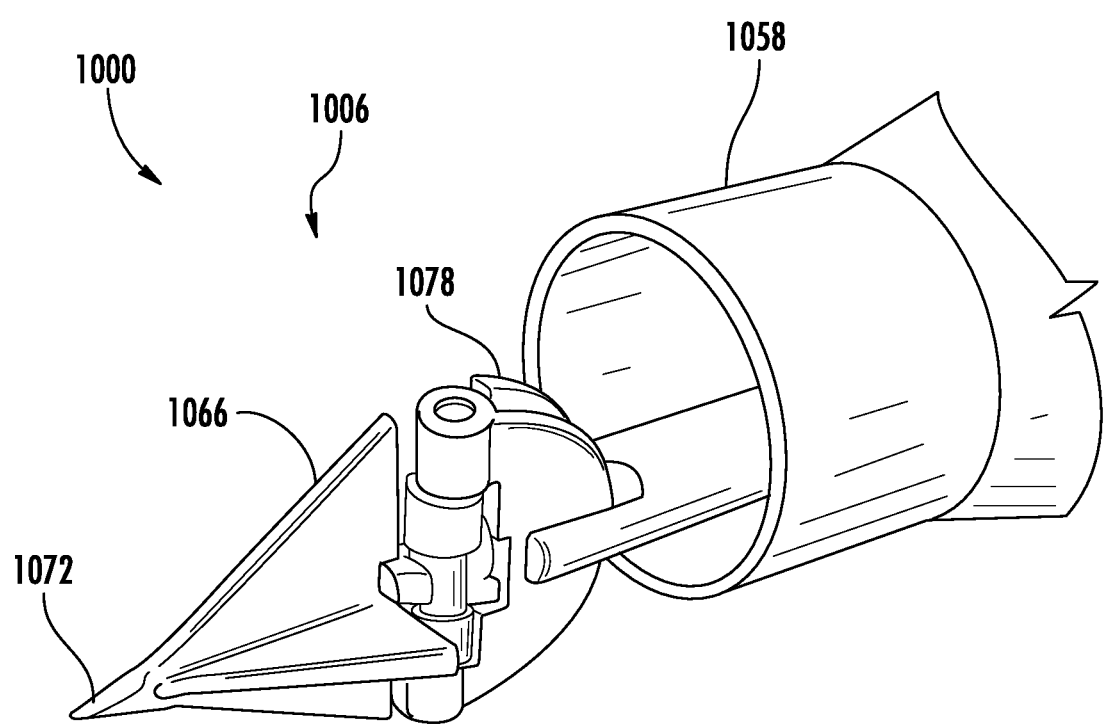

FIG. 10C shows a non-limiting detailed perspective view of the combination tool of FIG. 10A.

Figure 11A:
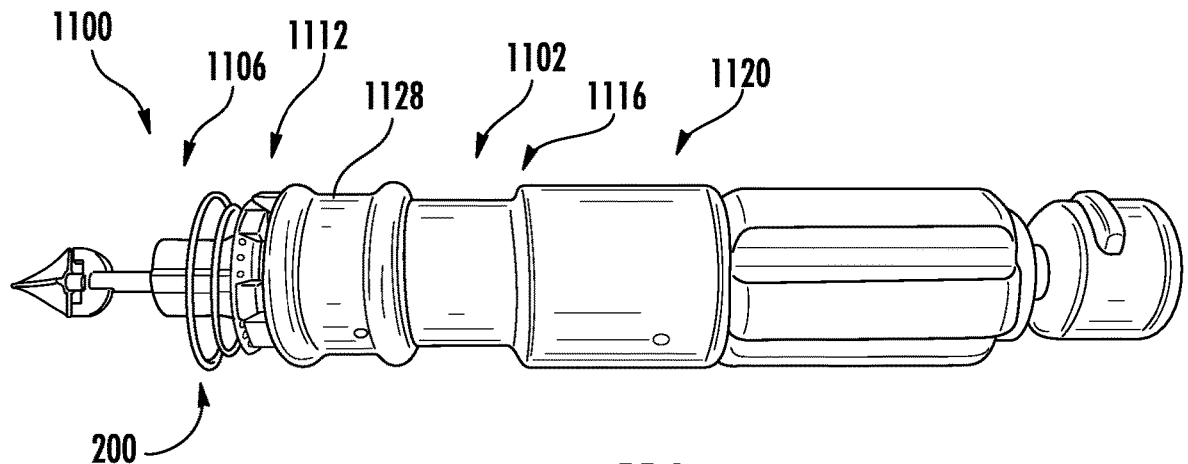

FIG. 11A shows a non-limiting side view of an exemplary combination tool for implanting a connector and forming a hole in a tissue wall, in accordance with one embodiment of the present invention as may be described herein.

Figure 11B:
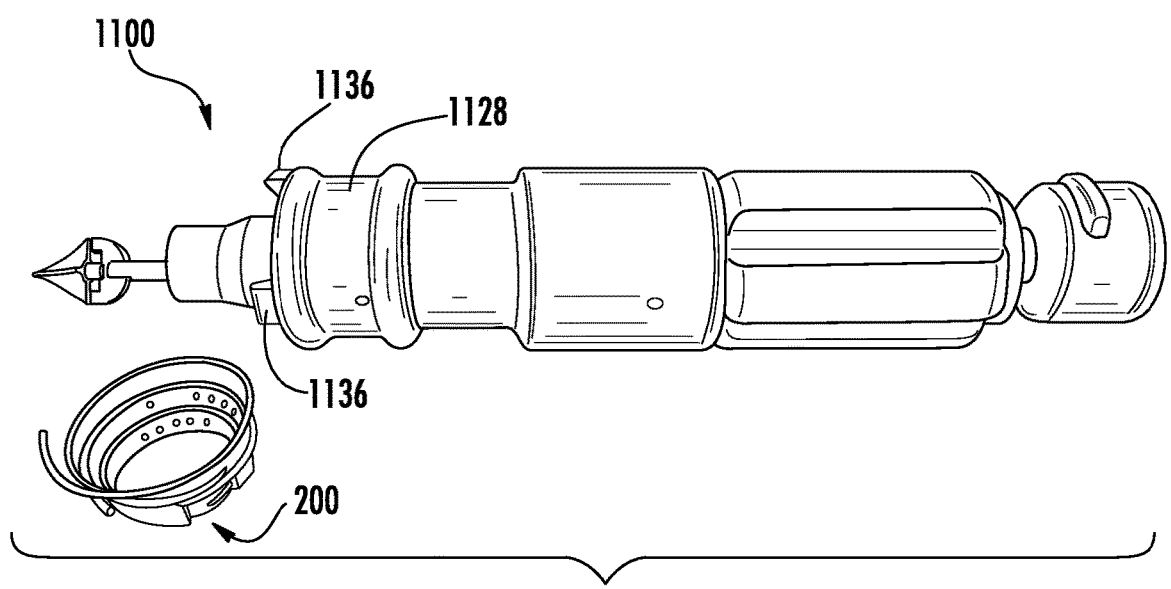

FIG. 11B shows a non-limiting side view of the combination tool of FIG. 11A.

Figure 11C:
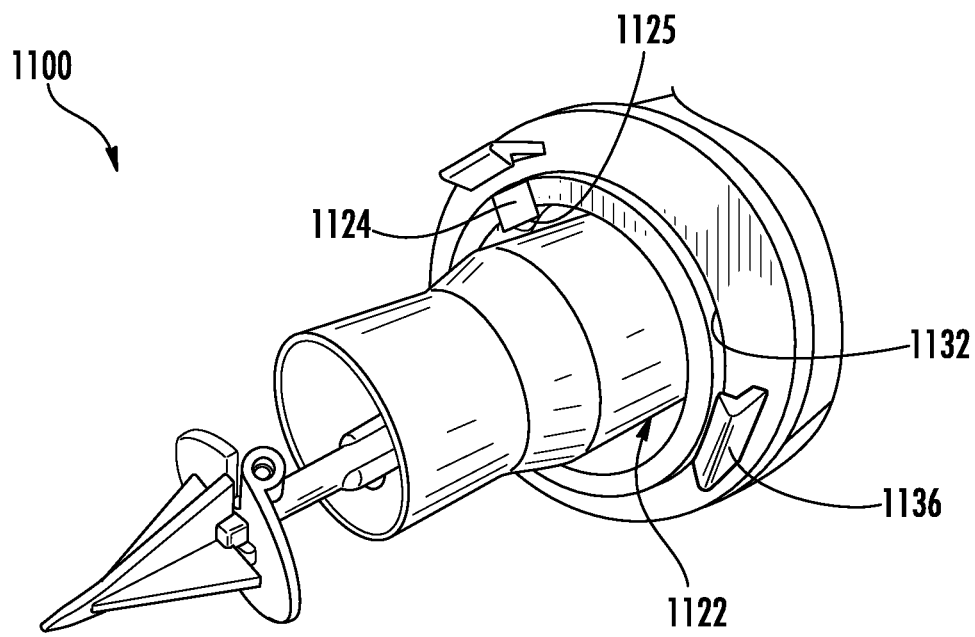

FIG. 11C shows a non-limiting detailed perspective view of the combination tool of FIG. 11A.

Figure 11D:
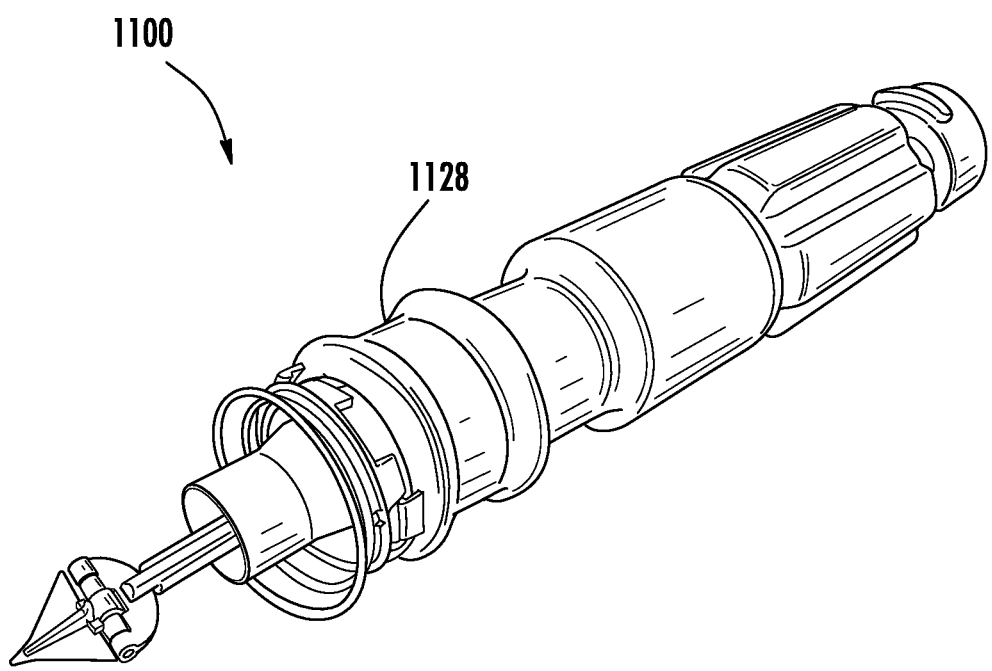

FIG. 11D shows a non-limiting perspective view of the combination tool of FIG. 11A.

Figure 12A:
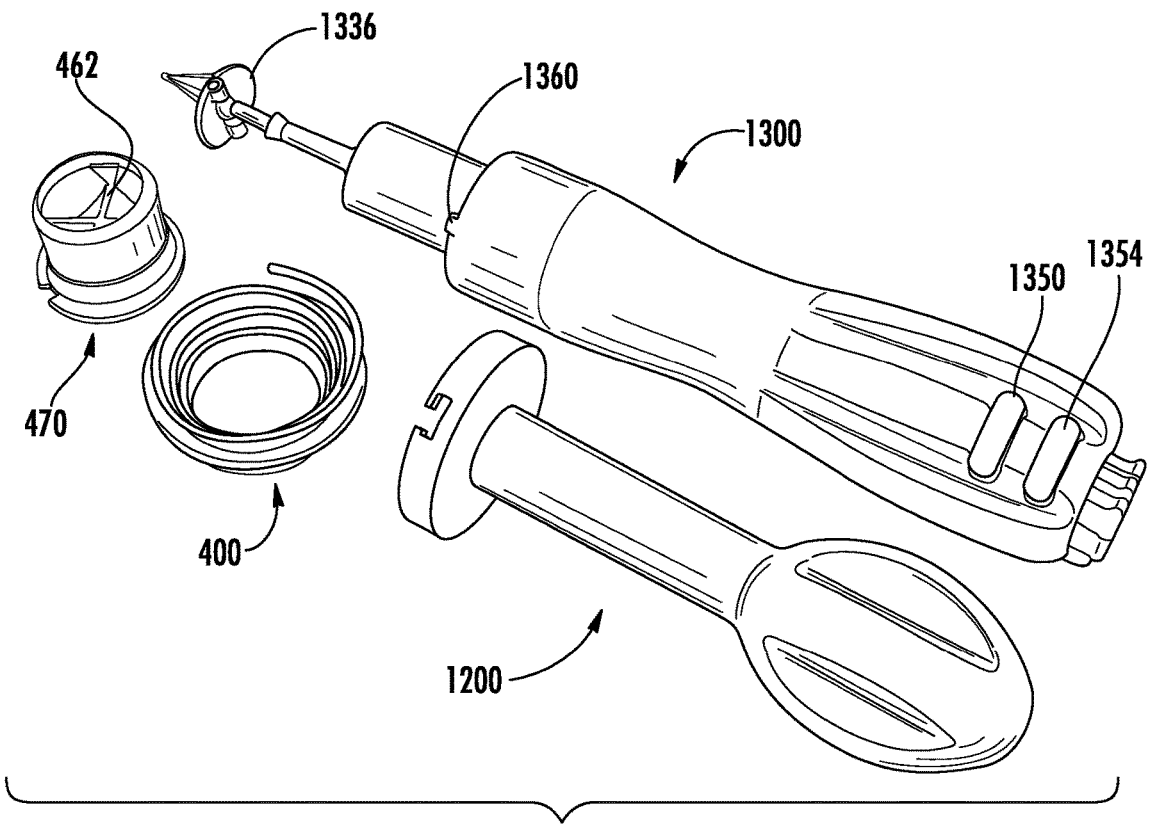

FIG. 12A shows a non-limiting side view of an exemplary system for implanting a connector and forming a hole in a tissue wall, in accordance with one embodiment of the present invention as may be described herein.

Figure 12B:
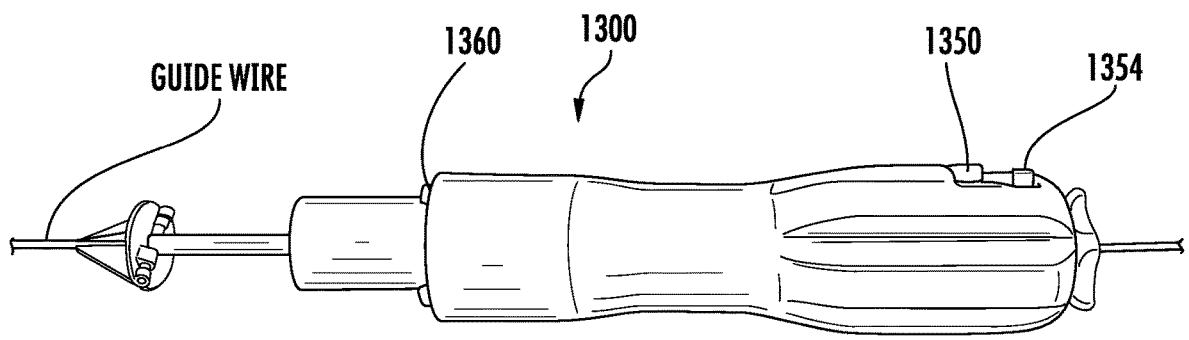

FIG. 12B shows a non-limiting perspective view of the cutting tool of the system of FIG. 12A.

Figure 12C:
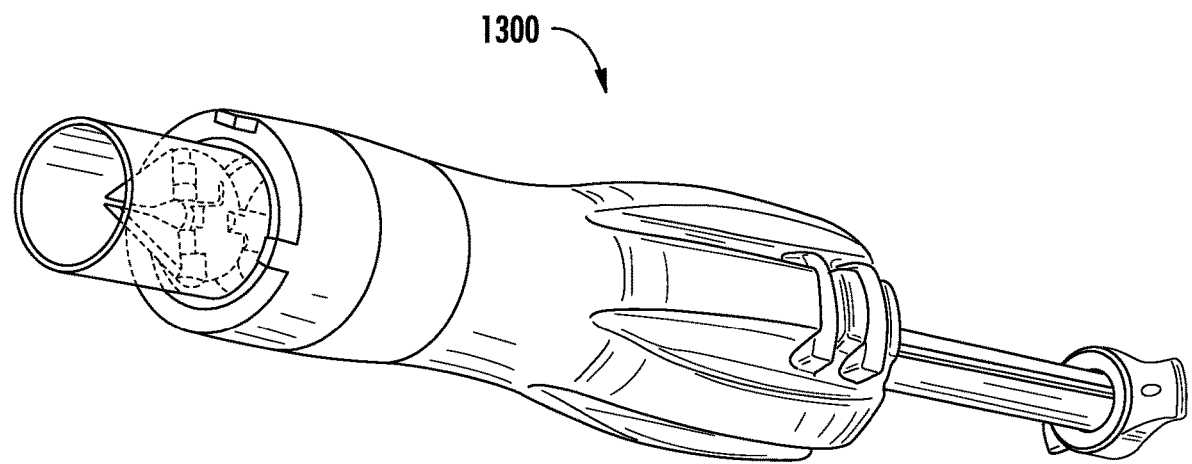

FIG. 12C shows a non-limiting perspective view of the cutting tool of the system of FIG. 12A.

Figure 12D:
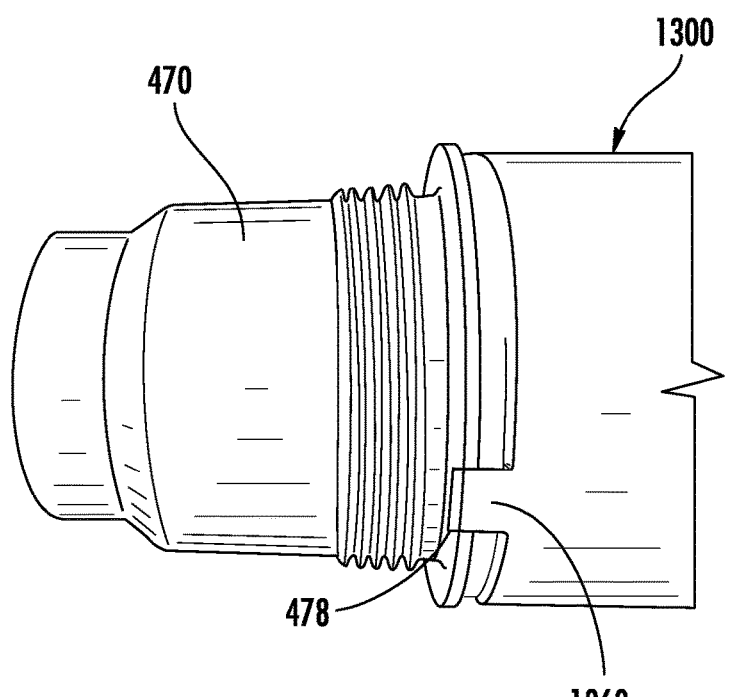

FIG. 12D shows a non-limiting perspective view of the cutting tool of the system of FIG. 12A attached to a cannula.

FIGS. 13A-13F show a sequence of steps of an exemplary method for implanting a connector and a medical device in a tissue wall, in accordance with one embodiment of the present invention as may be described herein.

Figure 14A:
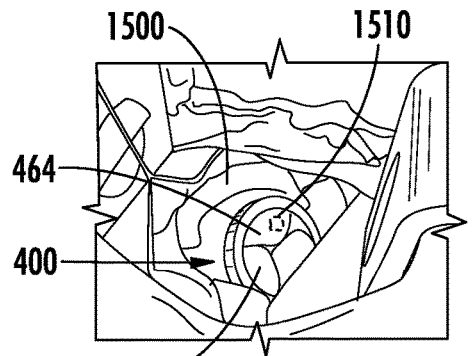

FIG. 14A shows a non-limiting view of an exemplary connector being implanted in a tissue wall of a heart.

Figures 14B, 14C, 14D:
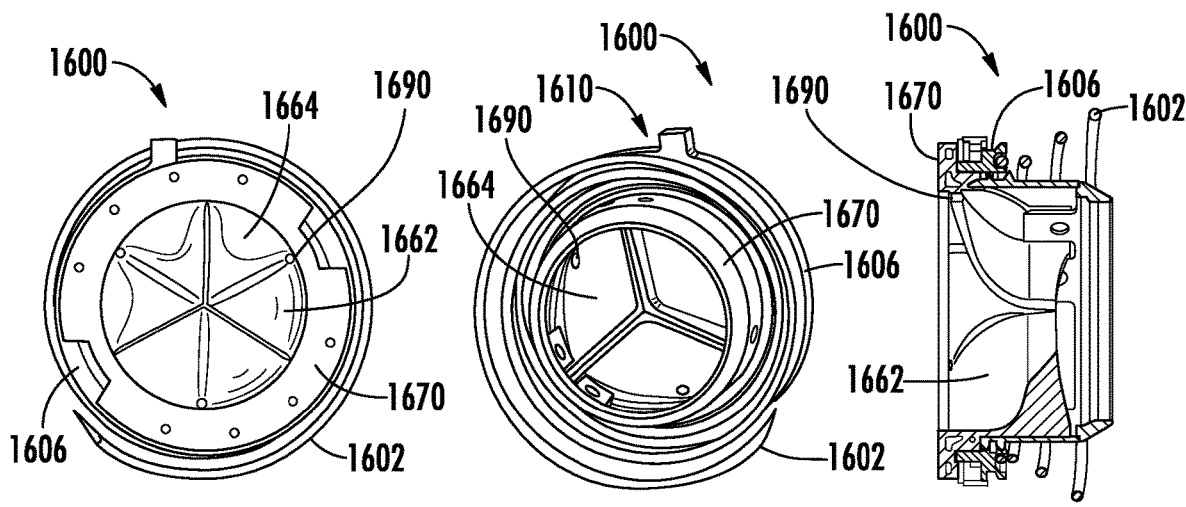

FIG. 14B shows a non-limiting top view of an exemplary connector for implanting and using in a tissue wall, in accordance with one embodiment of the present invention as may be described herein.

FIG. 14C shows a non-limiting perspective view of the connector of FIG. 14B.

FIG. 14D shows a non-limiting side cross-sectional view of the connector of FIG. 14B.

Figures 14E, 14F:
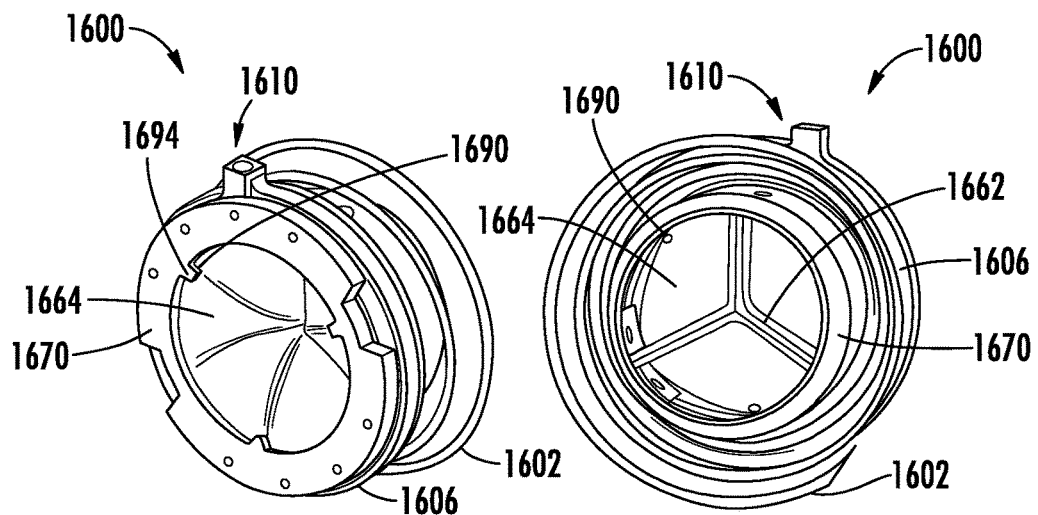

FIG. 14E shows a non-limiting perspective view of an exemplary connector for implanting and using in a tissue wall, in accordance with one embodiment of the present invention as may be described herein.

FIG. 14F shows a non-limiting perspective view of the connector of FIG. 14E.

FIG. 15A shows a non-limiting side cross-sectional view of an exemplary system for implanting and using in a heart including an intra-cardiac circulatory support system, in accordance with one embodiment of the present invention as may be described herein.

FIG. 15B shows a non-limiting perspective view of an anchoring device and an intra-ventricular VAD of the system of FIG. 15A implanted in a heart.

FIG. 15C shows a non-limiting perspective view of a plug of the system of FIG. 15A.

FIG. 15D shows a non-limiting perspective view of the plug of FIG. 15C.

Figure 16A:
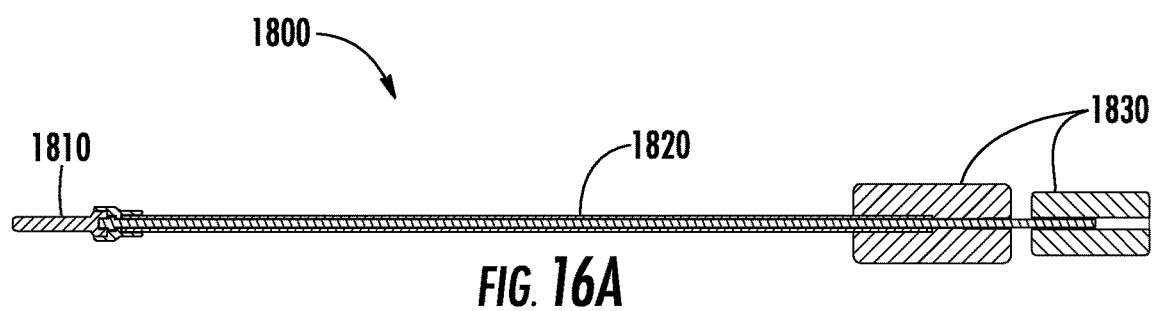
Figure 16B:
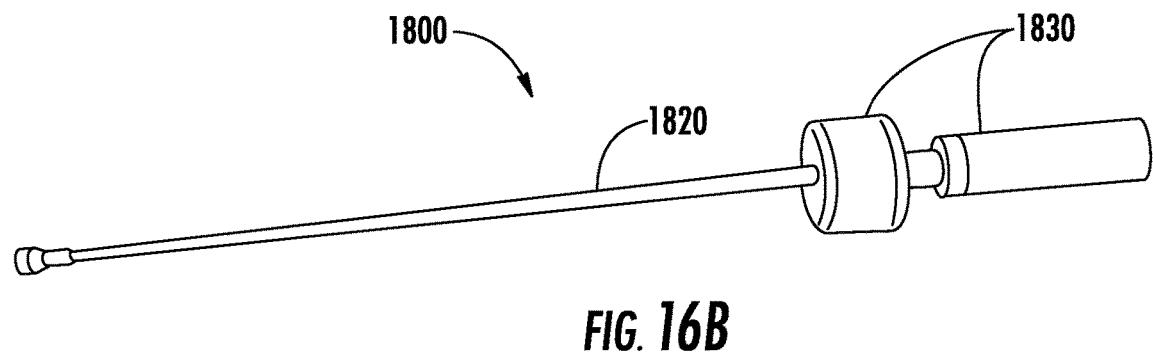

FIG. 16A shows a non-limiting side cross-sectional view of an exemplary flexible locking tool for use with a connector for implanting and using in a tissue wall, in accordance with one embodiment of the present invention as may be described herein FIG. 16B shows a non-limiting perspective view of the flexible locking tool of FIG. 16A.

Figure 17A:
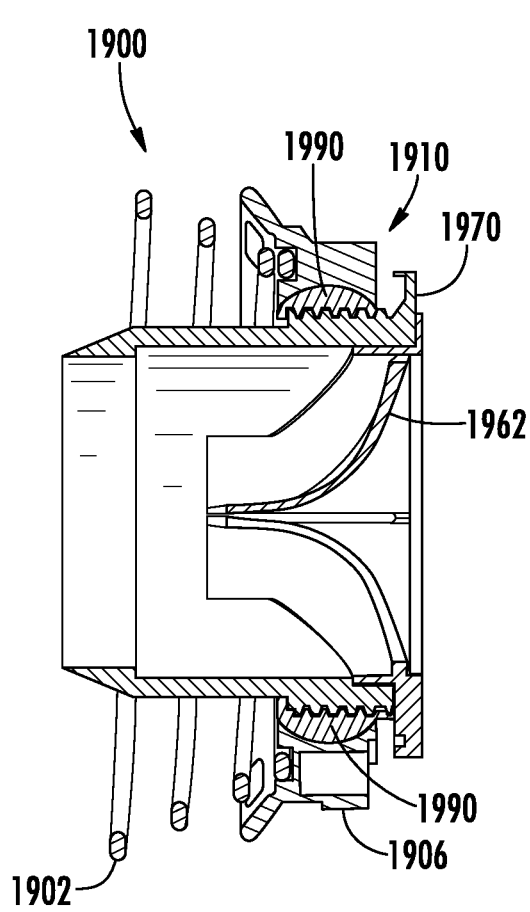

FIG. 17A shows a non-limiting side cross-sectional view of an exemplary connector for implanting and using in a tissue wall, in accordance with one embodiment of the present invention as may be described herein.

Figure 17B:
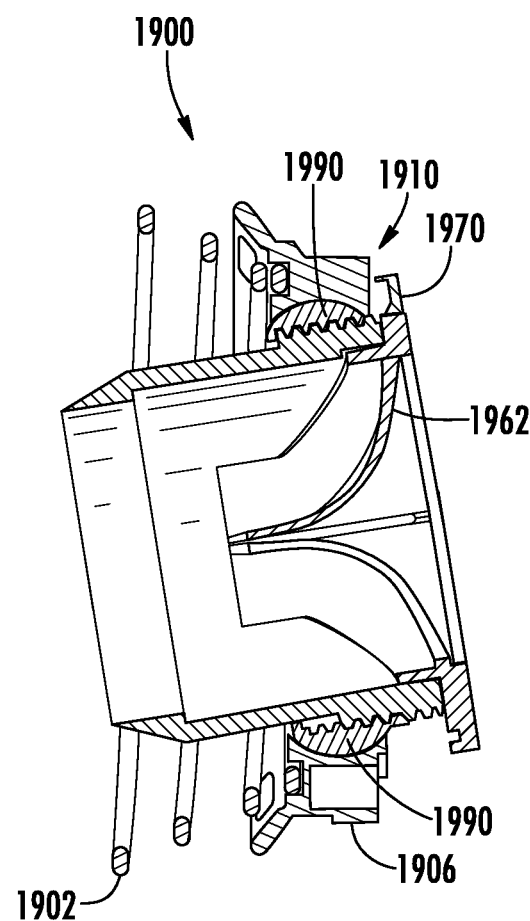

FIG. 17B shows a non-limiting side cross-sectional view of the connector of FIG. 17A.

DETAILED DESCRIPTION OF THE INVENTION

Embodiments of the present invention now will be described more fully hereinafter with reference to the accompanying drawings, in which some, but not all, embodiments of the inventions are shown. Indeed, the invention may be embodied in many different forms and should not be construed as limited to the embodiments set forth herein; rather, these embodiments are provided so that this disclosure will be thorough and complete, and will fully convey the scope of the invention to those skilled in the art. Like reference numbers refer to like elements throughout. The singular forms "a," "an," and "the" can refer to plural instances unless the context clearly dictates otherwise or unless explicitly stated.

Embodiments described herein provide devices, systems, and methods for implanting and using a connector in a tissue wall to establish, maintain, control, and close a fluid communication between opposing surfaces of the tissue wall. The embodiments may rely, in part, on the material characteristics of tissue to allow for the connector to establish, maintain, control, and close such fluid communication. In this manner, the geometric configuration and/or elastic properties of certain features of the embodiments may be utilized in combination with the material characteristics of the tissue and puncture site anatomy. Most soft tissues in the body are elastic, viscoelastic, and/or quasilinearelastic in nature, and therefore, are highly deformable under external loads or forces. Areas of cut, punctured, or disrupted tissue may therefore be deformed so as to manipulate the severed areas of tissue to establish, maintain, control, and close fluid communication between opposing surfaces of the tissue wall.

FIGS. 1A-1F illustrate an exemplary embodiment of a connector 100 (also referred to herein as a tissue connector or a heart connector) configured for implanting and using in a tissue wall to establish, maintain, control, and close a fluid communication between opposing surfaces of the tissue wall, as may be described herein. In this manner, the connector 100 may be utilized as a tissue connector configured for use in any number of surgical procedures, including, but not limited to, the example procedures described above. Specifically, the connector 100 may be utilized as a heart connector configured for use in various cardiac procedures, including, but not limited to implantation of an VAD. As is shown, the connector 100 may include an anchoring device 102, a port 106, and a coupler device 110. The anchoring device 102 may be configured for advancing at least partially into the tissue wall to secure the connector 100 for subsequent use during a surgical procedure.

The port 106 may be attached to a proximal end of the anchoring device 102 and may define an aperture 114 therethrough. In this manner, upon advancing a distal end of the anchoring device 102 at least partially into the tissue wall, the port 106 may be positioned against the tissue wall and the aperture 114 may provide access to the tissue wall for carrying out the procedure through the connector 100. The coupler device 110 may be positioned about the port 106 and may be configured for coupling various medical devices to the connector 100, as will be described in detail below. For example, the coupler device 110 may be configured for coupling various tubular medical devices having an outer diameter within the range of 10 mm and 30 mm, and more particularly within the range of 15 mm and 25 mm. An aperture 118 may be defined through the coupler device 110 for receiving such medical devices as well as various surgical tools that may be passed through the connector 100 to the tissue wall.

In certain aspects, the anchoring device 102 may include a helical coil or spring positioned about an axis of the connector 100. Accordingly, the anchoring device 102 may be configured for advancing at least partially into the tissue wall along a helical path defined by the coil or spring. In this manner, the anchoring device 102 provides a suture-less device for securing the connector 100 to the tissue wall. The distal end of the helical coil or spring may include a sharpened tip 122 configured for piercing a first surface (e.g., an outer surface) of the tissue wall upon contact and for allowing the helical coil or spring to then be easily advanced toward a second surface (e.g., an inner surface) of the tissue wall upon rotation of the connector 100. In this manner, the anchoring device 102 may be configured for advancing at least partially into the tissue wall such that at least a portion of the anchoring device 102 becomes disposed substantially between the first surface and the second surface of the tissue wall. Upon advancing the anchoring device 102 at least partially into the tissue wall, the helical coil or spring may provide support and reinforcement of the tissue wall. For example, the helical coil or spring may assist in preventing tearing or expansion of a hole subsequently formed in the tissue wall through the connector 100 during the surgical procedure. In certain aspects, the anchoring device 102 may include a plurality of helical coils or springs having sharpened tips 122 that are radially offset and equally spaced apart from one another. For example, the anchoring device 102 may include two helical coils or springs having tips 122 that are spaced 180-degrees apart, or three helical coils or springs having tips 122 that are spaced 120-degrees. In this manner the plurality of helical coils or springs may be configured to balance the anchoring device 102 in the tissue wall, and may enhance starting the anchoring device 102 in the tissue wall in a manner similar to that of a multi-start threadform.

In some aspects, as is shown in FIG. 1A, the helical coil or spring may be formed as a radially-expanding helical coil or spring having a helical diameter that increases from the proximal end toward the distal end of the anchoring device 102. In this manner, the helical coil or spring may have a conical shape such that the diameter of the distal end is substantially larger than the diameter of the proximal end. Due to the shape of the radially-expanding helical coil or spring, the anchoring device 102 may be configured to compress at least a portion of the tissue wall inward toward an axis of the anchoring device 102 when advanced therethrough. Such inward compression of the portion of the tissue wall may assist in securely attaching the connector 100 to the tissue wall. Moreover, such inward compression of the portion of the tissue wall may be utilized to compress tissue toward or against a conduit or other medical device that may be inserted through the connector 100 and through the hole formed in the tissue wall. In this manner, the compressed tissue may assist in securely positioning the conduit or medical device within the hole in the tissue wall and within an approximate center of the anchoring device 102. Additionally, the compressed tissue may provide a fluid tight seal between the tissue wall and an outer surface of the conduit or medical device. In other aspects, as is shown in FIG. 1D, the helical coil or spring may have a substantially constant helical diameter along the length of the anchoring device 102. In this manner, inward tissue compression caused by the anchoring device 102 may be limited to that resulting from tissue displacement caused by advancing the helical coil or spring into the tissue wall. Additional tissue compression, however, may be achieved between the helical coil or spring and the outer surface of the conduit or medical device, as described in detail below. Specifically, a hole may be formed in the tissue wall, the hole having a diameter less than an outer diameter of the conduit or medical device inserted therein. Accordingly, upon insertion, the conduit or medical device may compress at least a portion of the tissue wall radially outward toward the helical coil or spring. In still other aspects, the helical coil or spring may have a varying helical diameter along the length of the anchoring device 102, including radially-expanding portions and radially-contracting portions extending from the proximal end toward the distal end of the anchoring device 102. In this manner, tissue compression may vary along the thickness of the tissue wall according to the radially-expanding portions and radially contracting portions positioned therein. In some aspects, the helical coil or spring may have a varying pitch along the length of the anchoring device 102 and thus may be configured for axially compressing layers of the tissue.

In other aspects where the anchoring device 102 does not include a helical coil or spring, the anchoring device 102 may include non-helical elements, such as pins, prongs, barbs, hooks, staples, or other similar features, configured for advancing at least partially into the tissue wall to secure the connector 100 for subsequent use during a surgical procedure. In some such aspects, the anchoring device 102 may be configured to compress at least a portion of the tissue wall inward toward an axis of the anchoring device 102 when advanced therethrough, due at least in part to the configuration of the pins, prongs, barbs, hooks, staples, or other similar features. Such inward compression of the portion of the tissue may provide functional advantages similar to those described above with respect to the anchoring device 102 including the helical coil or spring. In some aspects, the anchoring device 102 may include a glue or adhesive configured for enhancing attachment of the anchoring device 102 to the tissue wall.

In certain aspects, the port 106 may be formed as a substantially ring-shaped member having a circumferential inner surface 126 and a circumferential outer surface 128. In this manner, the aperture 114 may be defined by the circumferential inner surface 126 of the port 106. As noted above, the port 106 may be attached to the proximal end of the anchoring device 102. Specifically, the port 106 may be rigidly attached to the proximal end of the anchoring device 102 such that axial rotation of the port 106 results in corresponding axial rotation of the anchoring device 102 for advancing the anchoring device 102 at least partially into the tissue wall. As is shown, the proximal end of the anchoring device 102 may be positioned within the aperture 114 of the port 106. In some aspects, the port 106 may include a flange 132 formed about the distal end of the port 106 and extending radially outward. Accordingly, the flange 132 may be configured for contacting the first surface of the tissue wall upon advancing the anchoring device 102 therethrough.

As is shown, the flange 132 may have a generally frusto-conical shape, and the proximal end of the anchoring device 102 may be positioned within the portion of the aperture 114 defined by the flange 132. In some aspects, the flange 132 may include a plurality of holes 134 defined through the flange 132 and arranged in a circumferential array about an axis of the port 106. The holes 134 may be utilized during certain procedures for suturing the port 106 to the tissue wall to provide additional fixation of the connector 100. In some aspects, the port 106 may include tool attachment features 138 formed on the circumferential outer surface 128 and configured for attaching various tools to the connector 100, as will be described in detail below. The tool attachment features 138 may be formed as protrusions or tabs extending axially along the port 106. In this manner, the protrusions or tabs may be configured for transferring torque from a delivery tool to the connector 100 for advancing the anchoring device 102 at least partially into the tissue wall. As is shown, the protrusions or tabs may be generally T-shaped and thus may be configured to be axially retained by various tools that may be attached to the connector 100.

In certain aspects, the coupler device 110 may include a taper lock mechanism 142 positioned about the proximal end of the port 106 and configured for axially coupling various medical devices to the connector 100. Specifically, the taper lock mechanism 142 may be configured for receiving and axially retaining a tube element of a medical device, such as an inlet tube of an LVAD or an AAC, positioned within the aperture 118 of the coupler device 110. In this manner, after advancing the anchoring device 102 at least partially into the tissue wall, the tube element may then be secured to the connector 100 via the coupler device 110, and thus the tube element may be secured to the tissue wall.

As is shown, the taper lock mechanism 142 may include a locking ring 144 including a plurality of fingers 146 positioned in a circumferential array and extending axially about the locking ring 144. Each finger 146 may include a tab 148 extending radially outward from the finger 146. At least a portion of each of the tabs 148 may be positioned within a circumferential groove 152 defined in the circumferential inner surface 126 of the port 106. Each of the tabs 148 may be angled radially inward toward a distal end of the finger 146 to ease insertion into the groove 152, as the tabs 148 may be configured for deflecting radially inward upon contact with the proximal end of the port 106. The groove 152 may include a tapered surface 154 angled radially inward toward the proximal end of the port 106. In this manner, the tabs 148 of the fingers 146 may face the tapered surface 154 of the groove 152. Based on this arrangement, the tube element of the medical device may be inserted into the aperture 118 and axially retained by the taper lock mechanism 142. Specifically, axial removal of the tube element may be prevented by interaction between the tabs 148 of the fingers 146 and the tapered surface 154 of the groove 152, which may deflect the fingers 146 radially inward and thus may increase frictional forces between the fingers 146 and the smooth outer surface of the tube element. Accordingly, the taper lock mechanism 142 may be configured for receiving and axially retaining the tube element within the aperture 118 without the need to provide any mating features on the outer surface of the tube element. In this manner, the taper lock mechanism 142 may be configured for coupling various medical devices to the connector 100, provided the mating tube elements have an outer diameter within a selected range. For example, the taper lock mechanism 142 may be configured for receiving and axially retaining tube elements having an outer diameter between 19 mm and 22 mm.

In certain aspects, the connector 100 also may include a secondary sealing element 158 configured for contacting and sealing against the first surface of the tissue wall upon advancing the anchoring device 102 therethrough. The secondary sealing element 158 may be formed as a substantially ring-shaped member attached to the distal end of the port 106 and extending radially. In some aspects, the secondary sealing element 158 may be formed as an O-ring configured for contacting and sealing against the first surface of the tissue wall. In other aspects, as is shown, the secondary sealing element 158 may be formed to have a generally frusto-conical shape extending radially outward and configured for receiving at least a portion of the tissue wall, particularly where the first surface of the tissue wall is curved in a substantially convex manner. In other aspects, the secondary sealing element 158 may be formed to have a generally frusto-conical shape extending radially inward and configured for being received by at least a portion of the tissue wall, particularly where the first surface of the tissue wall is curved in a substantially concave manner. In still other aspects, the secondary sealing element 158 may be formed to have other geometries, which may be selected depending upon the shape of the tissue wall into which the connector 100 may be implanted. Such geometries may include, but are not limited to, a hemispherical shape (e.g., for a substantially curved tissue wall), a substantially flat annular shape (e.g., for a substantially flat tissue wall), and other mating shapes.

In some aspects, the secondary sealing element 158 may be formed of a rigid or substantially rigid material and thus may be configured for biasing the tissue wall to conform to the geometry of the secondary sealing element 158 to provide a secondary seal. In other aspects, the secondary sealing element may be formed of a flexible or elastomeric material and thus may be configured for conforming to the shape of the tissue wall to provide a secondary seal. In this manner, when the conduit or other medical device is inserted through the connector 100 and through the hole formed in the tissue wall, the secondary sealing element 158 may be configured for providing a secondary fluid tight seal about the conduit or medical device, which may be in addition to the primary fluid tight seal provided by the anchoring device 102 compressing tissue against the conduit or medical device, as described above. Alternatively, in aspects where the anchoring device 102 is not configured to compress tissue inward, the secondary sealing element 158 may be configured for providing the only fluid tight seal about the hole or about the conduit or medical device. In some aspects, the secondary sealing element 158 may include an adhesive or chemical means applied to at least a portion of the secondary sealing element 158 to create or enhance the secondary seal against the first surface of the tissue wall.

In certain aspects, the connector 100 also may include a hemostasis valve 162 configured for closing fluid communication through the connector 100. As is shown, the hemostasis valve 162 may be positioned at least partially within the aperture 114 of the port 106 and may be attached to the circumferential inner surface 126. In certain aspects, the hemostasis valve 162 may be a passive valve. In other aspects, the hemostasis valve 162 may be an active valve. In some aspects, the hemostasis valve 162 may be formed as a one-way valve configured for preventing a flow of fluid through the aperture 114 from the distal end of the port 106 to the proximal end of the port 106. In this manner, after advancing the anchoring device 102 at least partially into the tissue wall and forming the hole in the tissue wall through the connector 100, the hemostasis valve 162 may prevent fluid contained by the tissue wall from flowing through the port 106. For example, when the connector 100 is utilized as a heart connector and attached to a cardiac tissue wall, the hemostasis valve 162 may prevent blood contained by the tissue wall from flowing through the port 106. In some aspects, as is shown, the hemostasis valve 162 may be formed as a multi-leaflet one-way valve including a plurality of leaflets 164 configured to open radially outward. In other aspects, the hemostasis valve 162 may be formed as a single-leaflet one-way valve including a single leaflet 164 configured to open and close. In still other aspects, the hemostasis valve 162 may be a diaphragm valve having an expanded, open configuration and a collapsed, closed configuration. According to some such aspects, the diaphragm valve may include a small orifice or slit defined therein and configured for selectively controlling fluid communication therethrough, and the diaphragm valve may be manipulated from the collapsed, closed configuration into the expanded, open configuration by expanding the orifice or slit. In some aspects, the diaphragm valve may include an aperture defined therein and configured for selectively controlling fluid communication therethrough, and the diaphragm valve may be manipulated between the collapsed, closed configuration and the expanded, open configuration by rotating at least a portion of the valve to open or close the aperture. Specifically, rotation of at least a portion of the diaphragm valve in a first direction may cause the aperture to open, and rotation of at least a portion of the diaphragm valve in an opposite, second direction may cause the aperture to close.

According to aspects where the hemostasis valve 162 has a one-way configuration, the hemostasis valve 162 may be configured for allowing various tools, conduits, or medical devices to be passed through the aperture 114 from the proximal end of the port 106 to the tissue wall. In some aspects, the hemostasis valve 162 may be formed of a flexible or elastic material, such as silicone, and thus may be elastically deformed by the tools, conduits, or medical devices passed through the aperture 114 to the tissue wall. In this manner, when the tool, conduit, or medical device is inserted through the connector 100, the hemostasis valve 162 may be configured for providing a fluid tight seal about an outer surface of the tool, conduit, or medical device. In certain aspects including the hemostasis valve 162, as is shown in FIGS. 1B and 1C, the hemostasis valve 162 may be positioned radially between the taper lock mechanism 142 and the tube element of the medical device that may be inserted through the aperture 114. In this manner, the frictional forces that retain the tube element are generated between the hemostasis valve 162 and the smooth outer surface of the tube element, instead of being generated directly between the fingers 146 and the smooth outer surface of the tube element. In some aspects, the hemostasis valve 162 may be formed of a flexible or elastic material, such as silicone, and thus may provide result in a high coefficient of friction between the hemostasis valve 162 and the tube element.

FIGS. 2A-2G illustrate another exemplary embodiment of a connector 200 configured for implanting and using in a tissue wall to establish, maintain, control, and close a fluid communication between opposing surfaces of the tissue wall, as may be described herein. The connector 200 may include various elements corresponding to those described above with respect to connector 100, which elements are identified in FIGS. 2A-2G with corresponding numerals and may not be described in further detail herein. The connector 200 may be utilized as a tissue connector configured for use in any number of surgical procedures, including, but not limited to, the example procedures described above. Specifically, the connector 200 may be utilized as a heart connector configured for use in various cardiac procedures, including, but not limited to implantation of a VAD. As is shown, the connector 200 may include an anchoring device 202, a port 206, and a coupler device 210, which may be configured in a manner similar to the corresponding elements of connector 100. Certain structural and functional differences between the connector 200 and the connector 100 will be described as follows.

In certain aspects, the coupler device 210 may include an axial clip mechanism 242 positioned about the proximal end of the port 206 and configured for axially coupling various medical devices to the connector 200. Specifically, the axial clip mechanism 242 may be configured for receiving and axially retaining a tube element of a medical device, such as an inlet tube of a VAD, positioned within the aperture 218 of the coupler device 210. In this manner, after advancing the anchoring device 202 at least partially into the tissue wall, the tube element may then be secured to the connector 200 via the coupler device 210, and thus the tube element may be secured to the tissue wall. As is shown, the axial clip mechanism 242 may include a clip ring 244 including a plurality of fingers 246 positioned in a circumferential array and extending axially about the clip ring 244. Each finger 246 may include a tab 248 extending radially inward from the finger 246. At least a portion of each of the tabs 248 may be configured for positioning within a circumferential groove 252 defined in the circumferential outer surface 228 of the port 206. The port 206 also may include a circumferential ring 253 formed on the circumferential outer surface 228 about the proximal end of the port 206. Specifically, the ring 253 may be positioned adjacent the groove 252 along the circumferential outer surface 228 of the port 206. The ring 253 may include a tapered surface 254 angled radially inward toward the proximal end of the port 206. Each of the tabs 248 may be angled radially outward toward a distal end of the finger 246 to ease advancing the tabs 248 over the ring 253 and into the groove 252, as the tabs 248 may be configured for deflecting radially outward upon contact with the tapered surface 254 of the ring 253. In this manner, upon positioning at least a portion of each of the tabs 248 within the groove 252, the clip ring 244 may be axially coupled to the port 206. The clip ring 244 may be configured for being secured to the tube element of the medical device prior to being coupled to the port 206. Specifically, the clip ring 244 may be configured for being sutured to a sewing cuff of the tube element of the medical device prior to being coupled to the port 206. The sewing cuff may be spaced apart from a distal end of the tube element. Based on this arrangement, after securing the clip ring 244 to the tube element, the tube element may then be inserted into the aperture 214 of the port 206 as the clip ring 244 is advanced toward the proximal end of the port 206. Upon coupling the clip ring 244 to the port 206, the tube element may be axially coupled to the connector 200, and thus the tube element may be secured to the tissue wall. It will be understood that, in other embodiments, the mating features of the axial clip mechanism 242 may be reversed such that the clip ring 244 may include the groove and ring, and the port 206 may include the fingers having tabs.

FIGS. 3A-3C illustrate another exemplary embodiment of a connector 300 configured for implanting and using in a tissue wall to establish, maintain, control, and close a fluid communication between opposing surfaces of the tissue wall, as may be described herein. The connector 300 may include various elements corresponding to those described above with respect to connector 100, which elements are identified in FIGS. 3A-3C with corresponding numerals and may not be described in further detail herein. The connector 300 may be utilized as a tissue connector configured for use in any number of surgical procedures, including, but not limited to, the example procedures described above. Specifically, the connector 300 may be utilized as a heart connector configured for use in various cardiac procedures, including, but not limited to implantation of a VAD. As is shown, the connector 300 may include an anchoring device 302, a port 306, and a coupler device 310, which may be configured in a manner similar to the corresponding elements of connector 100. Certain structural and functional differences between the connector 300 and the connector 100 will be described as follows.

In certain aspects, the coupler device 310 may include a worm gear collet mechanism 342 positioned about the proximal end of the port 306 and configured for axially coupling various medical devices to the connector 300. Specifically, the worm gear collet mechanism 342 may be configured for receiving and axially retaining a tube element of a medical device, such as an inlet tube of a VAD, positioned within the aperture 318 of the coupler device 310. In this manner, after advancing the anchoring device 302 at least partially into the tissue wall, the tube element may then be secured to the connector 300 via the coupler device 310, and thus the tube element may be secured to the tissue wall. Additionally, the worm gear collet mechanism 342 may be configured for preventing axial rotation of the tube element positioned within the aperture 318 of the coupler device 310. As is shown, the worm gear collet mechanism 342 may include a collet ring 344 including a plurality of fingers 346 positioned in a circumferential array and extending circumferentially about a circumferentially inner surface of the collet ring 344. Each finger 346 may include a fixed end attached to the collet ring 344 and a free end configured for deflecting radially. Each finger 346 also may include a tab 348 extending radially outward from the free end of the finger 348. The worm gear collet mechanism 342 also may include a locking ring 350 positioned within the collet ring 344 and configured for axially rotating relative to the collet ring 344. The locking ring 350 may include a plurality of tabs 352 positioned in a circumferential array and extending radially inward from a circumferentially inner surface of the locking ring 350. The locking ring 350 also may include a plurality of teeth 353 positioned in a circumferential array and extending axially along a circumferentially outer surface of the locking ring 350. The worm gear collet mechanism 342 further may include a worm gear 354 positioned within a pocket 355 defined in the collet ring 344. Specifically, the pocket 355 may be positioned adjacent the locking ring 350, and the worm gear 354 may engage the teeth 353 of the locking ring 350. The worm gear 354 may be configured for axially rotating within the pocket 355. In this manner, axial rotation of the worm gear 354 may result in axial rotation of the locking ring 350 about the axis of the coupler device 310. The worm gear 354 may include a driving feature, such as a female hexagonal socket or other known driving feature, configured for engaging and axially rotating the worm gear 354.

As is shown, the worm gear collet mechanism 342 may be configured for moving from an unlocked state to a locked state. When in the unlocked state, the tabs 348 of the fingers 346 of the collet ring 344 may be positioned outside of the aperture 318 of the coupler device 310, and the tabs 352 of the locking ring 350 may be positioned adjacent the tabs 348 of the fingers 346. Upon axially rotating the worm gear 354 in a first direction, the worm gear collet mechanism 342 may move from the unlocked state to the locked state. Specifically, upon axially rotating the worm gear 354 in the first direction, the locking ring 350 may rotate axially such that the tabs 352 of the locking ring 350 contact the tabs 348 of the fingers 346 and deflect the tabs 348 radially inward into the aperture 318 of the coupler device 310. Based on this arrangement, the tube element of the medical device may be inserted into the aperture 318 and axially retained by the worm gear collet mechanism 342. Specifically, the tube element may be inserted into the aperture 318 when the worm gear collet mechanism 342 is in the unlocked state, and after advancing the tube element through the hole formed in the tissue wall, the worm gear collet mechanism 342 may be moved to the locked state. When in the locked state, axial removal of the tube element may be prevented by frictional forces between the fingers 346 and the smooth outer surface of the tube element. Additionally, when in the locked state, axial rotation of the tube element relative to the coupler device 310 also may be prevented by such frictional forces. Accordingly, the worm gear collet mechanism 342 may be configured for receiving and axially retaining the tube element within the aperture 318 without the need to provide any mating features on the outer surface of the tube element. In this manner, the worm gear collet mechanism 342 may be configured for coupling various medical devices to the connector 300, provided the mating tube elements have an outer diameter within a selected range. For example, the worm gear collet mechanism 342 may be configured for receiving and axially retaining tube elements having an outer diameter between 19 mm and 22 mm.

FIGS. 4A-4I illustrate another exemplary embodiment of a connector 400 configured for implanting and using in a tissue wall to establish, maintain, control, and close a fluid communication between opposing surfaces of the tissue wall, as may be described herein. The connector 400 may include various elements corresponding to those described above with respect to connector 100, which elements are identified in FIGS. 4A-4I with corresponding numerals and may not be described in further detail herein. The connector 400 may be utilized as a tissue connector configured for use in any number of surgical procedures, including, but not limited to, the example procedures described above. Specifically, the connector 400 may be utilized as a heart connector configured for use in various cardiac procedures, including, but not limited to implantation of a VAD. As is shown, the connector 400 may include an anchoring device 402, a port 406, and a coupler device 410, which may be configured in a manner similar to the corresponding elements of connector 100. Certain structural and functional differences between the connector 400 and the connector 100 will be described as follows.

In certain aspects, the coupler device 410 may include a deflection arm mechanism 442 positioned about the proximal end of the port 406 and configured for axially coupling various medical devices to the connector 400. Specifically, the deflection arm mechanism 442 may be configured for receiving and axially retaining a tube element of a medical device, such as an inlet tube of an LVAD or an AAC, positioned within the aperture 418 of the coupler device 410. In this manner, after advancing the anchoring device 402 at least partially into the tissue wall, the tube element may then be secured to the connector 400 via the coupler device 410, and thus the tube element may be secured to the tissue wall. Additionally, the deflection arm mechanism 442 may be configured for preventing axial rotation of the tube element positioned within the aperture 418 of the coupler device 410. As is shown, the deflection arm mechanism 442 may include a base ring 444 extending circumferentially about the aperture 418. The deflection arm mechanism 442 also may include a deflection arm 446 formed substantially in the shape of an arc. The deflection arm 446 may be positioned in a mating slot 448 defined in the base ring 444 and extending along a circumferentially inner surface of the base ring 444. As is shown, the deflection arm 446 may include a fixed end 450 securely attached to the base ring 444 and a free end 451 configured for deflecting radially inward. The deflection arm mechanism 442 further may include a deflecting member 454 positioned within a mating hole 455 defined in the base ring 444. The deflecting member 454 may be configured for deflecting the deflection arm 446 inward. In some aspects, as is shown, the deflecting member 454 may be a threaded member, such as a screw or a bolt, positioned within the mating hole 455 defined in the base ring 444, which may also be threaded. Specifically, the mating hole 455 may be positioned adjacent the free end 451 of the deflection arm 446, and the deflecting member 454 may be configured for advancing through the mating hole 455 to contact a radially outward side of the free end 451 of the deflection arm 446. The deflecting member 454 may include a driving feature, such as a female hexagonal socket or other known driving feature, configured for engaging and axially rotating the threaded member 454 for advancement through the mating hole 455. In such aspects, the deflecting member 454 may be rotated by a simple tool, an attached wire, or a knob.

As is shown, the deflection arm mechanism 442 may be configured for moving from an unlocked state to a locked state. When in the unlocked state, the free end 451 of the deflection arm 446 may be positioned outside of the aperture 418 of the coupler device 410. Upon advancing the deflecting member 454 through the mating hole 455, the deflection arm mechanism 442 may move from the unlocked state to the locked state. Specifically, upon advancing the deflecting member 454 through the mating hole 455 and contacting the deflection arm 446, the free end 451 of the deflection arm 446 may deflect radially inward into the aperture 418 of the coupler device 410. Based on this arrangement, the tube element of the medical device may be inserted into the aperture 418 and axially retained by the deflection arm mechanism 442. Specifically, the tube element may be inserted into the aperture 418 when the deflection arm mechanism 442 is in the unlocked state, and after advancing the tube element through the hole formed in the tissue wall, the deflection arm mechanism 442 may be moved to the locked state. When in the locked state, axial removal of the tube element may be prevented by frictional forces between the deflection arm 446 and the smooth outer surface of the tube element, as well as frictional forces between the base ring 444 and the smooth outer surface of the tube element. Additionally, when in the locked state, axial rotation of the tube element relative to the coupler device 410 also may be prevented by such frictional forces. Accordingly, the deflection arm mechanism 442 may be configured for receiving and axially retaining the tube element within the aperture 418 without the need to provide any mating features on the outer surface of the tube element. In this manner, the deflection arm mechanism 442 may be configured for coupling various medical devices to the connector 400, provided the mating tube elements have an outer diameter within a selected range. For example, the deflection arm mechanism 442 may be configured for receiving and axially retaining tube elements having an outer diameter between 19 mm and 22 mm.

In certain aspects, the connector 400 also may include a cannula 470 configured for positioning through the aperture 414 of the connector 400 and through the tissue wall. Accordingly, the cannula 470 may provide a rigid member for positioning within the hole formed in the tissue wall. In this manner, the cannula 470 may be configured to stabilize the tissue positioned adjacent the hole and thus may prevent fluid leakage about the interface between the port 406 and the first surface of the tissue wall or between the secondary sealing member 458 and the first surface of the tissue wall.

In some aspects, as is shown, the connector 400 further may include a hemostasis valve 462 configured for closing fluid communication through the connector 400. Specifically, the hemostasis valve 462 may be positioned at least partially within the cannula 470 for closing fluid communication therethrough. In such aspects, the cannula 470 may include a lateral opening 474 configured to allow the deflection arm 446 of the deflection arm mechanism 442 to pass through the lateral opening 474 in order to engage and retain the tube element via the frictional forces generated between the hemostasis valve 462 and the smooth outer surface of the tube element. Additionally, the cannula 470 may include tool engagement features 478 configured for engaging various tools for delivering and positioning the cannula 470 within the connector 400. In some aspects, the coupler device 410 may be positioned on or within the cannula 470. In such aspects, the cannula 470 would not include the lateral opening 474 as described above. In certain aspects, as is shown in FIGS. 4C and 4D, the cannula 470 may include threads 482 formed on an outer surface of the cannula 470 and configured for engaging mating threads defined within the aperture 414 of the connector 400. In this manner, the cannula 470 may be securely positioned within the connector 400.

In some aspects, the deflection arm or cantilever 446 may be located on the port 406. In other aspects, the deflection arm 446 may be located on the cannula 470. In some embodiments, the deflection arm 446 may be actuated as to deflect and lock the inlet of the VAD or other medical device. In other embodiments, the deflection arm 446 may be actuated as to deflect and deform a portion of another component, such as a portion of the hemostasis valve 462, which would in turn lock the inlet of the VAD or other medical device. It is understood that several other elements or surfaces may be positioned between deflection arm 446 and the VAD inlet surface and that deflection of the deflection arm 446 may cause deflection, deformation, or other mechanical changes in these intermediate elements or surfaces, which may in turn lock the inlet of the VAD in place.

Independent of the primary locking mechanism, the friction between the hemostasis valve 462 and the inlet of the VAD may be enough for locking the VAD inlet in place. In some embodiments, the leaflets 464 or surfaces of the hemostasis valve 462 may serve as a Chinese finger trap. In these embodiments, the VAD inlet may be relatively free to move forward into the cavity or ventricle though the valve 462, but backward motion to retrieve the VAD may be reduced or totally limited by the geometrical configuration or friction of the contacting surfaces of the hemostasis valve 462.

FIGS. 5A-5F illustrate another exemplary embodiment of a connector 500 configured for implanting and using in a tissue wall to establish, maintain, control, and close a fluid communication between opposing surfaces of the tissue wall, as may be described herein. The connector 500 may include various elements corresponding to those described above with respect to connector 100, which elements are identified in FIGS. 5A-5F with corresponding numerals and may not be described in further detail herein. The connector 500 may be utilized as a tissue connector configured for use in any number of surgical procedures, including, but not limited to, the example procedures described above. Specifically, the connector 500 may be utilized as a heart connector configured for use in various cardiac procedures, including, but not limited to implantation of a VAD. As is shown, the connector 500 may include an anchoring device 502, a port 506, and a coupler device 510, which may be configured in a manner similar to the corresponding elements of connector 100. Certain structural and functional differences between the connector 500 and the connector 100 will be described as follows.

In certain aspects, the coupler device 510 may include a hinged ring lock mechanism 542 positioned about the proximal end of the port 506 and configured for axially coupling various medical devices to the connector 500. Specifically, the hinged ring lock mechanism 542 may be configured for receiving and axially retaining a tube element of a medical device, such as an inlet tube of an LVAD or an AAC, positioned within the aperture 518 of the coupler device 510. In this manner, after advancing the anchoring device 502 at least partially into the tissue wall, the tube element may then be secured to the connector 500 via the coupler device 510, and thus the tube element may be secured to the tissue wall. As is shown, the hinged ring lock mechanism 542 may include a first ring 544 formed about the proximal end of the port 506 and extending circumferentially about the aperture 518. The hinged ring lock mechanism 542 also may include a second ring 546 connected to the first ring 544 and extending circumferentially about the aperture 518. Specifically, the second ring 546 may be connected to the first ring 544 by a hinge 548 positioned along the circumferentially outer surfaces of the second ring 546 and the first ring 544. Accordingly, the second ring 546 may be configured to pivot about the hinge 548 relative to the first ring 544 and the remainder of the connector 500. Specifically, the second ring 546 may be configured to pivot from a closed position, in which the second ring 546 contacts and is coaxial with the first ring 544, to an open position, in which the second ring 546 is pivoted away from and is not coaxial with the first ring 544. In some aspects, the aperture defined by the second ring 546 may have an irregular shape (i.e., non-cylindrical) and may be configured to interfere with the tube of the medical device to be inserted into the aperture 518 of the coupler device 510. Additionally or alternatively, in some aspects, the hinged ring lock mechanism 542 may include a catch element 549, such as a deformable sleeve, positioned on the tube element and configured to interfere with the aperture defined by the second ring 546. Based on these arrangements, the tube element of the medical device may be inserted into the aperture 518 and axially retained by the hinged ring lock mechanism 542. Specifically, the tube element may be inserted into the aperture 518 when the second ring 546 is in the closed position, and axial removal of the tube element may be prevented by interaction between the tube element, the first ring 544, and the second ring 546, which may cause the second ring 546 to pivot to the open position. Because the second ring 546 is not coaxial with the first ring 544 when in the open position, such pivoting may increase frictional forces between the first ring 544 and the smooth outer surface of the tube element as well as frictional forces between the second ring 546 and the smooth outer surface of the tube element. Moreover, in aspects including the catch element 549, frictional forces may be enhanced by the catch element 549, which may be formed of an elastic and deformable material, such as silicone. Accordingly, the hinged ring lock mechanism 542 may be configured for receiving and axially retaining the tube element within the aperture 518 without the need to provide any mating features defined by the outer surface of the tube element. In this manner, the hinged ring lock mechanism 542 may be configured for coupling various medical devices to the connector 500, provided the mating tube elements have an outer diameter within a selected range. For example, the hinged ring lock mechanism 542 may be configured for receiving and axially retaining tube elements having an outer diameter between 19 mm and 22 mm. In some aspects, the connector 500 may include a hemostasis valve 562 configured to close a fluid communication therethrough. Specifically, as is shown, the hemostasis valve 562 may be formed as a diaphragm valve positioned within the aperture 514 of the connector 500. The diaphragm valve may be configured in a manner described above with respect to the hemostasis valve 162 of the connector 100.

FIGS. 6A-6D illustrate another exemplary embodiment of a connector 600 configured for implanting and using in a tissue wall to establish, maintain, control, and close a fluid communication between opposing surfaces of the tissue wall, as may be described herein. The connector 600 may include various elements corresponding to those described above with respect to connector 100, which elements are identified in FIGS. 6A-6D with corresponding numerals and may not be described in further detail herein. The connector 600 may be utilized as a tissue connector configured for use in any number of surgical procedures, including, but not limited to, the example procedures described above. Specifically, the connector 600 may be utilized as a heart connector configured for use in various cardiac procedures, including, but not limited to, implantation of a VAD. As is shown, the connector 600 may include an anchoring device 602, a port 606, and a coupler device 610, which may be configured in a manner similar to the corresponding elements of connector 100. Certain structural and functional differences between the connector 600 and the connector 100 will be described as follows.

In certain aspects, the coupler device 610 may include an axial clip and clamp mechanism 642 positioned about the proximal end of the port 606 and configured for axially coupling various medical devices to the connector 600. Specifically, the axial clip and clamp mechanism 642 may be configured for receiving and axially retaining a tube element of a medical device, such as an inlet tube of an LVAD or an AAC, positioned within the aperture 618 of the coupler device 610. In this manner, after advancing the anchoring device 602 at least partially into the tissue wall, the tube element may then be secured to the connector 600 via the coupler device 610, and thus the tube element may be secured to the tissue wall. As is shown, the axial clip and clamp mechanism 642 may include a clip ring 644 including a plurality of fingers 646 positioned in a circumferential array and extending axially about the clip ring 644. Each finger 646 may include a tab 647 extending radially inward from the finger 646. At least a portion of each of the tabs 647 may be configured for positioning within a circumferential groove 648 defined in the circumferential outer surface 628 of the port 606. The port 606 also may include a circumferential ring 649 formed on the circumferential outer surface 628 about the proximal end of the port 606. Specifically, the ring 649 may be positioned adjacent the groove 648 along the circumferential outer surface 628 of the port 606. The ring 649 may include a tapered surface 650 angled radially inward toward the proximal end of the port 606. Each of the tabs 647 may be angled radially outward toward a distal end of the finger 646 to ease advancing the tabs 647 over the ring 649 and into the groove 648, as the tabs 647 may be configured for deflecting radially outward upon contact with the tapered surface 650 of the ring 649. In this manner, upon positioning at least a portion of each of the tabs 647 within the groove 648, the clip ring 644 may be axially coupled to the port 606. The axial clip and clamp mechanism 642 also may include a plurality of clamp portions 651 positioned within and retained by the clip ring 644 and extending circumferentially about the aperture 618. Specifically, as is shown, the axial clip and clamp mechanism 642 may include two clamp portions 651 each extending along approximately half of the circumference of the aperture. The clamp portions 651 may be coupled to one another by threaded members 652 configured to engage mating threaded holes 653 defined in each of the clamp portions 651. The threaded members 652 each may include a driving feature, such as a female hexagonal socket or other known driving feature, configured for engaging and axially rotating the threaded members 652 for advancement through the threaded holes 653.

As is shown, the clamp portions 651 may be configured for moving from an unlocked state to a locked state. When in the unlocked state, the clamp portions 651 may be spaced apart from one another and the circumferentially inner surfaces of the clamp portions 651 may be positioned outside of the aperture 618 of the coupler device 610. Upon advancing the threaded members 652 through the threaded holes 653, the clamp portions 651 may move from the unlocked state to the locked state. Specifically, upon advancing the threaded members 652 through the threaded holes 653, the clamp portions 651 may move toward one another and the circumferentially inner surfaces of the clamp portions 651 may move into the aperture 618 of the coupler device 618. Based on this arrangement, the tube element of the medical device may be inserted into the aperture 618 and axially retained by the axial clip and clamp mechanism 642. Specifically, the tube element may be inserted into the aperture 618 when the clamp portions 651 are in the unlocked state, and after advancing the tube element through the hole formed in the tissue wall, the clamp portions 651 may be moved to the locked state. When in the locked state, axial removal of the tube element may be prevented by frictional forces between the circumferentially inner surfaces of the clamp portions 651 and the smooth outer surface of the tube element. Additionally, when in the locked state, axial rotation of the tube element relative to the coupler device 610 also may be prevented by such frictional forces. Accordingly, the axial clip and clamp mechanism 642 may be configured for receiving and axially retaining the tube element within the aperture 618 without the need to provide any mating features on the outer surface of the tube element. In this manner, the axial clip and clamp mechanism 642 may be configured for coupling various medical devices to the connector 600, provided the mating tube elements have an outer diameter within a selected range. For example, the axial clip and clamp mechanism 642 may be configured for receiving and axially retaining tube elements having an outer diameter between 19 mm and 22 mm. It will be appreciated that the coupler device 610 may instead be configured as a threaded clamp mechanism including mating threads instead of clip features on the ring 644 and the port 606. In this manner, such threads may provide a secure mechanism that may be progressively tightened to ensure a strong connection between the ring 644 and the port 606.

In certain aspects, the connector 600 also may include a hemostasis valve 662 configured for closing fluid communication through the connector 600. As is shown, the hemostasis valve 662 may be formed as a tubular membrane extending axially between the port 606 and the clamp portions 651 of the coupler device 610. Specifically, a distal end of the hemostasis valve 662 may be attached to the proximal end of the port 606, and a proximal end of the hemostasis valve 662 may be attached to the proximal ends of the clamp portions. The hemostasis valve 162 may be formed of a flexible or elastic material and thus may be configured for moving from an expanded state, when the deformed and compressed when the clip ring 644 is separated from the port 606, to a compressed state, when the clip ring 644 is attached to the port 606. Moreover, when the hemostasis valve 162 is in the expanded state, a surgical clamp or similar tool may be placed over a portion of the hemostasis valve 162 to close fluid communication therethrough. In this manner, after advancing the anchoring device 602 at least partially into the tissue wall and forming the hole in the tissue wall through the connector 600, the hemostasis valve 662 may be clamped to prevent fluid contained by the tissue wall from flowing through the connector 600. For example, when the connector 600 is utilized as a heart connector and attached to a cardiac tissue wall, the clamped hemostasis valve 662 may prevent blood contained by the tissue wall from flowing through the connector 600. Moreover, based on its flexible or elastic nature, the hemostasis valve 662 may be elastically deformed by tools, conduits, or medical devices passed through the connector 600 to the tissue wall. In this manner, when the tool, conduit, or medical device is inserted through the connector 600, the hemostasis valve 662 may be configured for providing a fluid tight seal about an outer surface of the tool, conduit, or medical device.

In certain aspects, the connector 600 also may include a cannula 670 configured for extending at least partially through the hole formed in the tissue wall to establish fluid communication between the first surface and the second surface of the tissue wall. As is shown, the cannula 670 may be positioned within and extend through the aperture 614 of the port 606. In some aspects, the cannula 670 may be axially coupled to the port 606 and may be configured for axially rotating relative to the port 606. In such aspects, a proximal end of the cannula 670 may be attached to the distal end of the hemostasis valve 662, as is shown. In this manner, the hemostasis valve 662 and the clip ring 644 also may be configured for axially rotating relative to the port 606, along with the cannula 670.

FIGS. 6E-6H illustrate additional exemplary embodiments of a connector 600 configured for implanting and using in a tissue wall to establish, maintain, control, and close a fluid communication between opposing surfaces of the tissue wall, as may be described herein, which embodiments may include certain structural and functional differences between the as compared to the other connectors disclosed herein. For example, some such embodiments may include a hemostasis element 662 formed as an O-ring, as is shown in FIGS. 6E and 6F. Additionally, some such embodiments may include a coupler device 610 including a keyed locking mechanism for attaching a locking ring to the port 606, as is shown in FIG. 6G. Further, some such embodiments may include a coupler device 610 including a threaded mechanism for actuating a collet configured to retain a tube element of a medical device, as shown in FIG. 6H. Additional features shown in FIGS. 6E-6H will be appreciated by one having skill in the art.

FIGS. 7A-7B illustrate an exemplary embodiment of a delivery tool 700 configured for implanting a connector, such as the connector 400, in the tissue wall. The delivery tool 700 may include a connector interface 702, an elongated shaft 706, and a handle 710. The connector interface 702 may be positioned about a distal end of the delivery tool 700 and may be configured for attaching to and retaining the connector 400 for implanting in the tissue wall. For example, the connector interface 702 may be configured for attaching to and retaining the connector 400 by mechanical, chemical, or magnetic means. The handle 710 may be positioned about a proximal end of the delivery tool 700 and may be configured for being grasped by a user to guide the attached connector 400 toward the tissue wall and to then advance the anchoring device 402 at least partially into the tissue wall. Accordingly, the handle 710 may include various grip features or shapes, as is shown, to assist the user in implanting the connector 400, particularly where the anchoring device 402 includes a helical coil or spring and thus is advanced into the tissue wall by rotation. The elongated shaft 706 may extend axially between the connector interface 702 and the handle 710. In some aspects, the elongated shaft 706 and the handle 710 may be cannulated, and thus the delivery tool 700 may be configured for implanting the connector 400 over a guide wire.

As is shown, the connector interface 702 may include a ring-shaped receptacle 714 configured for receiving at least a portion of the connector 400. Specifically, the receptacle 714 may define a counterbore 718 configured for receiving at least a portion of the port 406. The receptacle 714 also may define one or more slots 722 extending radially through a circumferential wall 724 of the receptacle. Specifically, the receptacle 714 may define a plurality of slots 722 configured for receiving the tool attachment features 438 of the port 406. In this manner, the slots 722 may be configured for transferring torque from the delivery tool 700 to the connector 400 for advancing the anchoring device 402 at least partially into the tissue wall. In some aspects, as is shown, the slots 722 may be formed to be substantially J-shaped. Accordingly, each tool attachment feature 138 may be inserted axially into one of the slots 722, and the port 406 may be axially rotated such that the tool attachment features 438 are axially retained within the slots 722. In this manner, the receptacle 714 may be configured for axially retaining the connector 400 via the slots 722. In some aspects, the slots 722 of the receptacle 714 and the tool attachment features 438 of the port 406 may be configured for having an interference fit. Accordingly, upon inserting the portion of the port 406 into the counterbore 718 of the receptacle 714, the connector 400 may be axially retained by the delivery instrument 700 until a sufficient axial removal force is applied. In other aspects, the receptacle 714 may include a retention element configured for axially retaining the connector 400 within the counterbore 718. For example, the retention element may include a threaded member configured for contacting the circumferential outer surface 428 of the port 406. Alternatively, the retention element 726 may include a deflection arm configured for contacting either the circumferential outer surface 428 or one of the tool attachment features 438 of the port 406. In this manner, the receptacle 714 may be configured for axially retaining the connector 400 for implanting in the tissue wall.

FIGS. 8A-8B illustrate an exemplary embodiment of a cutting tool 800 configured for forming the hole in the tissue wall. The cutting tool 800 may include a coring device 802 and a piercing device 806. The coring device 802 may include a coring tube 810 positioned at a distal end of the coring device 802, and a coring handle 812 positioned at a proximal end of the coring device 802. The coring tube 810 may be removeably connected to the coring handle 812, for example by threads, such that different coring tubes 810 of different outer diameter sizes may be used in the cutting tool 800 for forming the hole to have a desired size. In certain aspects, the outer diameter of the distal end of the coring tube 810 may be selected to match the outer diameter of the tube element of the medical device to be positioned through the tissue wall. Accordingly, the hole formed may provide a close fit around the tube element. In other aspects, the outer diameter of the distal end of the coring tube 810 may be selected to be smaller than the outer diameter of the tube element, such that the undersized hole may assist in providing a fluid tight seal about the tube element. In still other aspects, the outer diameter of the distal end of the coring tube 810 may be selected to be larger than the outer diameter of the tube element, such that the oversized hole may allow the tube element to be easily positioned within the hole and also may allow the anchoring device to provide a fluid tight seal about the tube element by tissue compression.

As is shown, both the coring tube 810 and the coring handle 812 may be cannulated, and a portion of the piercing device 806 may be positioned therethrough. The piercing device 806 may include a piercing element 820, an elongated shaft 824, and a piercing handle 828. The piercing element 820 may be positioned at a distal end of the piercing device 806, the piercing handle 828 may be positioned at a proximal end of the piercing device 806, and the elongated shaft 824 may extend axially between the piercing element 820 and the piercing handle 828. The piercing element 820 may include a sharpened tip 832 configured for piercing the tissue wall and advancing therethrough. In some aspects, as is shown, the piercing element 820 may be formed in the shape of an arrowhead, although other shapes may be used. In this manner, the piercing element 820 may be configured for advancing along a straight path through the tissue wall. The piercing device 806 also may include an expandable element 836 positioned adjacent the piercing element 820. Specifically, as is shown, the expandable element 836 may be positioned along the elongated shaft 824 and adjacent a proximal end of the piercing element 820. The expandable element 836 may be configured for expanding from a laterally contracted state to a laterally expanded state, in which the lateral cross-sectional area is substantially equal to the inner diameter of the coring tube 810. As is shown, the expandable element 836 may include a plurality of pivotable plates 840 configured for pivoting from an axial position to a lateral position. Alternatively, the expandable element 836 may include an expandable balloon. The piercing device 806 further may include a stop ring 844 positioned along the elongated shaft 824 and adjacent the piercing handle 828. Specifically, as is shown, the stop ring 844 may be positioned along the elongated shaft 824 and adjacent a distal end of the piercing handle 828. The stop ring 844 may be configured for limiting translation of the piercing device 806 through the coring device 802. In some aspects, the entire cutting tool 800 may be cannulated and thus may be configured for use over a guide wire.

After securing a connector, such as the connector 100, to the tissue wall, the cutting tool 800 may be used to form the hole in the tissue wall. Initially, the piercing element 820 and the distal end of the coring tube 810 may be inserted into the aperture 114 of the port 106. Next, a portion of the piercing device 806 may be advanced through the coring device 802 such that the piercing element 820 may pierce the first surface of the tissue wall, and the piercing element 820 and the expandable element 836 may be advanced therethrough beyond the second surface of the tissue wall. The expandable element 836 may then be expanded from the contracted state to the expanded state and may be drawn against the second surface of the tissue wall. Next, the piercing device 806 may be retracted relative to the coring device 802 such that the expandable element 836 and the coring tube 810 form the hole in the tissue wall by removing a tissue core from the tissue wall. The piercing device 806 may be further retracted relative to the coring device 802 such that the expandable element 836 and the tissue core are positioned within the coring handle 812. In this manner, the expandable element 836 may be configured for retrieving the tissue core from the tissue wall. In certain aspects, the coring handle 812 may be formed from a transparent or translucent material such that complete removal of the tissue core from the tissue wall and the connector 100 may be visually confirmed through the coring handle 812. Finally, the cutting tool 800 may be removed from the connector 100.

FIGS. 9A-9C illustrate another exemplary embodiment of a cutting tool 900 configured for forming the hole in the tissue wall. The cutting tool 900 may include a coring device 902 and a piercing device 906. The coring device 902 may include a coring tube 910 positioned at a distal end of the coring device 902, and a coring handle 912 positioned at a proximal end of the coring device 902. The coring tube 910 may be removeably connected to the coring handle 912, for example by threads, such that different coring tubes 910 of different outer diameter sizes may be used in the cutting tool 900 for forming the hole to have a desired size. As is shown, both the coring tube 910 and the coring handle 912 may be cannulated, and a portion of the piercing device 906 may be positioned therethrough. The piercing device 906 may include a piercing element 920, an elongated shaft 924, and a piercing handle 928. The piercing element 920 may be positioned at a distal end of the piercing device 906, the piercing handle 928 may be positioned at a proximal end of the piercing device 906, and the elongated shaft 924 may extend axially between the piercing element 920 and the piercing handle 928. The piercing element 920 may include a sharpened tip 932 configured for piercing the tissue wall and advancing therethrough. In some aspects, as is shown, the piercing element 920 may be formed in the shape of a helical coil or spring, although other shapes may be used. In this manner, the piercing element 920 may be configured for advancing along a helical path through the tissue wall. The helical coil or spring may have an outer diameter that is substantially equal to the inner diameter of the coring tube 910. The coring device 902 further may include a stop ring 944 positioned at a proximal end of the coring handle 912. As is shown, the stop ring 944 may be configured for limiting translation of the piercing device 906 through the coring device 902.

After securing a connector, such as the connector 100, to the tissue wall, the cutting tool 900 may be used to form the hole in the tissue wall. Initially, the piercing element 920 and the distal end of the coring tube 910 may be inserted into the aperture 114 of the port 106. Next, a portion of the piercing device 906 may be advanced through the coring device 902 such that the piercing element 920 may pierce the first surface of the tissue wall, and the piercing element 920 may be advanced along a helical path therethrough beyond the second surface of the tissue wall. Next, the piercing device 906 may be retracted relative to the coring device 902 such that the piercing element 920 and the coring tube 910 form the hole in the tissue wall by removing a tissue core from the tissue wall. Alternatively, the coring device 902 may be advanced over the piercing device 906 such that the piercing element 920 and the coring tube 910 form the hole in the tissue wall by removing a tissue core from the tissue wall. The piercing device 906 then may be further retracted relative to the coring device 902 such that the piercing element 920 and the tissue core are positioned within the coring handle 912. In this manner, the piercing element 920 may be configured for retrieving the tissue core from the tissue wall. In certain aspects, the coring handle 912 may be formed from a transparent or translucent material such that complete removal of the tissue core from the tissue wall and the connector 100 may be visually confirmed through the coring handle 912. Finally, the cutting tool 900 may be removed from the connector 100.

FIGS. 10A-10C illustrate an exemplary embodiment of a combination tool 1000 configured for implanting the connector 100 and forming the hole in the tissue wall. Specifically, the combination tool 1000 may include a delivery device 1002 configured for implanting the connector 100, and a cutting device 1006 configured for forming the hole in the tissue wall. As is shown, a portion of the cutting device 1006 may be positioned within the delivery device 1002. In some aspects, the delivery device 1002 and the cutting device 1006 may be configured for rotating axially relative to one another. Moreover, in some aspects, the delivery device 1002 and the cutting device 1006 may be configured for translating axially relative to one another. However, in some such aspects, the delivery device 1002 and the cutting device 1006 may be configured for limiting a range of axial translation.

In certain aspects, as is shown, the delivery device 1002 may include a connector interface 1012, an elongated shaft 1016, and a handle 1020. The connector interface 1012 may be positioned about a distal end of the delivery device 1002 and may be configured for attaching to and retaining the connector 100 for implanting in the tissue wall. For example, the connector interface 1002 may be configured for attaching to and retaining the connector 100 by mechanical, chemical, or magnetic means. The handle 1020 may be positioned about a proximal end of the delivery device 1020 and may be configured for being grasped by a user to guide the attached connector 100 toward the tissue wall and to then advance the anchoring device 102 at least partially into the tissue wall. Accordingly, the handle 1020 may include various grip features or shapes to assist the user in implanting the connector 100, particularly where the anchoring device 102 includes a helical coil or spring and thus is advanced into the tissue wall by rotation. The elongated shaft 1016 may extend axially between the connector interface 1012 and the handle 1020.

As is shown, the connector interface 1012 may include a bore 1022 defined in a distal end of the elongated shaft 1016 and configured for receiving at least a portion of the connector 100. Specifically, the bore 1022 may be configured for receiving at least a portion of the port 106. The connector interface 1012 also may include a plurality of driving tabs 1024 positioned in a circumferential array and extending axially about the distal end of the elongated shaft 1016. The driving tabs 1024 may be configured for engaging the tool attachment features 138 of the port 106. Specifically, each of the driving tabs 1024 may be configured for positioning between adjacent tool attachment features 138 of the port. In this manner, the driving tabs 1024 may be configured for transferring torque from the delivery device 1002 to the connector 100 for advancing the anchoring device 102 at least partially into the tissue wall. In aspects where the tool attachment features 138 of the port 106 are generally T-shaped, as is shown, the driving tabs 1024 may be configured for laterally engaging the laterally extending portions of the tool attachment features 138 to facilitate such transfer of torque.

The connector interface 1012 further may include a locking ring 1028 positioned about the distal end of the elongated shaft 1016. The locking ring 1028 may be configured for receiving and engaging at least a portion of the connector 100. Specifically, the locking ring 1028 may define a bore 1032 configured for receiving at least a portion of the port 106. Additionally, the locking ring 1028 may include a plurality of locking tabs 1036 positioned in a circumferential array and extending axially about a distal end of the locking ring 1028. The locking tabs 1036 also may extend radially inward over a portion of the bore 1032. As is shown, the locking tabs 1036 may be configured for engaging the tool attachment features 138 of the port 106. Specifically, each of the locking tabs 1036 may be configured for positioning distally of a portion of at least one of the tool attachment features 138 of the port 106. In this manner, the connector interface 1012 may be configured for axially retaining the connector 100 via the locking tabs 1036. In aspects where the tool attachment features 138 of the port 106 are generally T-shaped, as is shown, the locking tabs 1036 may be configured for distally engaging the laterally extending portions of the tool attachment features 138 to facilitate such axial retention.

As is shown, the locking ring 1028 may be configured for moving from an unlocked position to a locked position. Specifically, the locking ring 1028 may be configured for axially rotating and translating relative to the elongated shaft 1016 from the unlocked position to the locked position. Such axial rotation and translation of the locking ring 1028 relative to the elongated shaft 1016 may be facilitated by guide pins 1040 extending radially inward from the locking ring 1028 and mating guide channels 1044 defined in the outer surface of the elongated shaft 1016. When in the unlocked position, the locking tabs 1036 of the locking ring 1028 are circumferentially aligned with and axially offset from the driving tabs 1024 of the elongated shaft 1016. Accordingly, the connector interface 1012 may receive the connector 100 when the locking ring 1028 is in the unlocked position, as the tool attachment features 138 may be inserted between the axially aligned locking tabs 1036 and driving tabs 1024. When in the locked position, the locking tabs 1036 of the locking ring 1028 are circumferentially offset from and axially overlapping with the driving tabs 1024 of the elongated shaft 1016. Accordingly, the connector interface 1012 may retain the connector 100 when the locking ring 1028 is in the unlocked position, as the tool attachment features 138 may be axially restricted by the locking tabs 1036 and rotatably restricted by the driving tabs 1024. In this manner, the connector interface 1012 may be configured for retaining the connector 100 for implanting in the tissue wall.

In certain aspects, as is shown, the cutting device 1006 may include a coring device 1050 and a piercing device 1054. The coring device 1050 may include a coring tube 1058 positioned at a distal end of the coring device 1050, and a coring handle 1062 positioned at a proximal end of the coring device 1050. The coring tube 1058 may be removeably connected to the coring handle 1062, for example by threads, such that different coring tubes 1058 of different outer diameter sizes may be used in the cutting device 1006 for forming the hole to have a desired size. As is shown, both the coring tube 1058 and the coring handle 1062 may be cannulated, and a portion of the piercing device 1054 may be positioned therethrough. The piercing device 1054 may include a piercing element 1066, an elongated shaft 1068, and a piercing handle 1070. The piercing element 1066 may be positioned at a distal end of the piercing device 1054, the piercing handle 1070 may be positioned at a proximal end of the piercing device 1054, and the elongated shaft 1068 may extend axially between the piercing element 1066 and the piercing handle 1070. The piercing element 1066 may include a sharpened tip 1072 configured for piercing the tissue wall and advancing therethrough. In some aspects, as is shown, the piercing element 1066 may be formed in the shape of an arrowhead, although other shapes may be used. In this manner, the piercing element 1066 may be configured for advancing along a straight path through the tissue wall. The piercing device 1054 also may include an expandable element 1076 positioned adjacent the piercing element 1066. Specifically, as is shown, the expandable element 1076 may be positioned along the elongated shaft 1068 and adjacent a proximal end of the piercing element 1066. The expandable element 1076 may be configured for expanding from a laterally contracted state to a laterally expanded state, in which the lateral cross-sectional area is substantially equal to the inner diameter of the coring tube 1058. As is shown, the expandable element 1076 may include a plurality of pivotable plates 1078 configured for pivoting from an axial position to a lateral position. Alternatively, the expandable element 1076 may include an expandable balloon.

After securing the connector 100 to the tissue wall via the delivery device 1002, the cutting device 1006 may be used to form the hole in the tissue wall. Initially, the piercing element 1066 and the distal end of the coring tube 1058 may be inserted into the aperture 114 of the port 106. Next, a portion of the piercing device 1054 may be advanced through the coring device 1050 such that the piercing element 1066 may pierce the first surface of the tissue wall, and the piercing element 1066 and the expandable element 1076 may be advanced therethrough beyond the second surface of the tissue wall. The expandable element 1076 may then be expanded from the contracted state to the expanded state and may be drawn against the second surface of the tissue wall. Next, the piercing device 1054 may be retracted relative to the coring device 1050 such that the expandable element 1076 and the coring tube 1058 form the hole in the tissue wall by removing a tissue core from the tissue wall. The piercing device 1054 may be further retracted relative to the coring device 1050 such that the expandable element 1076 and the tissue core are positioned within the coring handle 1062. In certain aspects, the coring handle 1062 may be formed from a transparent or translucent material such that complete removal of the tissue core from the tissue wall and the connector 100 may be visually confirmed through the coring handle 1062. Finally, the locking ring 1028 may be moved to the unlocked position, and the combination tool 1000 may be disengaged from the connector 100.

FIGS. 11A-11D illustrate another exemplary embodiment of a combination tool 1100 configured for implanting the connector 200 and forming the hole in the tissue wall. The combination tool 1100 may include various elements corresponding to those described above with respect to combination tool 1000, which elements are identified in FIGS. 11A-11D with corresponding numerals and may not be described in further detail herein. As is shown, the combination tool 1100 may include a delivery device 1102 configured for implanting the connector 200, and a cutting device 1106 configured for forming the hole in the tissue wall, which may be configured in a manner similar to the corresponding devices of the combination tool 1000. Certain structural and functional differences between the combination tool 1100 and the combination tool 1000 will be described as follows.

In certain aspects, as is shown, the delivery device 1102 may include a connector interface 1112, an elongated shaft 1116, and a handle 1120. The connector interface 1112 may be positioned about a distal end of the delivery device 1102 and may be configured for attaching to and retaining the connector 200 for implanting in the tissue wall. The handle 1120 may be positioned about a proximal end of the delivery device 1120 and may be configured for being grasped by a user to guide the attached connector 200 toward the tissue wall and to then advance the anchoring device 202 at least partially into the tissue wall. Accordingly, the handle 1120 may include various grip features or shapes to assist the user in implanting the connector 200, particularly where the anchoring device 202 includes a helical coil or spring and thus is advanced into the tissue wall by rotation. The elongated shaft 1116 may extend axially between the connector interface 1112 and the handle 1120.

As is shown, the connector interface 1112 may include a bore 1122 defined in a distal end of the elongated shaft 1116 and configured for receiving at least a portion of the connector 200. Specifically, the bore 1122 may be configured for receiving at least a portion of the port 206. The connector interface 1112 also may include a plurality of retaining fingers 1124 positioned in a circumferential array and extending axially about the distal end of the elongated shaft 1116. Each of the retaining fingers 1124 may include a retaining tab 1125 extending radially inward from the retaining finger 1124. At least a portion of each of the retaining tabs 1125 may be configured for positioning within the circumferential groove 252 of the port 206. Each of the retaining tabs 1125 may be angled radially outward toward a distal end of the retaining finger 1124 to ease advancing the retaining tabs 1125 over the ring 253 and into the groove 252, as the retaining tabs 1125 may be configured for deflecting radially outward upon contact with the tapered surface 254 of the ring 253. In this manner, upon positioning at least a portion of each of the retaining tabs 1125 within the groove 252, the port 206 may be axially retained by the connector interface 1112.

The connector interface 1112 further may include a driving ring 1128 positioned about the distal end of the elongated shaft 1116. The driving ring 1128 may be configured for receiving and engaging at least a portion of the connector 200. Specifically, the driving ring 1128 may define a bore 1132 configured for receiving at least a portion of the port 206. Additionally, the driving ring 1128 may include a plurality of driving tabs 1136 positioned in a circumferential array and extending axially about a distal end of the driving ring 1128. As is shown, the driving tabs 1136 may be configured for engaging the tool attachment features 238 of the port 206. Specifically, each of the driving tabs 1136 may be configured for positioning between adjacent tool attachment features 238 of the port. In this manner, the driving tabs 1136 may be configured for transferring torque from the delivery device 1102 to the connector 200 for advancing the anchoring device 202 at least partially into the tissue wall. The driving ring 1128 may be coupled to the elongated shaft 1116 and may be configured for axially rotating upon axial rotation of the elongated shaft 1116. In this manner, the driving tabs 1136 may be configured for transferring torque from the handle 1120 to the connector 200 for advancing the anchoring device 202 at least partially into the tissue wall.

FIGS. 12A-12D illustrate an exemplary system configured for implanting a connector 400 and forming a hole in a tissue wall. As is shown, the connector 400 may include the cannula 470 having the hemostasis valve 462 positioned therein. The system may include a delivery tool 1200 and a cutting tool 1300, which may include various elements corresponding to those described above with respect to delivery tool 700 and cutting tool 800, respectively. Certain structural and functional differences will be described as follows. In some aspects, the cutting tool 1300 may include one or more buttons configured for actuating the expandable element 1336. For example, the cutting tool 1300 may include a first button 1350 configured for expanding the expandable element 1336 from the laterally contracted state to the laterally expanded stare in order to subsequently form the hole in the tissue wall in the manner described above. In certain aspects, such expansion may be spring-loaded. Further, the cutting tool 1300 may include a second button 1354 configured for retracting the expandable element 1336 into the cutting tool 1300 in order to form the hole in the wall in the manner described above. In certain aspects, such retraction may be spring-loaded. In some aspects, as is shown in FIG. 12B, the entire cutting tool 1300 may be cannulated such that the cutting tool 1300 may be used over a guide wire. Additionally, the cutting tool 1300 may include mating features 1360 configured for engaging the tool engagement features 478 of the cannula 470. In this manner, the cannula 470 may be attached to the cutting tool 1300 as the cutting tool 1300 is inserted into the port 406 and forms the hole in the tissue wall. Specifically, the cutting tool 1300 may be configured for attaching the cannula 470 to the port 406 as the cutting tool 1300 forms the hole. In this manner, upon forming the hole and removing the cutting tool 1300 from the aperture 414, the cannula 470 remains attached to the port 406 and the hemostasis valve 462 positioned within the cannula 470 closes fluid communication through the connector 400.

Figure 13A:
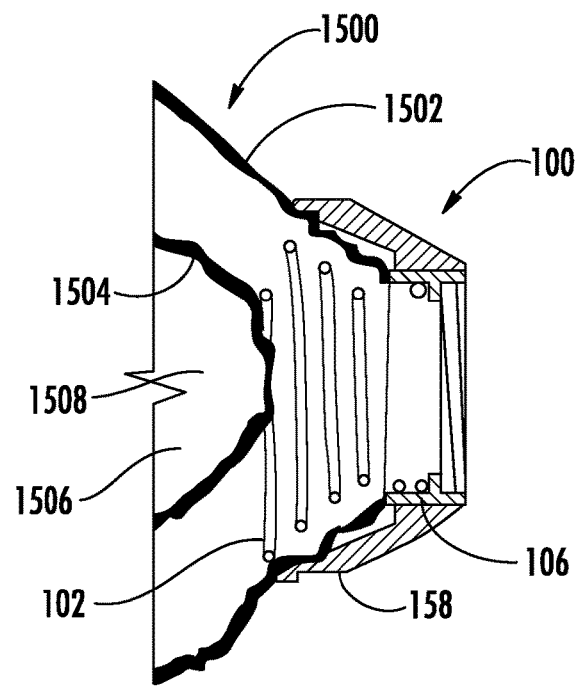

FIGS. 13A-13F illustrate an exemplary method for implanting a connector, such as the connector 100, and a medical device 1400 in a tissue wall 1500. As is shown, the tissue wall 1500 may include an outer first surface 1502 and an inner second surface 1504. Additionally, the tissue wall 1500 may define a cavity 1506 that may contain a fluid 1508. For example, in certain aspects, the cavity 1506 may be the left ventricle of a heart, and the fluid 1508 may be blood. As is shown in FIG. 13A, The method may include the step of advancing the anchoring device 102 of the connector 100 at least partially into the tissue wall 1500 to secure the connector 100 for subsequent use during a surgical procedure. In certain aspects, where the anchoring device 102 includes a helical coil or spring, the step of advancing the anchoring device 102 may include advancing the anchoring device 102 at least partially into the tissue wall 1500 along a helical path. In other aspects, where the anchoring device 102 includes pins, prongs, barbs, or hooks, the step of advancing the anchoring device 102 may include advancing the anchoring device 102 at least partially into the tissue wall 1500 along a linear path. In certain aspects, the step of advancing the anchoring device 102 of the connector 100 at least partially into the tissue wall 1500 may include compressing at least a portion of the tissue wall 1500 inward toward an axis of the connector 100. For example, such inward compression may be achieved by the anchoring device 102 including a radially expanding helical coil, as described above.

Figure 13B:
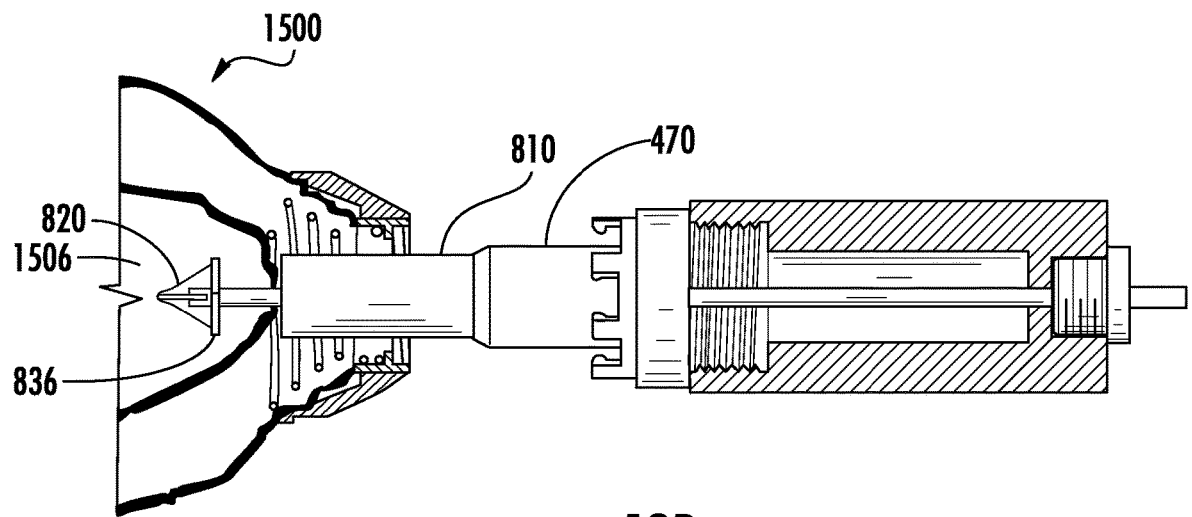

As is shown in FIG. 13B, the method also may include the step of piercing the tissue wall 1500 by advancing a piercing element 820 through the aperture 114 of the connector 100 and through the tissue wall 1500. The method further may include the step of coring a hole 1510 in the tissue wall 1500 by advancing a coring tube 810 through the aperture 114 of the connector 100 and through the tissue wall 1500. In certain aspects, the step of coring the hole 1510 in the tissue wall 1500 may include expanding an expandable element 836 within the cavity 1506 and moving the expandable element 836 against the second surface 1504 of the tissue wall 1500 and into the coring tube 810. In some aspects, the step of coring the hole 130 in the tissue wall 1500 may include the step of positioning a cannula 470 within the aperture 114 of the connector 100, as described above. In some such aspects, the cannula 470 may include a hemostatic valve 462 positioned therein for closing a fluid communication through the connector 100. In some aspects, a diameter of the hole 130 may be undersized relative to an outer diameter of the cannula 470, such that the cannula 470 compresses at least a portion of the tissue wall 1500 radially outward toward the anchoring device 102. In such aspects, the anchoring device 102 may include a coil or spring having a substantially constant helical diameter, as described above. Alternatively, the anchoring device 102 may include a coil or spring having an expanding helical diameter, as described above.

Figure 13C:
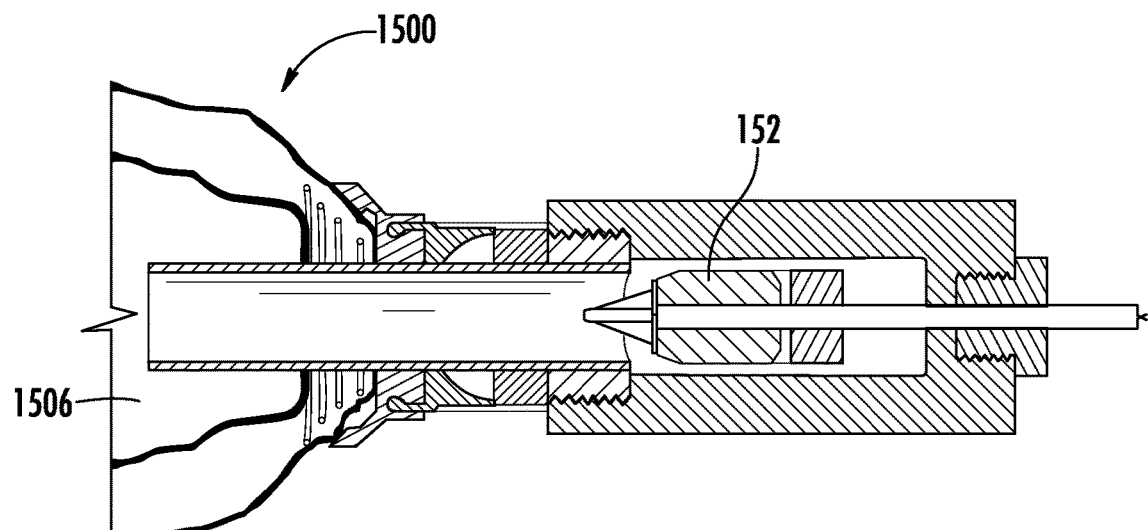

As is shown in FIG. 13C, the method further may include the step of retrieving the tissue core 1512 from the tissue wall 1500 and through the aperture 114 of the connector 100. In certain aspects, the step of retrieving the tissue core 1512 from the tissue wall 1500 may include moving the expandable element 836 through the coring tube 810. The method also may include the step of confirming retrieval of the tissue core 1512 from the tissue wall 1500 by viewing the tissue core 1512 through the coring handle 812.

Figure 13D:
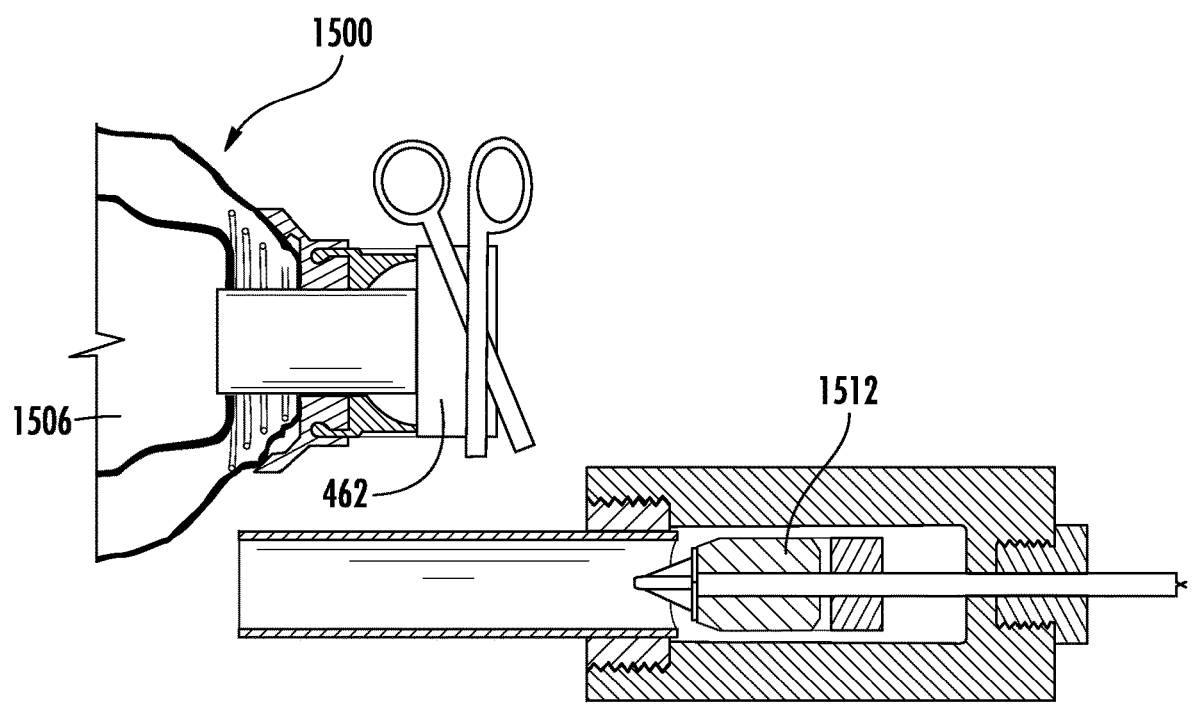

As is shown in FIG. 13D, the method also may include the step of removing the coring tube 810 from the aperture 114 of the connector 100. In certain aspects, the step of removing the coring tube from the connector 100 may include closing fluid communication through the aperture 114 of the connector 100. Specifically, in some such aspects, the step of removing the coring tube from the connector 100 may include closing fluid communication through the aperture 114 of the connector 100 with a hemostasis valve 162.

Figure 13E:
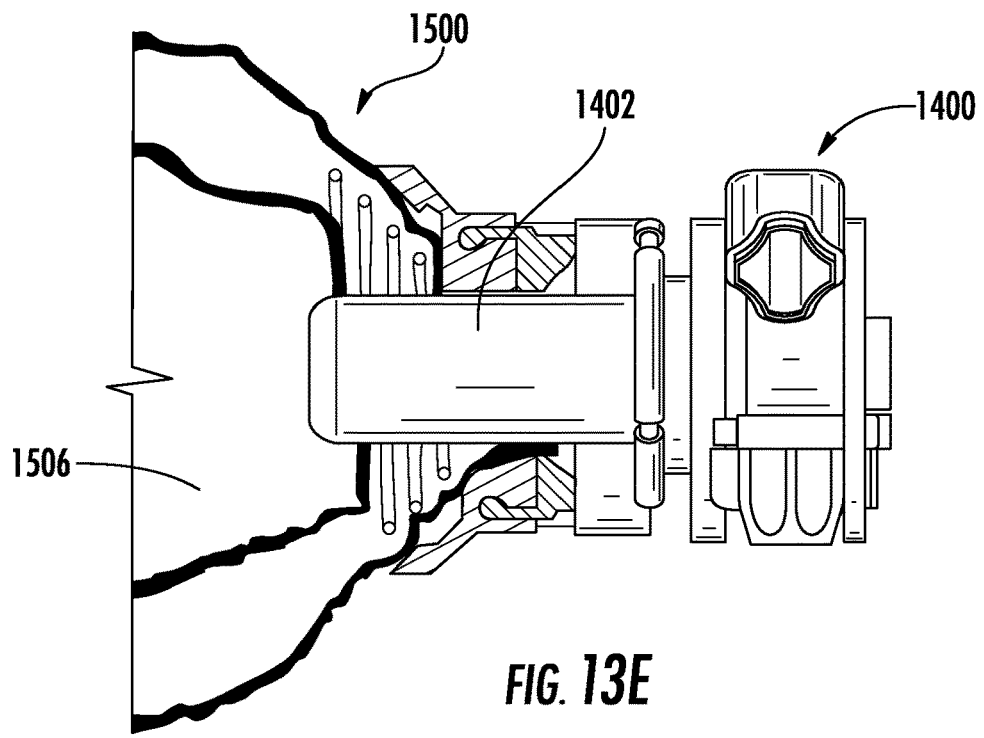
Figure 13F:
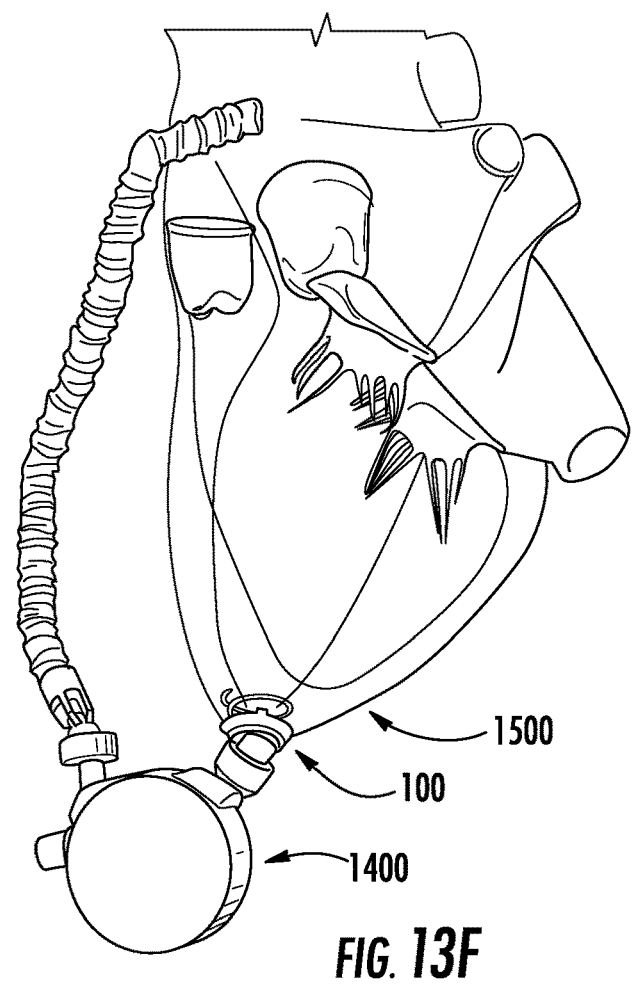

As is shown in FIG. 13E, the method further may include the step of coupling the medical device 1400 to the connector 100 such that an inlet tube 1402 of the medical device 1400 is in fluid communication with the cavity 1506 defined by the tissue wall 1500. In certain aspects, the medical device 1400 may be a left ventricular assist device, and the inlet tube 1402 may receive a flow of blood from the left ventricle 1506. In other aspects, the medical device 1400 may be an apicoaortic conduit, and the inlet tube 1402 may receive a flow of blood from the left ventricle 1506. In certain aspects, the step of coupling the medical device 1400 to the connector 100 may include axially retaining the inlet tube 1402 within the aperture 114 of the connector 100 via the coupler device 110. In some such aspects, the coupler device 110 may axially retain the inlet tube 1402 by frictional forces between the coupler device 110 and the smooth outer surface of the inlet tube 1402. In some aspects, a diameter of the hole 130 may be undersized relative to an outer diameter of the inlet tube 1402, such that the inlet tube 1402 compresses at least a portion of the tissue wall 1500 radially outward toward the anchoring device 102. In such aspects, the anchoring device 102 may include a coil or spring having a substantially constant helical diameter, as described above. Alternatively, the anchoring device 102 may include a coil or spring having an expanding helical diameter, as described above. In certain aspects, the method further may include the step of removing the medical device 1400 from the connector 100 and closing fluid communication through the connector via a biocompatible plug or cap.

It will be understood that the above-described method for implanting a connector and a medical device in a tissue wall may include additional or alternative steps and aspects, based on the foregoing description relating to the various connectors and tools described herein. Accordingly, as a result of the structure and functionality of the above-described connectors and tools, one skilled in the art would appreciate the different methods in which they may be utilized.

According to certain methods of implanting a connector, such as the various connectors described above, in a tissue wall of a heart, air may become trapped in a ventricle of the heart during implantation. In particular, this phenomenon may be observed with connectors including a hemostasis valve configured for controlling fluid communication therethrough. For example, FIG. 14A shows the connector 400 including the hemostasis valve 462 implanted in the tissue wall 1500 of a heart, the hemostasis valve 462 configured for controlling blood flow out of the ventricle of the heart. During implantation of the connector 400, an air bubble 1510 may become trapped in the ventricle adjacent the hemostasis valve 462, as is shown. As described above, the hemostasis valve 462 may be a multi-leaflet valve, such as the tri-leaflet valve of the embodiment of FIG. 14A. Based on the multi-leaflet configuration of the hemostasis valve 462, the air bubble 1510 may have a tendency to become trapped in the sinus (i.e., the base) of the leaflets 464 of the valve 462. In such instances, it may be desirable to de-air the ventricle.

FIGS. 14B-14D illustrate another exemplary embodiment of a connector 1600 configured for implanting and using in a tissue wall to establish, maintain, control, and close a fluid communication between opposing surfaces of the tissue wall, as may be described herein. The connector 1600 may include various elements corresponding to those described above with respect to the connectors 100, 200, 300, 400, 500, and 600, which elements are identified in FIGS. 14B-14D with corresponding numerals and may not be described in further detail herein. The connector 1600 may be utilized as a tissue connector configured for use in any number of surgical procedures, including, but not limited to, the example procedures described above. Specifically, the connector 1600 may be utilized as a heart connector configured for use in various cardiac procedures, including, but not limited to implantation of a VAD. As is shown, the connector 1600 may include an anchoring device 1602, a port 1606, a coupler device 1610, a hemostasis valve 1662, and a cannula 1670, which may be configured in a manner similar to the corresponding elements of the connector 400. Certain structural and functional differences between the connector 1600 and the connector 400 will be described as follows. Overall, the embodiment of the connector 1600 of FIGS. 14B-14D provides a de-airing solution to the air bubble problem described above.

Specifically, in certain aspects, the connector 1600 may include one or more de-airing orifices 1690. The de-airing orifices 1690 may be defined in the connector 1600 at the highest possible location that can be filled with air, where air bubbles may naturally tend to form or gather. In this manner, the de-airing orifices 1690 may best facilitate de-airing of the ventricle. According to certain embodiments, the de-airing orifices 1690 may be defined in the hemostasis valve 1662. For example, the de-airing orifices 1690 may be defined in the leaflets 1664 at a proximal end of the hemostasis valve 1662, where air bubbles may naturally tend to form or gather. In this manner, the de-airing orifices 1690 may be configured for de-airing the ventricle through the hemostasis valve 1662. Other locations for the de-airing orifices 1690 are contemplated, including locations on components of the connector 1600 other than the hemostasis valve 1662. In certain embodiments, the de-airing orifices 1690 may be defined in the port 1606 or the cannula 1670 of the connector 1600. In other embodiments, the de-airing orifices 1690 may be defined in any other component having a configuration that allows for communication of a fluid from the ventricle, or from another tissue cavity according to other uses of the connector 1600.

In certain embodiments, the de-airing orifices 1690 themselves may include valves or may be selectively closed during the implantation procedure in order to control the amount of blood lost during de-airing of the ventricle. For example, in some embodiments, the de-airing orifices 1690 may be configured to naturally assume a closed configuration and to be selectively opened by actuation or insertion of an element that would create the fluid communication directly or indirectly through the orifices 1690.

According to some embodiments, the configuration of the leaflets 1664 of the hemostasis valve 1662 may facilitate de-airing of the ventricle or other tissue cavity. For example, in some such embodiments, the hemostasis valve 1662 may include leaflets 1664 that do not coapt or close completely and thus de-airing orifices 1690 may be defined between the leaflets 1664. In this manner, the de-airing orifices 1690 may be configured for allowing a small amount of fluid leakage through the de-airing orifices 1690. Accordingly, the hemostasis valve 1662 may be configured for allowing some air to escape through the coaptation line between the leaflets 1664 instead of being trapped in the ventricle or other tissue cavity. Other non-leaflet configurations of the hemostatic valve 1662 are contemplated, such as diaphragm valves, collapsible tubes, glove valves or others, which also may include one or more de-airing orifices 1690 configured for de-airing the ventricle or other tissue cavity in a similar manner.

According to certain embodiments, the de-airing orifices 1690 are configured for not only allowing the passage of air but also allowing the passage of a small amount of blood or other fluid therethrough. In such embodiments, the fluid may be allowed to flow or otherwise be directed to flow over the surfaces of the hemostasis valve 1662. In this manner, the fluid may flow over the leaflets 1664, diaphragms, or other surfaces of the valve 1662 such that the fluid acts as a lubricant or fluid film that reduces friction when tools, conduits, or any other elements are passed through the hemostasis valve 1662. FIGS. 14E-14F illustrate a further embodiment of the connector 1600 configured for directing the fluid that passes through the de-airing orifices 1690. According to this embodiment, the hemostasis valve 1662 may include flaps 1694 positioned adjacent the de-airing orifices 1690 and configured for re-directing the flow of fluid onto friction contact surfaces of the valve 1662. For example, the flaps 1694 may be positioned proximal of the de-airing orifices 1690 and configured for re-directing the flow of fluid onto proximal surfaces of the leaflets 1664 of the valve 1662, as is shown. In this manner, the flaps 1694 further may be configured for preventing un-necessary spillage, splashing, or disturbance caused by the flow of fluid during the procedure. According to other embodiments, the hemostasis valve 1662 or other components of the connector 1600 may include non-flap features positioned adjacent the de-airing orifices 1690 or other leakage features and configured for re-directing the flow of fluid in a similar manner.

It will be understood that various embodiments of the technology described and shown herein may be used not only for conventional VAD implantation but also for intra-cardiac circulatory support. Such use may be facilitated by the intra-cardiac circulatory support system 1700 shown in FIGS. 15A-15D. In certain embodiments, the system 1700 may include a valved port 1710, an anchoring device 1720, and an intra-ventricular VAD 1730. The valved port 1710 and the anchoring device 1720 may be configured for delivering the intra-ventricular VAD 1730 into the ventricle of the heart, and the anchoring device 1720 may be configured for maintaining the intra-ventricular VAD 1730 therein for treatment of the patient. The intra-ventricular VAD 1730 may be, for example, a catheter based circulatory support system, such as the Impella Device from ABIOMED or another catheter based circulatory support system.

The anchoring device 1720 may be configured in a manner similar to the anchoring devices of the connectors described herein, the anchoring device 1720 being configured for attaching to the tissue wall of the heart. Specifically, the anchoring device 1720 may include one or more straight, conical, or heterogeneously shaped coils, pins, hooks, barbs, sutures, other mechanical interference elements, or combinations thereof, configured for attaching to the tissue wall of the heart. The valved port 1710 may be removably attached to the proximal end of the anchoring device 1720 and configured for receiving the intra-ventricular VAD 1730 therein, as is shown. The valved port 1710 may be further configured for maintaining hemostasis during delivery of the intra-ventricular VAD 1730 through the anchoring device 1720 and into the ventricle of the heart. Specifically, the valved port 1710 may include one or more valves 1740 positioned therein and configured for controlling fluid communication therethrough, as is shown. After delivery of the intra-ventricular VAD 1730 into the ventricle, the anchoring device 1720 may then be used as a closure element by itself or in combination with one or more other components of the system 1700 configured for occluding or closing fluid communication through the tissue wall of the heart. After occluding or closing fluid communication through the tissue wall, the valved port 1710 may be removed from the anchoring device 1720, leaving the anchoring device 1720 implanted in the tissue wall and the intra-ventricular VAD 1730 implanted in the ventricle, as is shown in FIG. 15B.

According to certain embodiments, the system 1700 may include a closure element 1750 configured for occluding or closing fluid communication through the tissue wall of the heart. Such occlusion or closure may be achieved by the closure element 1750 itself or in combination with inward tissue compression provided by the anchoring device 1720, as described above. In some embodiments, the closure element 1750 may be a plug, as is shown in FIGS. 15C and 15D, although the closure element 1750 may be a cap, a valve, or other mechanical element configured for occluding or closing fluid communication through the tissue wall of the heart. The closure element 1750 may include a pass-through orifice 1760 extending therethough and configured for allowing passage of a catheter 1770, cables, or any other elements of the system 1700 that may need to be externalized through the tissue wall. The closure element 1750 also may include a hemostasis element 1780 positioned within or adjacent to the pass-through orifice 1760 and configured for sealing around the catheter 1770, cables, or other externalized elements. Specifically, the hemostasis element 1780 may be a valve, a ring, or other mechanical elements configured for sealing around the catheter 1770, cables, or other externalized elements.

In some embodiments, the anchoring device 1720 may be configured for stabilizing the position of the intra-ventricular VAD 1730 implanted within the ventricle. Specifically, the anchoring device 1720 may be connected to the intra-ventricular VAD 1730 and configured for controlling the spatial position of the intra-ventricular VAD 1730 within the ventricle, preventing undesirable migration of the intra-ventricular VAD 1730. According to various embodiments, the anchoring device 1720 may be connected mechanically, magnetically, chemically, or in any other manner, to the intra-ventricular VAD 1730. Further, the anchoring device 1720 may be used as a structural platform configured for receiving or otherwise supporting a receiver, an interface, or a transmitter operable for wireless communication of data or power between the intra-ventricular VAD 1730 and a controller of the system 1700. It will be appreciated that, although the intra-cardiac circulatory support system 1700 may be shown and described herein as including the intra-ventricular VAD 1730, the intra-cardiac circulatory support system 1700 may include any type of intra-cardiac circulatory support device.

In some embodiments of the intra-cardiac circulatory support system 1700 described above, adjustability and control of the spatial position of the intra-ventricular VAD 1730 deployed within the ventricle may be attained by a connection element configured to connect the anchoring device 1720 or the closure element 1750 to the VAD 1730. The connection element may include a ball joint, a deformable beam, a universal joint, a linked structure, or any other type of mechanical interface configured for adjusting or altering in order to angle or otherwise adjust the relative position between the anchoring device 1720 or the closure element 1750 and the VAD 1730. In some embodiments, the connection element also may be configured for adjusting or otherwise changing in axial length to not only control angulation or rotation of the VAD 1730 but also the three-dimensional spatial position of the VAD 1730 relative to the anchoring device 1720 or the closure element 1750. Because the anchoring device 1720 may be deployed on a moving structure, such as a beating heart or other cardiac surface, the interface between the VAD 1730 and the mating component of the system 1700, such as the anchoring device 1720 or the closure element 1750, may include a motion absorption element. The motion absorption element may include a spring and a dampener, a viscoelastic material component, an accordion type structure, or any other component that creates an interface configured for absorbing or otherwise controlling the transference of motion between the anchoring device 1720 or the closure element 1750 and the VAD 1730. It will be appreciated that, although the foregoing features are described with respect to the intra-ventricular VAD 1730, such features similarly may be incorporated in a system for deployment of an intra-vascular VAD.

As explained above, the various connectors shown and described herein, such as the connectors 100, 200, 300, 400, 500, 600, and 1600, may be utilized as a heart connector configured for use in various cardiac procedures, including, but not limited to implantation of a VAD, such as the VAD 1400 including the inlet tube 1402. In some embodiments, the inlet tube 1402 of the VAD 1400 may have a surface treatment configured for promoting adhesion of the tissue or tissue ingrowth. Examples of the surface treatment may include bead sintering, titanium bead sintering, surface blasting, etching or coating to promote adhesion or tissue ingrowth. When using the VAD 1400 including the inlet tube 1402 having the surface treatment, the coupler device of the connector may be configured for attaching directly onto the treated surface of the inlet tube 1402, or through another component such as the hemostatic valve onto the treated surface of the inlet tube 1402, and may take advantage of the friction caused by the surface treatment of the inlet tube 1402 to increase the axial force lock between the connector and the inlet tube 1402.

It also will be understood that one or more of the components of the connectors, such as the anchoring device, the port, the coupler device, or the cannula, may have a surface treatment configured for promoting adhesion of the tissue or tissue ingrowth in surfaces that may require or benefit from this function. Examples of the surface treatment may include bead sintering, titanium bead sintering, surface blasting, etching or coating. In some embodiments, the cannula may be fully or partially covered using titanium bead sintering to improve healing, increase adhesion, and reduce the possibility of thrombus formation. It also will be understood that other, non-implantable components may be surface treated or coated to improve their function. For example, an outer surface of the coring tube of one of the cutting tools described above may have a surface treatment or coating configured for reducing the friction generated between the outer surface and the hemostasis valve of the connector during deployment of the connector.

As explained above, the various connectors shown and described herein, such as the connectors 100, 200, 300, 400, 500, 600, and 1600, may include a coupler device configured for receiving and locking a medical device, such as the inlet tube 1402 of the VAD 1400, in place relative to the connector. According to various embodiments, a screw, a clip, a hook, a worm gear, or other mechanical element or elements may be used (chemical or magnetic means may also be used in some embodiments) as an actuator or activator for the coupler device, moving the coupler device from an unlocked state to locked state or from a locked state to an unlocked state. In some embodiments, the actuator or activator element may be part of the coupler device. According to such embodiments, it is foreseeable that a locking tool may be used to engage and actuate the actuator or activator element for locking the coupler device within the surgical window, from outside the body or through percutaneous access.

FIGS. 16A and 16B show an exemplary locking tool 1800 for use with one or more of the above-described connecters for implanting and using in a tissue wall. The locking tool 1800 may be configured to actuate or activate the coupler device of the connector through rotational or linear motion, by electrical or magnetic means, or by chemical means. In some embodiments, the locking tool 1800 may be releasably attachable to an actuator or activator element 1810 of the coupler device, which may be a screw as is shown in FIG. 16A or a similar element. When attached to the actuator or activator element 1810, the locking tool 1800 may be rotated to transfer torque to the actuator or activator element 1810, which then actuates the coupler device and locks the VAD in place relative to the connector. Further actuation of the locking tool 1800 may release the tool 1800 from the coupler device. According to various embodiments, a releasable interface between the coupler device and the locking tool 1800 may be a mechanical thread, a joint, a nut, a magnetic interface, a chemical bond, a weak-point tearing interface, or any other means configured to allow the tool 1800 to remain in place while needed and then be released from the connector. In some embodiments, the connector may be delivered to the tissue wall with the locking tool 1800 attached to the connector. In other embodiments, a guiding element, wire, or thread, or a magnetic field may be used to guide the locking tool 1800 to the actuator or activator element 1810 after the connector is delivered to the tissue wall. In these embodiments, the guiding element may be released or left in place when actuation of the actuator or activator element 1810 via the locking tool 1800 is complete. In some embodiments, the locking tool 1800 itself may be implantable and may be permanently attached to the coupler device of the connector.

According to some embodiments, the locking tool 1800 may include a flexible shaft 1820, as is shown in FIG. 16A, configured for allowing the tool 1800 to bend during delivery or actuation of the actuator or activator element 1810, in order to facilitate use of the tool 1800 through small incisions or in a percutaneous manner. As discussed above, the interface between the coupler device and the locking tool 1800 may be threaded and may include a hexagonal nut or allen key interface for transferring torque between the tool 1800 and the coupler device. For embodiments including a threaded interface, the locking tool 1800 may include a plurality of knobs or handles 1830 configured for releasing the tool 1800 from the actuator or activator element 1810 by relative rotation of the knobs or handles 1830 or by relative linear motion of the knobs or handles 1830. Independent of the specific configuration of the interface between the coupler device and the locking tool 1800 or the releasing knobs or handles 1830, the flexible shaft itself should simplify surgical use of the tool 1800. For embodiments where flexibility is not desired or required, the locking tool 1800 may include a stiff shaft.

According to certain embodiments of the connectors described above for implantation of a VAD, such as the connector 400, the coupler device and the hemostasis valve may be configured for controlling the axial position of an inlet tube of an extra-cardiac VAD within the cannula. Therefore, the axial position of the inlet tube also may be controlled with respect to the cavity, such as the ventricle, in which fluid (i.e., blood) is contained. In certain applications, in order to avoid obstruction of an inlet orifice of the VAD inlet tube, particularly against the septum, it may be desirable to angle the VAD inlet tube with respect to the tissue wall.

FIGS. 17A and 17B illustrate another exemplary embodiment of a connector 1900 configured for implanting and using in a tissue wall to establish, maintain, control, and close a fluid communication between opposing surfaces of the tissue wall, as may be described herein. The connector 1900 may include various elements corresponding to those described above with respect to the connectors 100, 200, 300, 400, 500, 600, and 1600, which elements are identified in FIGS. 17A and 17B with corresponding numerals and may not be described in further detail herein. The connector 1900 may be utilized as a tissue connector configured for use in any number of surgical procedures, including, but not limited to, the example procedures described above. Specifically, the connector 1900 may be utilized as a heart connector configured for use in various cardiac procedures, including, but not limited to implantation of a VAD. As is shown, the connector 1900 may include an anchoring device 1902, a port 1906, a coupler device 1910, a hemostasis valve 1962, and a cannula 1970, which may be configured in a manner similar to the corresponding elements of the connector 400. Certain structural and functional differences between the connector 1900 and the connector 400 will be described as follows. Overall, the embodiment of the connector 1900 of FIGS. 17A and 17B allows for rotation or angulation of an inlet tube of a VAD coupled thereto, as may be beneficial in certain patient applications.

As is shown in FIGS. 17A and 17B, the connector 1900 may include a rotation element 1990 configured for allowing the VAD inlet tube to rotate relative to the anchoring device 1902 and/or the port 1906 of the connector 1900 in a manner that changes an angle of incidence of the VAD inlet tube with respect to the tissue wall. According to various embodiments, the rotation element 1990 may be positioned between the anchoring device 1902 and the port 1906, between the port 1906 and the cannula 1970, or between the cannula 1970 and the VAD inlet tube. According to the embodiment shown in FIGS. 17A and 17B, the rotation element 1990 may be a rotation knee-type joint positioned between the port 1906 and the cannula 1970 of the connector 1900. In this manner, the rotation element 1990 may be configured for allowing rotation of the cannula 1970 relative to the port 1906, thereby allowing rotation of the VAD inlet tube received within the cannula 1970 relative to the port 1906, the anchoring device 1902, and the tissue wall. In other embodiments, the rotation element 1990 may include one or more magnetic, mechanical, or chemical joints, or one or more deformable materials configured for allowing rotation of the VAD inlet tube relative to the tissue wall. In some embodiments, the connector 1900 also may include a locking mechanism configured for retaining, either permanently or temporarily, the angular position of the VAD inlet tube relative to the anchoring device 1902 and/or the port 1906 of the connector 1900. The locking mechanism may include one or more fasteners or interference elements, such as pins, screws, hooks, or other similar features configured to restrict the rotation of the VAD inlet tube via the rotation element 1990. In some embodiments, a rotation tool may be used to control rotation of the VAD inlet tube relative to the anchoring device 1902 and/or the port 1906 of the connector 1900. Further, a locking tool, such as the locking tool 1800 described above, may be used to facilitate actuation, locking, and/or unlocking, of the locking mechanism. In this manner, the connector 1900 may be configured to move from an unlocked state, allowing rotation of the VAD inlet tube relative to the tissue wall via the rotation element 1990, to a locked state, preventing rotation of the VAD inlet tube relative to the tissue wall. In some embodiments, a single combination tool may be configured for operating as the rotation tool and the locking tool. The rotation tool, the locking tool, or the combination tool may be controlled from inside or outside the body, depending on the invasiveness of the medical procedure being performed.

Many modifications and other embodiments of the present invention will come to mind to one skilled in the art to which the invention pertains upon having the benefit of the teachings presented herein through the foregoing descriptions and the associated drawings. Therefore, it is to be understood that the present invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A connector for implanting in a tissue wall, the connector comprising:
   an anchoring device configured for advancing at least partially through the tissue wall, wherein the anchoring device comprises a sharpened tip configured for piercing the tissue wall;
   a port attached to the anchoring device and positioned about a proximal end of the anchoring device, wherein the port defines an aperture therethrough;
   a cannula configured for positioning at least partially through the aperture of the port and engaging the port, wherein the cannula defines an aperture therethrough;
   a hemostasis valve positioned within the aperture of the cannula and configured for closing a fluid communication therethrough, wherein the hemostasis valve is positioned at least partially within the aperture of the port when the cannula and the port are engaged;

a coupler device positioned about the port, wherein the coupler device is configured for coupling to a medical device; and wherein the coupler device comprises a deflection arm configured for deflecting inward into an aperture of the coupler device and retaining the medical device.

2. The connector of claim 1, wherein the anchoring device is a suture-less device configured for advancing at least partially through the tissue wall.

3. The connector of claim 1, wherein the anchoring device comprises a helical coil or spring.

4. The connector of claim 3, wherein the helical coil or spring comprises a radially-expanding helical coil or spring such that a helical diameter of the coil or spring increases from a proximal end of the anchoring device toward a distal end of the anchoring device.

5. The connector of claim 1, wherein the anchoring device is configured for compressing at least a portion of the tissue wall inward toward an axis of the anchoring device when advanced at least partially therethrough.

6. The connector of claim 1, wherein the port comprises a flange formed about a distal end of the port, and wherein the flange is configured for contacting the tissue wall upon advancing the anchoring device at least partially therethrough.

7. The connector of claim 1, wherein the coupler device is a suture-less device configured for coupling to the medical device.

8. The connector of claim 1, wherein the coupler device is configured for receiving and axially retaining the medical device.

9. The connector of claim 1, wherein the medical device is an inlet tube of a ventricular assist device, and wherein the coupler device is configured for receiving and axially retaining the inlet tube.

10. The connector of claim 1, further comprising a secondary sealing element configured for contacting and sealing against the tissue wall upon advancing the anchoring device at least partially therethrough.

11. The connector of claim 10, wherein the secondary sealing element is formed as a substantially ring-shaped member positioned about a distal end of the port.

12. The connector of claim 1, wherein the hemostasis valve comprises a one-way valve.

13. The connector of claim 1, wherein the hemostasis valve comprises a one-way multi-leaflet valve.

14. The connector of claim 1, wherein the hemostasis valve is configured for allowing at least a portion of the medical device to pass therethrough.

15. The connector of claim 14, wherein the hemostasis valve is configured for forming a fluid-tight seal about an outer surface of the medical device.

16. The connector of claim 1, wherein the cannula is configured for positioning at least partially through the tissue wall.

17. The connector of claim 1, wherein the cannula comprises threads configured for engaging mating threads of the port.

18. The connector of claim 1, wherein the anchoring device comprises a plurality of pins, prongs, barbs, or hooks.

19. The connector of claim 1, wherein the cannula comprises an opening, and wherein the deflection arm is configured for passing through the opening of the cannula and engaging the hemostasis valve for retaining the medical device.

* * * * *